US007276483B1

(12) United States Patent
Castillo et al.

(10) Patent No.: US 7,276,483 B1
(45) Date of Patent: Oct. 2, 2007

(54) SMALL PEPTIDES FOR THE TREATMENT OF ALZHEIMER'S DISEASE AND OTHER BETA-AMYLOID PROTEIN FIBRILLOGENESIS DISORDERS

(76) Inventors: Gerardo M. Castillo, 20716 37th Ave. SE., Bothell, WA (US) 98021; Beth P. Nguyen, 223 - 189th Pl. SW., Bothell, WA (US) 98012; Thomas P. Lake, 19229 -22nd Ave. SE., Bothell, WA (US) 98012; Alan D. Snow, 3812 -167th Pl. SW., Lynnwood, WA (US) 98037

( * ) Notice: Subject to any disclaimer, the term of this patent is extended or adjusted under 35 U.S.C. 154(b) by 111 days.

(21) Appl. No.: 10/821,250

(22) Filed: Apr. 8, 2004

Related U.S. Application Data

(63) Continuation-in-part of application No. 09/962,955, filed on Sep. 24, 2001, now Pat. No. 6,933,280, which is a continuation-in-part of application No. 09/938,275, filed on Aug. 22, 2001, which is a continuation of application No. 08/947,057, filed on Oct. 8, 1997, now abandoned.

(60) Provisional application No. 60/461,655, filed on Apr. 8, 2003.

(51) Int. Cl.
*A61K 38/00* (2006.01)
*A61K 38/04* (2006.01)
*A61K 39/00* (2006.01)
*A61K 39/38* (2006.01)
*C07K 16/00* (2006.01)

(52) U.S. Cl. .......................... 514/14; 514/2; 424/185.2; 424/184.1; 530/300; 530/326

(58) Field of Classification Search ..................... None
See application file for complete search history.

(56) References Cited

OTHER PUBLICATIONS

Koo et al. "Amyloid β- Protein as a Substrate Interacts with Extracellular Matrix to Promote Neurite Outgrowth," Proc. Natl. Acad. Science, vol. 90, pp. 4748-4752, May 1993.
Narindrasorsak et al. "Characterization of High Affinity Binding between Laminin and Alzheimer's Disease Amyloid Precursor Proteins," Laboratory Investigation, vol. 67, No. 5, pp. 64-652, 1992.
Narindrasorsak et al. "An Interaction between Basement Membrane and Alzheimer Amyloid Precursor Proteins Suggests a Role in the Pathogenesis of Alzheimer's Diesease," Laboratory Investigation, vol. 72, No. 3, pp. 272-282, 1995.
Mann. "Cerebral Amyloidosis, Ageing and Alzheimer's Disease; A Contribution From Studies on Down's Syndrome," Neurobiology of Aging, vol. 10, pp. 397-399, 1989.
Gajdusek. "Unconventional viruses and the Origin and Disappearance of Kuru," Science, vol. 197, No. 4307, Sep. 2, 1977.
Prusiner et al. "Purification and Structural Studies of a Major Scrapie Prion Protein," Cell, vol. 38, 127-134, Aug. 1984.
Tateishi et al. "Gerstmann-Straussler-Scheinker Disease: Immunohistological and Experimental Studies," Annals of Neurology, vol. 24, No. 1, Jul. 1988.
Foidart et a. "Distribution and Immunoelectron Microscopic Localization of Laminin, A Non collagenous Basement Membrane Glycoprotein," Laboratory Investigation, vol. 42, No. 3, p. 336, 1980.
Burgeson et al. "A New Nomenclature for the Laminins," Matrix Biology, vol. 14, pp. 209-211, 1994.
Yurchenco et al. "Laminin Polymerization in Vitro: Evidence for a two step assembly with Domain Specificity," The Journal of Biology Chemistry, vol. 260, No. 12, pp. 7636-7644, Jun. 25, 1985.
Yurchenco et al., "Laminin Forms an Independent Network in Basement Membranes," The Journal of Cell Biology, vol. 117, No. 5, pp. 1119-1133, Jun. 1993.
Newgreen et al. "Fibronectin in Early Avian Embroys: Synthesis and Distribution Along the Migration Pathways of Neural Crest Cells," Cell Tissue Res. vol. 211, pp. 211-269, 1980.
Rovasio et al. "Neural Crest Cell Migration: Requirements for Exogenous Fibronectin and High Cell Density," The Journal of Cell Biology, vol. 96, pp. 462-473, Feb. 1983.
Lander et al. "Laminin is associated with the 'nuerite outgrowth-promotion factors' found in conditioned media," Proc. Natl. Acad. Sci. USA, vol. 82, pp. 2183-2187, Apr. 1985.
Fraser et al. "A monclonal antibody against a laminin-heparen sulfate proeoglycan complex perturbs cranial neural crest migration in vivo," The Journal of Cell Biology, vol. 106, pp. 1321-1329, Apr. 1988.
Kleinman et al. "Formation of a Supramolecular Complex Is Involved the Reconstitution of Basement Membrane Composets," Biochemistry, vol. 22, pp. 4969-4974, 1983.
Engvall et al. "Mapping of Domains in Human Laminin Using Monoclonal Antibodies: Localiztion of the Neurite-promotion Site," The Journal of Cell Biology, vol. 103, No. 6, Pt. 1, pp. 2457-2465, 1986.
Liese et al. "Laminin is induced in astrocytes of adult brain by injury," The EMBO Journal, vol. 3, No. 3, pp. 683-686, 1984.
Terranova et al. "Role of laminin in the attachment of PAM 212 (epithelial) Cells to Basement Membrane Collagen," Cell, vol. 22, pp. 719-726, Dec. 1980.
Rao et al. "Binding domain for laminin of type IV collagen," Biochemical and biophysical research communications, vol. 128, No. 1, Apr. 16, 1985.
Charonis et al. "Binding of laminin to type IV collagen: A morphological study," The Journal of Cell Biology, vol. 100, pp. 1848-1853, 1985.

(Continued)

*Primary Examiner*—Olga N. Chernyshev
(74) *Attorney, Agent, or Firm*—Patrick M. Dwyer

(57) ABSTRACT

A pharmaceutical composition, or pharmaceutical agent for treating Aβ amyloidosis in a patient that has at least one laminin-derived peptide or fragment thereof from the group D-A13, D-HA3G76, D-A4G82, D-A5G81, D-A5G101, D-HA3G47, D-HA3G58, D-HA3G74, D-HA3G83, D-A5G82, D-R-AG73, D-R-A13, D-R-HA3G76, D-R-A4G82, and D-R-A5G81.

4 Claims, 30 Drawing Sheets
(14 of 30 Drawing Sheet(s) Filed in Color)

OTHER PUBLICATIONS

Laurie et al. "Localization of Binding Sites for Laminin, Heparen Sulfate Proteoglycan and Fibronectin on Basement Membrane (Tyoe IV) Collagen," J. Mol. Biol., vol. 189, pp. 206-216, 1986.

Riopelle et al. "Functional interactions of neuronal heparan sulphate proteoglycans with laminin," Brain Research, vol. 525, pp. 92-100, 1990.

Battaglia et al. "Basement-membrane heparan sulfate proteoglycan binds to laminin by its heparan sulfate chains and to nidogen by sites in the protein core," Eur. J. Biochem., vol. 208, pp. 359-366, 1992.

Sakashita et al. "Basement membrane glycoprotein laminin binds to heparin," FEBS Letters, vol. 116, No. 2, Jul. 1980.

Del Rosso et al. "Binding of the basement-membrane glycoprotein laminin to glycosaminoglycans," Biochem. J., vol. 199, pp. 699-704, 1981.

Skubitz et al. "Localization of three distinct heparin-hinding Domains of Laminin by Monoclonal antibodies," The Journal of Biological Chemistry, vol. 263, No. 10, pp. 4861-4868, Apr. 5, 1988.

Hall et al. "The $\alpha_1/\beta_1$ and $\alpha_6/\beta_1$ integrin heterodimers mediate cell attachment to distinct sites on laminin," The Journal of Cell Biology, vol. 110, pp. 2175-2184, Jun. 1990.

Goodman et al. "Multiple cell surface receptors for the short arms of laminin: $\alpha 1/\beta 1$ integrin and RGD-dependent proteins mediate cell attachment only to domains III in Murine Tumor Laminin," The Journal of Cell Biology, vol. 113, No. 4, pp. 931-941, May 1991.

Yurchenco et al. "Heparin modulation of laminin polymerization," The Journal of Biological Chemistry, vol. 265, No. 7, pp. 3981-3991, Mar. 5, 1990.

Fox et al. "Recombinant nidogen consists of three globular domains and mediates binding of laminin to collagen type IV," The EMBO Journal, vol. 10, No. 11, pp. 3137-3146, 1991.

Sung et al. "Cell and Heparin Binding in the Distal Long Arm of Laminin: Identification of Active and Cryptic Sites with Recombinant and Hybrid Glycoprotein," The Journal of Cell Biology, vol. 123, No. 5, pp. 1255-1268, Dec. 1993.

Shimomura et al. "Studies on Macromolecular Components of human glomerular basement membrane and alterations in diabetes," Diabetes. vol. 36, Mar. 1987.

Lyon et al. "Co-deposition of basement membrane components during the induction of murine splenic AA amyloid," Laboratory Investigation, vol. 64, No. 6, p. 785, 1991.

Perlmutter et al. "Microangiopathy, the Vascular Basement Membrane and Alzheimer's Disease: A Review," Brain Research Bulletin, vol. 24, pp. 677-686, 1990.

Murtomaki et al. "Laminin and its neurite outgrowth-promotin domain in the brain in alzheimer's disease and down's syndrome patients, " Journal of Neuroscience Research, vol. 32, pp. 261-273, 1992.

Perlimutter et al. "Vascular basement membrane components and the lesions of Alzheimer's Disease: light and electron microscopic analyses," Laboratory Investigation, vol. 67, No. 5, p. 643, 1992.

Narindrasorasak et al. "Characterization of high affinity binding between lanimim and Alzheimer's Disease amyloid precursor proteins," Laboratory Investigation, vol. 67, No. 5, p. 643, 1992.

Naiki et al. "Kinetic analysis of amyloid fibril polymerization in vitro," Laboratory Investigation, vol. 65, No. 1, p. 104, 1991.

Levine et al. "Thioflavine T interaction with synthetic Alzheimer's Disease $\beta$-amyloid peptides: detection of amyloid aggregation in solution," Protein Science, vol. 2, pp. 404-410, 1993.

Maiki et al. "First-order kinetic model of alzheimer's $\beta$-amyloid fibril extension in vitro," Laboratory Investigation, vol. 74, No. 2, p. 374, 1996.

Westermark et al. "Islet amyloid in type 2 human diabetes mellitus and adult diabetic ats cantains a novel putative polypeptide hormone," American Journal of Pathology, vol. 127, No. 3, Jun. 1987.

Cooper et al. "Purification and characterization of a peptide from amyloid-rich pancreases of type 2 diabetic patients," Proc. Natl. Acad. Sci. USA, vol. 84, pp. 8628-8632, Dec. 1987.

Levine. "Thioflavine T interaction with amyloid $\beta$-sheet structures," Int. J. Exp. Clin. Invest., vol. 2, pp. 1-6, 1995.

Laemmli. "Cleavage of structural proteins during the assembly of the head of bacteriophage T4," Nature, vol. 227, Aug. 15, 1970.

Schagger et al. "Tricine-sodium dodecyl sulfate-polyacrylamide gel electrophoresis for the separation of proteins in the range from 1 to 100kDa," Analytical Biochemistry, vol. 166, pp. 168-379, 1987.

Sasaki et al. "The Iaminin B2 chain has a multidomain structures homologous to the B1 chain," The Journal of Biological Chemistry, vol. 262, No. 35, pp. 17111-17117, Dec. 15, 1987.

Sasaki et al. "Sequence of the cDNA encoding the laminin B1 chain reveals a multidomain protein containing cysteine-rich repeats," Proc. Natl. Acad. Sci. USA, vol. 84, pp. 935-939, Feb. 1987.

Durkin et al. "Primary structure of the mouse laminin B2 chain and Comparison with Laminin B1, " Biochemistry, vol. 27, pp. 5198-5204, 1988.

Sasaki et al. "Laminin, a multidomain protein," The Journal of Biological Chemistry, vol. 263, No. 32, pp. 16536-16544, Nov. 15, 1988.

Colognato et al. "Mapping of Network-forming, heparin-hinding, and $\alpha a\beta 1$ integrin-recognition sites within the $\alpha$-chain short arm of Laminin-1," The Journal of Biological Chemistry, vol. 270, No. 16, pp. 9398-9406, Apr. 21, 1995.

Mandybur et al. "Cerebral amyloid angiopathy: the vascular pathology and complications," Journal of Neuropathology and Experimental Neurology, vol. 45, No. 1, pp. 79-90, Jan. 1986.

Pardridge et al. "Amyloid angiopathy of Alzheimer's Disease: amino acid composition and partial sequence of a 4,200-dalton peptide isolated from cortical microvessels," Journal of Neurochemistry, vol. 49, No. 5, 1987.

Pike et al. "In vitro aging of $\beta$-amyloid protein causes peptide aggregation and neurotoxicity," Brain Research, vol. 563, pp. 311-314, 1991.

Pike et al. "Structure-activity analyses of $\beta$-amyloid peptides: contribution of the $\beta$25-35 region to aggregation and neurotoxicity," Journal of Neurochemistry, vol. 64, No. 1, 1995.

Harrigan et al. "Beta amyloid is neurotixic in hippocampal slice cultures," Neurobiology of Aging, vol. 16, No. 5, pp. 779-789, 1995.

Games et al. "Alzheimer-type neuropathology in transgenic mice overexpressing V717F $\beta$-amyloid precursor protein," Nature, vol. 373, Feb. 9, 1995.

Hsiao et al. "Age related CNS disorder and early death in transgenc FVB/N mice overexpressing Alzheimer amyloid precursors proteins," Neuron, vol. 15, pp. 1203-1218, Nov. 1995.

Flood et al. "An amyloid $\beta$-protein fragment, A$\beta$[12-28], equipotently impairs post-training memory processing when infected into different limbic system structures," Brain Research, vol. 663, pp. 271-276, 1994.

Flood et al. "Amnestic effects in mice of four synthetic peptides homologous to amyloid $\beta$-protein from protein from patients with Alzheimer's Disease," Proc. Natl. Acad. Sci. USA, vol. 88, pp. 3363-3366, Apr. 1991.

Harada et al. "Human amyloid protein: chemical variability and homogeneity," The Journal of Histochemistry and Cytochemistry, vol. 19, No. 1, 1971.

Metaxas. "Familial mediterranean fever and amyloidosis, " Kidney International, vol. 20, pp. 676-685, 1981.

Skinner et al. "The prealbumin nature of the amloid protein in familial amyloid polyneuropathy (Fap) swedish variety," Biochemical and Biophysical Research Communications, vol. 99, No. 4, pp. 1326-1332, 1981.

Saraiva et al. "Amyloid Fibril Protein in Familial Amyloidotic Polyneuropathy, Portuguese Type," J. Clin. Invest., vol. 74, pp. 104-119, Jul. 1984.

Saraiva et al. "Studies on plasma trasthyretin (prealbumin) in familial amyloidotic polyneuropathy, portuguese type," J. Lab. Clin. Med., vol. 102, No. 4, Pct. 1983.

Tawara et al. "Amyloid fibril protein in type 1 familial amyloiditic polyneuropathy in Japanese," J. Lab. Clin. Med., vol. 96, No. 6, Dec. 1981.

Jensson et al. "The saga of cystatin C gene mutation causing amyloid angiopathy and brain hemorrhage-clenical genetics in iceland," Clinical Genetics, vol. 36, pp. 367-377, 1989.

Wright et al. "Relationship of amyloid deposits int eh human aorta to aortic atherosclerosis," Laboratory Investigation, vol. 30, No. 6, p. 767, 1974.

Pitkanen et al. "Senile systemic amyloidosis," AJP, vol. 117, No. 3, Dec. 1984.

Johnson et al. "Biology of disease," Laboratory Investigation, vol. 66, No. 5, p. 522, 1992.

Butler et al. "Immunoreactive calcitonin in amyloid fibrils of medullary carcinoma of the thyriod gland," Arch Pathol Lab Med, vol. 110, Jul. 1986.

Berger et al. "Calcitonin-like immunoireactivity of amyloid fibrils in medullarry thyroid carcinomas," Virchows archiv a pathol anat histopathol, vol. 412, pp. 543-551, 1988.

Gejyo et al. "A new form of amyloid protein associated with chronic hemodialysis was identified as $\beta_2$-microglobulin," Biochemical and Biophysical Research Communications, vol. 129, No. 3, pp. 701-706, Jun. 28, 1985.

Gejyo et al. "$\beta_2$-microglobulin: a new form of amyloid associated with chronic hemodialysis," Kidney International, vol. 30, pp. 385-390, 1986.

Glenner et al. "Alzheimer's Disease: initial report of the purification and characterization of a novel cerebrovascular amyloid protein," Biochemical and Biophysical Research Communications, vol. 120, No. 3, pp. 885-890, May 16, 1984.

Masters et al. "Amyloid plaque core protein in Alzheimer's Disease and Down Syndrome," Proc. Natl. Acad. Sci. USA vol. 82, pp. 4245-4249, Jun. 1985.

Rumble et al. "Amyloid A4 protein and its precursor in Down's Syndrome and Alzheimer's Disease," The New England Journal of Medicine, vol. 320, No. 22, Jun. 1, 1989.

```
852                                                                        928
TSISLYMKPPPKPQTTGAWVADQFVLYLGSKNAKKEYMGLAIKNDNLVYVYNLGMKDVEILLDSKPVSSWPAYFSIV
  A4G-1   A4G-2   A4G-3   A4G-4   A4G-5   A4G-6   A4G-7   A4G-8   A4G-9  A4G-10

929                                                                       1005
KIERVGKHGKVFLTVPSSSSTAEEKFIKKGEFAGDDSLLDLTPEDTVFYVGGVPANFKLPASLNLPSYSGCLELATL
  A4G-11  A4G-12  A4G-13  A4G-14  A4G-15  A4G-16  A4G-17  A4G-18          A4G-19

1006                                                                      1082
NNDVISLYNFKHIYNMDPSKSVPCARDKLAFTQSRAASYFFDGSSYAVVRDITRRGKFGQVTRFDIEIRTPADNGLV
   A4G-20   A4G-21    A4G-22  A4G-23  A4G-24  A4G-25  A4G-26  A4G-27 A4G-28

1083                                                                      1159
LLMVNGSMFFSLEMRNGYLHVFYDFGFSNGPVHLEDTLKKAQINDAKYREISIIYHNDKKMILVVDRRHVKSTDNEK
   A4G-29   A4G-30  A4G-31   A4G-32  A4G-33   A4G-34   A4G-35  A4G-36  A4G-37

1160                                                                      1236
KKIPFTDIYIGGAPQEVLQSRTLRAHLPLDINFRGCMKGIQFQKKDFNLLEQTETLGVGYGCPEDSLISRRAYFNGQ
 A4G-38 A4G-39 A4G-40 A4G-41 A4G-42   A4G-43  A4G-44  A4G-45   A4G-46   A4G-47

1237                                                                      1313
SFIASIQKISFFDGFEGGFNFRTLQPNGLLFYYTSGSDVFSISLDNGTVVMDVKGIKVMSTDKQYHDGLPHFVVTSI
   A4G-48  A4G-49   A4G-50  A4G-51  A4G-52   A4G-53  A4G-54  A4G-55   A4G-56

1314                                                                      1390
SDTRYELVVDKSRLRGKNPTKGKAEQTQTTEKKFYFGGSPISPQYANFTGCISNAYPTRLDRDVEVEAFQRYSEKVH
  A4G-57  A4G-58  A4G-59  A4G-60   A4G-61  A4G-62   A4G-63  A4G-64   A4G-65   A4G-66

1391                                                                      1467
TSLYECPIESSPLFLLHKKGKNSSKPKTNKQGEKSKDAPSWDPIGLKFLEQKAPRDSHCHLFSSPRAIEHAYQYGGT
  A4G-67   A4G-68   A4G-69   A4G-70  A4G-71  A4G-72  A4G-73  A4G-74   A4G-75

1468                                                                      1544
ANSRQEFEHEQGDFGEKSQFSIRLKTRSSHGMIPYVSDQEENDPMTLPLAHGRLVPMPNVGHKKLKIRSQEKYNDGL
  A4G-76  A4G-77  A4G-78   A4G-79  A4G-80  A4G-81  A4G-82  A4G-83  A4G-84  A4G-85

1545                                                                      1621
WHDVIFIREKSSGRLVIDGLRVLEERLPPSGAAWKIKGPIYLGGVAPGRAVKNVQITSVYSFSGCLGNLQLNGASIT
  A4G-86  A4G-87  A4G-88  A4G-89  A4G-90  A4G-91  A4G-92  A4G-93    A4G-94

1622                                                                      1698
SASQTPSVTPCFEGPMETGTYFSTEGGYVVLDESFNIGLKPEIAPEVRPRSSSGTLVHGHSVNGEYLNVHMRNGQVI
   A4G-95    A4G-96   A4G-97  A4G-98   A4G-99  A4G-100  A4G-101  A4G-102  A4G-103

1699                                                                      1775
VKVNNGVRDFSTSVTPKQNLCDGRWHRITVIRDSNVVQLDVDSEVNHVVGPLNPKPVDHREPVFVGGVPESLLTPRL
  A4G-104  A4G-105     A4G-106  A4G-107  A4G-108  A4G-109  A4G-110  A4G-111  A4G-112

1776                     1815
APSKPFTGCIRHFVIDSRPVSFSKAALVSGAVSINSCPTA
   A4G-113  A4G-114   A4G-115  A4G-116
```

Figure 6

```
2679                                                                                        2757
TALKFHIQSPVPAPEPGKNTGDHFVLYMGSRQATGDYMGVSLRNQKVHWVYRLGKAGPTTLSIDENIGEQFAAVSIDR
 <--->  <--->  <--->  <--->  <--->  <--->  <--->  <--->  <--->  <--->  <-
  A5G-1   A5G-2   A5G-3   A5G-4   A5G-5   A5G-6   A5G-7   A5G-8   A5G-9  A5G-10

2758                                                                               2834
TLQFGHMSVTVEKQMVHEIKGDTVAPGSEGLLNLHPDDFVFYVGGYPSNFTPPEPLRFPGYLGCIEMETLNEEVVSLY
-->  <--->  <--->  <--->  <--->  <--->  <--->  <----->  <----->
    A5G-11  A5G-12  A5G-13  A5G-14  A5G-15  A5G-16  A5G-17       A5G-18

2835                                                                                2912
NFEQTFMLDTAVDKPCARSKATGDPWLTDGSYLDGSGFARISFEKQFSNTKRFDQELRLVSYNGIIFFLKQESQFLCL
 <--->  <--->  <--->  <--->  <--->  <--->  <--->  <--->  <--->  <--->  <-
A5G-19  A5G-20   A5G-21  A5G-22  A5G-23  A5G-24  AG5-25  A5G-26  AG5-27  A5G-28

2913                                                                         2980
AVQEGTLVLFYDFGSGLKKADPLQPPQALTAASKAIQVPLLAGNRKRVLVRVERATVPSVDQDNMLEMADAYYLGGVP
 <--->  <--->  <--->  <--->  <--->  <--->  <--->  <--->  <--->  <--->
A5G-29  A5G-30  A5G-31  A5G-32  A5G-33  A5G-34  A5G-35  A5G-36  A5G-37  A5G-38

2981                                                                                   3058
PEQLPLSLRQLFPSGGSVRGCIKGIKALGKYVDLKRLNTTGISPGCTADLLVGRTMTPHGHGFLPLALPDVAPITEVV
 <----->  <----->  <----->  <--->  <--->  <--->  <--->  <--->  <--->
  A5G-39    A5G-40    A5G-41   A5G-42  A5G-43  A5G-44  A5G-45  A5G-46  A5G-47

3059                                                                                      3146
YSGPGFRGTQDNNLLYYRTSPDGPYQVSLREGHVTLRFMNQEVETQRVFADGAPHYVAFYSNVTGVWLYVDDQLQLVK
 <--->  <--->  <--->  <--->  <--->  <--->  <--->  <--->  <--->
A5G-48  A5G-49  A5G-50  A5G-51  A5G-52  A5G-53  A5G-54  A5G-55    A5G-56

3147                                                                                  3224
SHERTTPMLQLQPEEPSRLLLGGLPVSGTFHNFSGCISNVFVQRLRGPQRVFDLHQNMGSVNVSVGCTPAQLIETSRA
 <--->  <--->  <--->  <--->  <--->  <--->  <--->  <--->  <--->    <--->
A5G-57  A5G-58  A5G-59  A5G-60  A5G-61  A5G-62  A5G-63  A5G-64  A5G-65      A5G-66

3225                                                                        3302
TAQKVSRRSRQPSQDLACTTPWLPGTIQDAYQPGGPLPSYLQPVGISPSHRNRLHLSMLVRPHAASQGLLLSTAPHSG
 <--->  <--->  <--->  <--->  <--->  <--->  <--->  <--->  <--->
A5G-67  A5G-68  A5G-69  A5G-70  A5G-71  A5G-72  A5G-73  A5G-74  A5G-75

3303                                                                                    3380
RSPSLVLFLNHGHPVAQTEGPGPRLQVQSRQHSRAGQWHRVSVRWGMQQIQLVVDGSQTWSQKALHHRVPRAERPQPY
 <--->  <--->  <--->  <--->  <--->  <--->  <--->  <--->  <--->  <--->
A5G-76  A5G-77  A5G-78  A5G-79  A5G-80  A5G-81  A5G-82  A5G-83  A5G-84  A5G-85

3381                                                                                  3458
TLSVGGLPASSYSSKLPVSVGFSGCLKKLQLDKQPLRTPTQMVGVTPCVSGPLEDGLFFPGSEGVVTLELPKAKMPYV
 <--->  <--->  <--->  <--->  <----->  <--->  <----->  <--->
A5G-86  A5G-87  A5G-88  A5G-89    A5G-90     A5G-91     A5G-92   A5G-93

3459                                                                                  3536
SLELEMRPLAAAGLIPHLGQALATPYMQLKVLTEQVLLQANDGAGEPSTWVTYPKLCDGRWHRVAVIMGRDTLRLEVD
 <--->  <--->  <--->  <--->  <--->  <--->  <--->  <----->  <--->
A5G-94  A5G-95  A5G-96  A5G-97  A5G-98  A5G-99  A5G-100   A5G-101  A5G-102

3537                                                                                3614
TQSNHTTGRLPESLAGSPALLHLGSLPKSSTARPELPAYRGCLRKLLINGAPVNVTASVQIQGAVGMRGCPSGTLALS
 <--->  <--->  <--->  <--->  <--->  <----->  <--->  <--->  <--->
A5G-103 A5G-104 A5G-105 A5G-106 A5G-107   A5G-108   A5G-109 A5G-110 A5G-111

3615        3635
KQGKALTQRHAKPSVSPLLH
 <--->  <--->
A5G-112  A5G-113
```

Figure 7

| PEPTIDES | Laminin Chain and Amino Acid Sequence Number | Amino Acid Sequence | % Disruption/ Disassembly of Fibrillar Aβ (Aβ:Peptide Molar Ratio of 1:6) |
| --- | --- | --- | --- |
| AG73 | Alpha-1 chain; residues 2719-2730 | RKRLQVQLSIRT | 46 % (S; p < 0.01)*** |
| A3 | Alpha-3 chain; residues 2243-2254 | KPRLQFSLDIQT | 23 % (S; p < 0.01) |
| A5 | Alpha-5 chain; residues 3275-3286 | RNRLHLSMLVRP | 22 % (S; p<0.01) |
| C-16 | Gamma-1 chain; residues 139-150 | KAFDITYVRLKF | 28 % (S; p<0.01)*** |
| LAM-L | Alpha-1 chain; residues 2097-2108 | AASIKVAVSADR | 24 % (S; p<0.01) |
| A-13 | Alpha-1 chain; residues 97-109 | RQVFQVAYIIIKA | 30 % (S; p<0.01)*** |
| HA3G45 | Alpha-3 chain; residues 1173-1184 | ASFGFQTFQPSG | 21 % (S; p<0.05) |
| HA3G47 | Alpha-3 chain; residues 1189-2000 | HQTWTRNLQVTL | 28 % (S; p<0.01)*** |
| HA3G58 | Alpha-3 chain; residues 1276-1287 | ISNVFVQRLSLS | 32 % (S; p<0.01)*** |
| HA3G67 | Alpha-3 chain; residues 1342-1353 | ASPPSVKVWQDA | 25 % (S; p<0.01)*** |
| HA3G71 | Alpha-3 chain; residues 1379-1390 | FKLPQELLKPRS | 23 % (S; p<0.05) |
| HA3G74 | Alpha-3 chain; residues 1402-1414 | RGLVFHTGTKNSF | 32 % (S; p<0.01)*** |
| HA3G75 | Alpha-3 chain; residues 1411-1422 | KNSFMALYLSKG | 24 % (S; p<0.01) |
| HA3G76 | Alpha-3 chain; residues 1418-1429 | YLSKGRLVFALG | 26 % (S; p<0.01)*** |
| HA3G79 | Alpha-3 chain; residues 1444-1455 | NDGKWHTVVFGH | 27 % (S; p<0.01)*** |
| HA3G83 | Alpha-3 chain; residues 1477-1487 | GNSTISIRAPVY | 33 % (S; p<0.01)*** |
| A4G31 | Alpha-4 chain; residues 1101-1112 | LHVFYDFGFSNG | 23 % (S; p<0.01) |
| A4G82 | Alpha-4 chain; residues 1513-1524 | TLFLAHGRLVFM | 30 % (S; p<0.01)*** |
| A5G15 | Alpha-5 chain; residues 2792-2803 | HPDDFVFYVGGY | 30 % (S; p<0.01)*** |
| A5G35 | Alpha-5 chain; residues 2950-2961 | VLVRVERATVFS | 20 % (S; p<0.05) |
| A5G46 | Alpha-5 chain; residues 3043-3054 | FLPLALPDVAPI | 21 % (S; p<0.05) |
| A5G56 | Alpha-5 chain; residues 3135-3146 | WLYVDDQLQLVK | 27 % (S; p<0.01)*** |
| A5G71 | Alpha-5 chain; residues 3259-3270 | GPLPSYLQFVGI | 22 % (S; p<0.05) |
| A5G80 | Alpha-5 chain; residues 3329-3340 | VQSRQHSRAGQW | 25 % (S; p<0.01)*** |
| A5G81 | Alpha-5 chain; residues 3337-3348 | AGQWHRVSVRWG | 41 % (S; p<0.01)*** |
| A5G82 | Alpha-5 chain; residues 3345-3356 | VRWGMQQIQLVV | 29 % (S; p<0.01)*** |
| A5G84 | Alpha-5 chain; residues 3361-3372 | TWSQKALHHRVP | 27 % (S; p<0.01)*** |
| A5G101 | Alpha-5 chain; residues 3516-3527 | DGRWHRVAVIMG | 39 % (S; p<0.01)*** |
| A5G109 | Alpha-5 chain; residues 3587-3598 | APVNVTASVQIQ | 32 % (S; p<0.01)*** |
| A5G110 | Alpha-5 chain; residues 3594-3605 | SVQIQGAVGMRG | 23 % (S; p<0.05) |

*** Selected for Further Testing

Figure 8

| PTI- | Structure | Formula | MW |
|---|---|---|---|
| DP-001<br>D-AG73 or<br>D-A1<br>A1-chain<br>2719-2730 | Arg-Lys-Arg-Lue-Gln-Val-Gln-Leu-Ser-Ile-Arg-Thr | $C_{64}H_{120}N_{24}O_{17}$ | 1497.82 |
| DP-002<br>D-A13<br>A1-chain<br>97-109 | Arg-Gln-Val-Phe-Gln-Val-Ala-Tyr-Ile-Ile-Ile-Lys-Ala | $C_{74}H_{121}N_{19}O_{17}$ | 1548.90 |
| DP-003<br>D-HA3G76<br>A3-chain<br>1418-1429 | Tyr-Leu-Ser-Lys-Gly-Arg-Leu-Val-Phe-Ala-Leu-Gly | $C_{63}H_{102}N_{16}O_{15}$ | 1323.61 |
| DP-004<br>D-A4G82<br>A4-chain<br>1513-1524 | Thr-Leu-Phe-Leu-Ala-His-Gly-Arg-Leu-Val-Phe-Met | $C_{67}H_{105}N_{17}O_{14}S$ | 1404.75 |
| DP-005<br>D-A5G81<br>A5-chain<br>3337-3348 | Ala-Gly-Gln-Trp-His-Arg-Val-Ser-Val-Arg-Trp-Gly | $C_{65}H_{95}N_{23}O_{15}$ | 1438.62 |
| DP-006<br>D-A5G101<br>A5-chain<br>3516-3527 | Asp-Gly-Arg-Trp-His-Arg-Val-Ala-Val-Ile-Met-Gly | $C_{61}H_{97}N_{21}O_{15}S$ | 1396.65 |
| DP-007<br>D-HA3G47<br>A3-chain<br>1189-2000 | His-Gln-Thr-Trp-Thr-Arg-Asn-Leu-Gln-Val-Thr-Leu | $C_{66}H_{105}N_{21}O_{19}$ | 1496.70 |
| DP-008<br>D-HA3G58<br>A3-chain<br>1276-1287 | Ile-Ser-Asn-Val-Phe-Val-Gln-Arg-Leu-Ser-Leu-Ser | $C_{61}H_{103}N_{17}O_{18}$ | 1362.60 |

Fig. 12a

| PTI- | Structure | Formula | MW |
|---|---|---|---|
| DP-009<br>D-HA3G74<br>A3-chain<br>1402-1414 | Arg-Gly-Leu-Val-Phe-His-Thr-Gly-Thr-Lys-Asn-Ser-Phe | $C_{66}H_{102}N_{20}O_{18}$ | 1463.67 |
| DP-010<br>D-HA3G83<br>A3-chain<br>1477-1487 | Gly-Asn-Ser-Thr-Ile-Ser-Ile-Arg-Ala-Pro-Val-Tyr | $C_{56}H_{92}N_{16}O_{18}$ | 1277.45 |
| DP-011<br>D-A5G82<br>A5-chain<br>3345-3356 | Val-Arg-Trp-Gly-Met-Gln-Gln-Ile-Gln-Leu-Val-Val | $C_{66}H_{109}N_{19}O_{16}S$ | 1456.78 |
| DP-012<br>D-A5G109<br>A3-chain<br>1444-1455 | Ala-Pro-Val-Asn-Val-Thr-Ala-Ser-Val-Gln-Ile-Gln | $C_{53}H_{91}N_{15}O_{18}$ | 1226.40 |
| DP-013<br>D-rAG73 or<br>D-rA1<br>A1-chain<br>r2719-2730<br>or<br>2730-2719 | Thr-Arg-Ile-Ser-Leu-Gln-Val-Gln-Leu-Arg-Lys-Arg | $C_{64}H_{120}N_{24}O_{17}$ | 1497.82 |
| DP-014<br>D-rA13<br>A1-chain<br>r92-109<br>or<br>109-92 | Ala-Lys-Ile-Ile-Ile-Tyr-Ala-Val-Gln-Phe-Val-Gln-Arg | $C_{74}H_{121}N_{19}O_{17}$ | 1547.92 |
| DP-015<br>D-rHA3G76<br>A3-chain<br>r1418-1429<br>or<br>1429-1418 | Gly-Leu-Ala-Phe-Val-Leu-Arg-Gly-Lys-Ser-Leu-Tyr | $C_{63}H_{102}N_{16}O_{15}$ | 1323.61 |
| DP-016<br>D-rA4G82<br>A4-chain<br>r1513-1524<br>or<br>1524-1513 | Met-Phe-Val-Leu-Arg-Gly-His-Ala-Leu-Phe-Leu-Thr | $C_{67}H_{105}N_{17}O_{14}S$ | 1404.75 |

Fig. 12b

| PTI- | Structure | Formula | MW |
|---|---|---|---|
| DP-017 D-rA5G81 A5-chain r3337-3348 or 3348-3337 | Gly-Trp-Arg-Val-Ser-Val-Arg-His-Trp-Gln-Gly-Ala 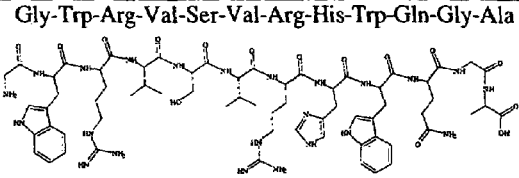 | $C_{65}H_{95}N_{23}O_{15}$ | 1438.62 |
| DP-018 D-rA5G101 A5-chain r3516-3527 or 3527-3516 | Gly-Met-Ile-Val-Ala-Val-Arg-His-Trp-Arg-Gly-Asp 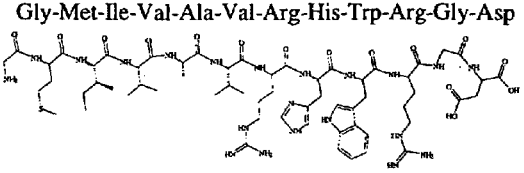 | $C_{61}H_{97}N_{21}O_{15}S$ | 1396.65 |
| LP-019 AG73 or A1 A1-chain 2719-2730 | Arg-Lys-Arg-Lue-Gln-Val-Gln-Leu-Ser-Ile-Arg-Thr 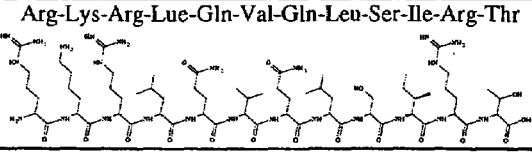 | $C_{64}H_{120}N_{24}O_{17}$ | 1497.82 |
| LP-020 A13 A1-chain 92-109 | Arg-Gln-Val-Phe-Gln-Val-Ala-Tyr-Ile-Ile-Ile-Lys-Ala 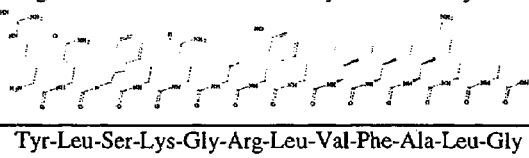 | $C_{74}H_{121}N_{19}O_{17}$ | 1548.90 |
| LP-021 HA3G76 A3-chain 1418-1429 | Tyr-Leu-Ser-Lys-Gly-Arg-Leu-Val-Phe-Ala-Leu-Gly 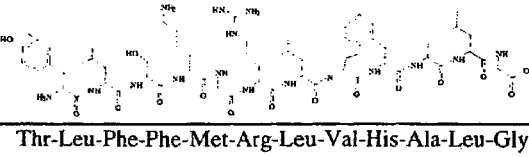 | $C_{63}H_{102}N_{16}O_{15}$ | 1323.61 |
| LP-022 A4G82 A4-chain 1513-1524 | Thr-Leu-Phe-Phe-Met-Arg-Leu-Val-His-Ala-Leu-Gly 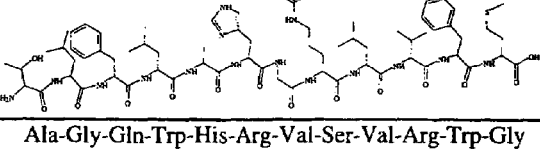 | $C_{67}H_{105}N_{17}O_{14}S$ | 1404.75 |
| LP-023 A5G81 A5-chain 3337-3348 | Ala-Gly-Gln-Trp-His-Arg-Val-Ser-Val-Arg-Trp-Gly 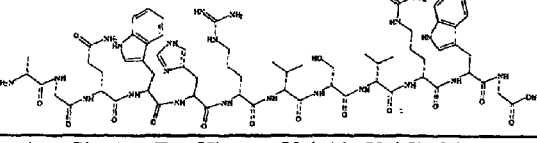 | $C_{65}H_{95}N_{23}O_{15}$ | 1438.62 |
| LP-024 A5G101 A5-chain 3516-3527 | Asp-Gly-Arg-Trp-His-Arg-Val-Ala-Val-Ile-Met-Gly 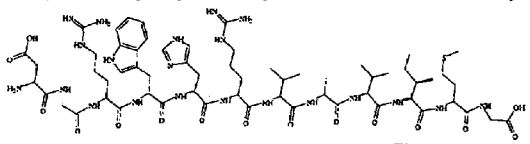 | $C_{61}H_{97}N_{21}O_{15}S$ | 1396.65 |

Fig. 12c

| PTI- | Structure | Formula | MW |
|---|---|---|---|
| LP-025 β-sheet breaker or iAβ5 | Leu-Pro-Phe-Phe-Asp | $C_{33}H_{43}N_5O_8$ | 637.74 |
| DP-026 Trc'n 5;1-7 | Ala-Gly-Gln-Trp-His-Arg-Val | $C_{38}H_{56}N_{14}O_9$ | 852.95 |
| DP-027 Trc'n 5;2-8 | Gly-Gln-Trp-His-Arg-Val-Ser | $C_{38}H_{56}N_{14}O_{10}$ | 868.95 |
| DP-028 Trc'n 5;3-9 | Gln-Trp-His-Arg-Val-Ser-Val | $C_{41}H_{62}N_{14}O_{10}$ | 911.04 |
| DP-029 Trc'n 5;4-10 | Trp-His-Arg-Val-Ser-Val-Arg | $C_{42}H_{66}N_{16}O_9$ | 939.09 |
| DP-030 Trc'n 5;5-11 | His-Arg-Val-Ser-Val-Arg-Trp | $C_{42}H_{66}N_{16}O_9$ | 939.09 |
| DP-031 Trc'n 5;6-12 | Arg-Val-Ser-Val-Arg-Trp-Gly | $C_{38}H_{62}N_{14}O_9$ | 859.00 |
| DP-032 Trc'n 6;1-7 | Asp-Gly-Arg-Trp-His-Arg-Val | $C_{40}H_{60}N_{16}O_{10}$ | 925.02 |

Fig. 12d

| PTI- | Structure | Formula | MW |
|---|---|---|---|
| DP-033 Trc'n 6;2-8 | Gly-Arg-Trp-His-Arg-Val-Ala | $C_{39}H_{60}N_{16}O_8$ | 881.01 |
| DP-034 Trc'n 6;3-9 | Arg-Trp-His-Arg-Val-Ala-Val | $C_{42}H_{66}N_{16}O_8$ | 923.09 |
| DP-035 Trc'n 6;4-10 | Trp-His-Arg-Val-Ala-Val-Ile | $C_{42}H_{65}N_{13}O_8$ | 880.07 |
| DP-036 Trc'n 6;5-11 | His-Arg-Val-Ala-Val-Ile-Met | $C_{36}H_{64}N_{12}O_8S$ | 825.05 |
| DP-037 Trc'n 6;6-12 | Arg-Val-Ala-Val-Ile-Met-Gly | $C_{32}H_{60}N_{10}O_8S$ | 744.96 |
| DP-038 Trc'n 4;1-7 | Thr-Leu-Phe-Leu-Ala-His-Gly | $C_{36}H_{55}N_9O_9$ | 757.89 |
| DP-039 Trc'n 4;2-8 | Leu-Phe-Leu-Ala-His-Gly-Arg | $C_{38}H_{60}N_{12}O_8$ | 812.97 |
| DP-040 Trc'n 4;3-9 | Phe-Leu-Ala-His-Gly-Arg-Leu | $C_{38}H_{60}N_{12}O_8$ | 812.98 |

Fig. 12e

| PTI- | Structure | Formula | MW |
|---|---|---|---|
| DP-041 Trc'n 4;4-10 | Leu-Ala-His-Gly-Arg-Leu-Val | C₃₄H₆₀N₁₂O₈ | 764.93 |
| DP-042 Trc'n 4;5-11 | Ala-His-Gly-Arg-Leu-Val-Phe | C₃₇H₅₈N₁₂O₈ | 798.95 |
| DP-043 Trc'n 4;6-12 | His-Gly-Arg-Leu-Val-Phe-Met | C₃₉H₆₂N₁₂O₈S | 859.07 |
| DP-044 Trc'n 15;1-7 | Gly-Leu-Ala-Phe-Val-Leu-Arg | C₃₇H₆₂N₁₀O₈ | 774.97 |
| DP-045 Trc'n 15;2-8 | Leu-Ala-Phe-Val-Leu-Arg-Gly | C₃₇H₆₂N₁₀O₈ | 774.97 |
| DP-046 Trc'n 15;3-9 | Ala-Phe-Val-Leu-Arg-Gly-Lys | C₃₇H₆₃N₁₁O₈ | 789.98 |
| DP-047 Trc'n 15;4-10 | Phe-Val-Leu-Arg-Gly-Lys-Ser | C₃₇H₆₃N₁₁O₉ | 805.98 |
| DP-048 Trc'n 15;5-11 | Val-Leu-Arg-Gly-Lys-Ser-Leu | C₃₄H₆₅N₁₁O₉ | 771.96 |
| DP-049 Trc'n 15;6-2 | Leu-Arg-Gly-Lys-Ser-Leu-Tyr | C₃₈H₆₅N₁₁O₁₀ | 836.01 |

Fig. 12f

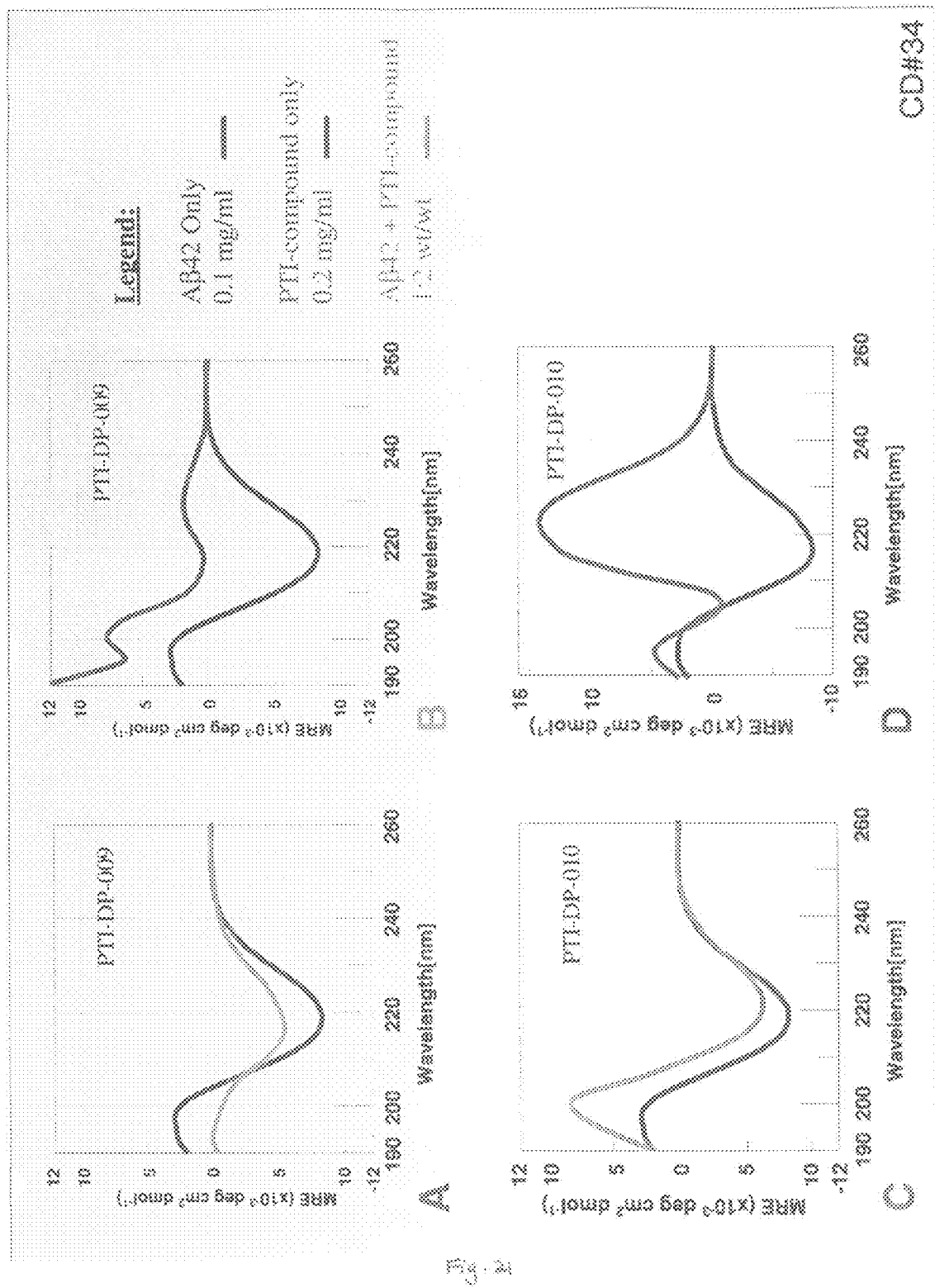

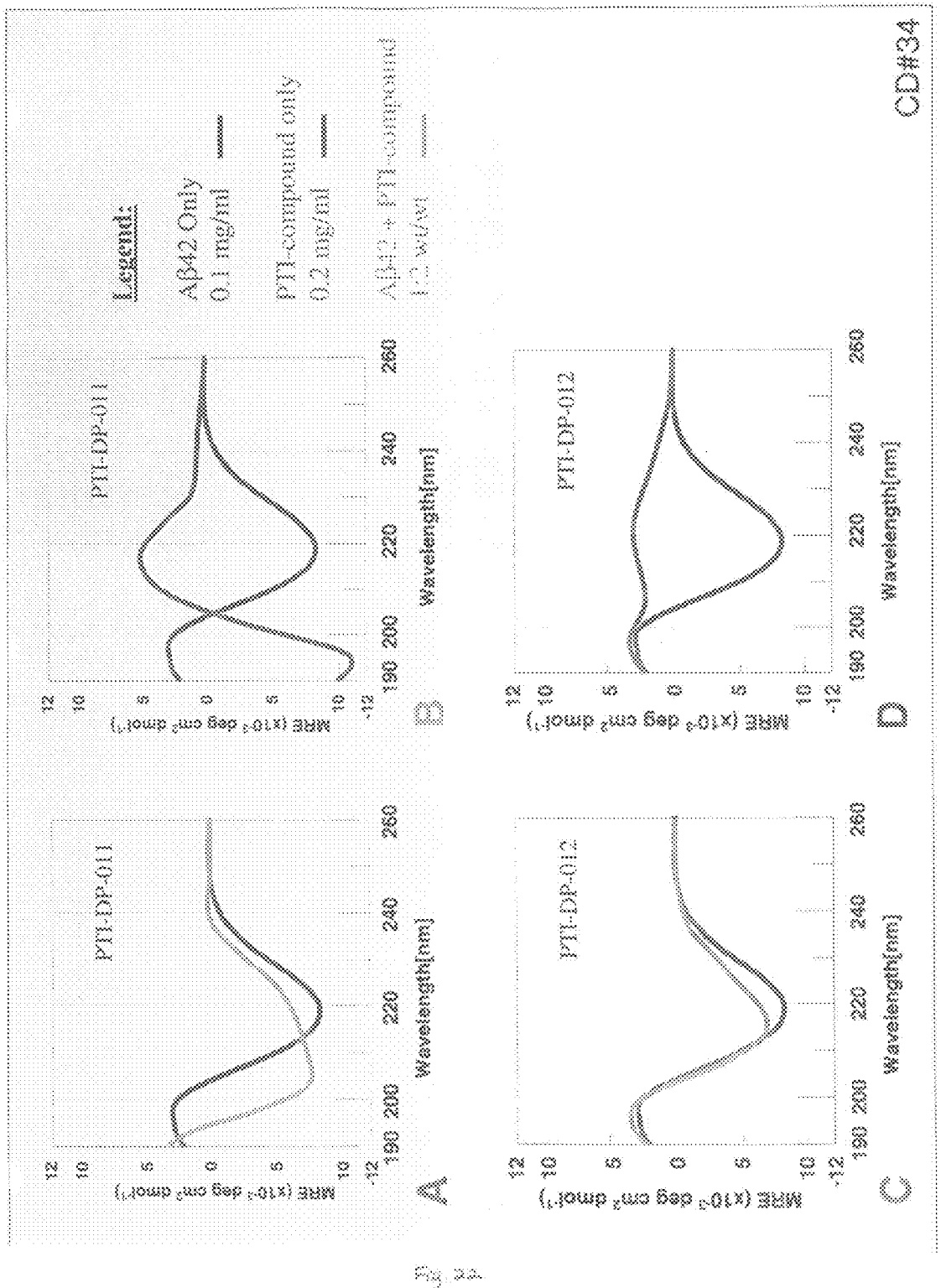

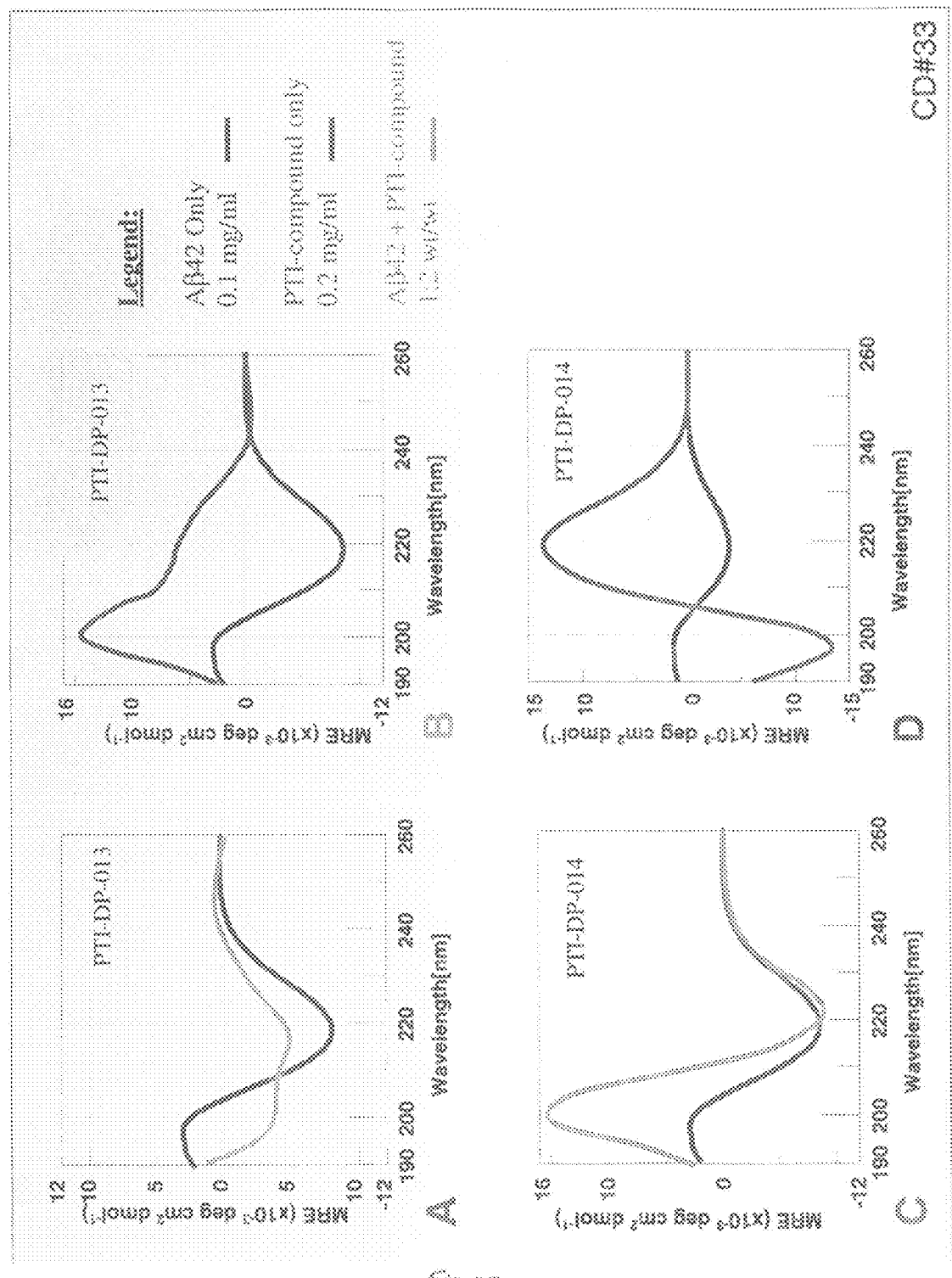

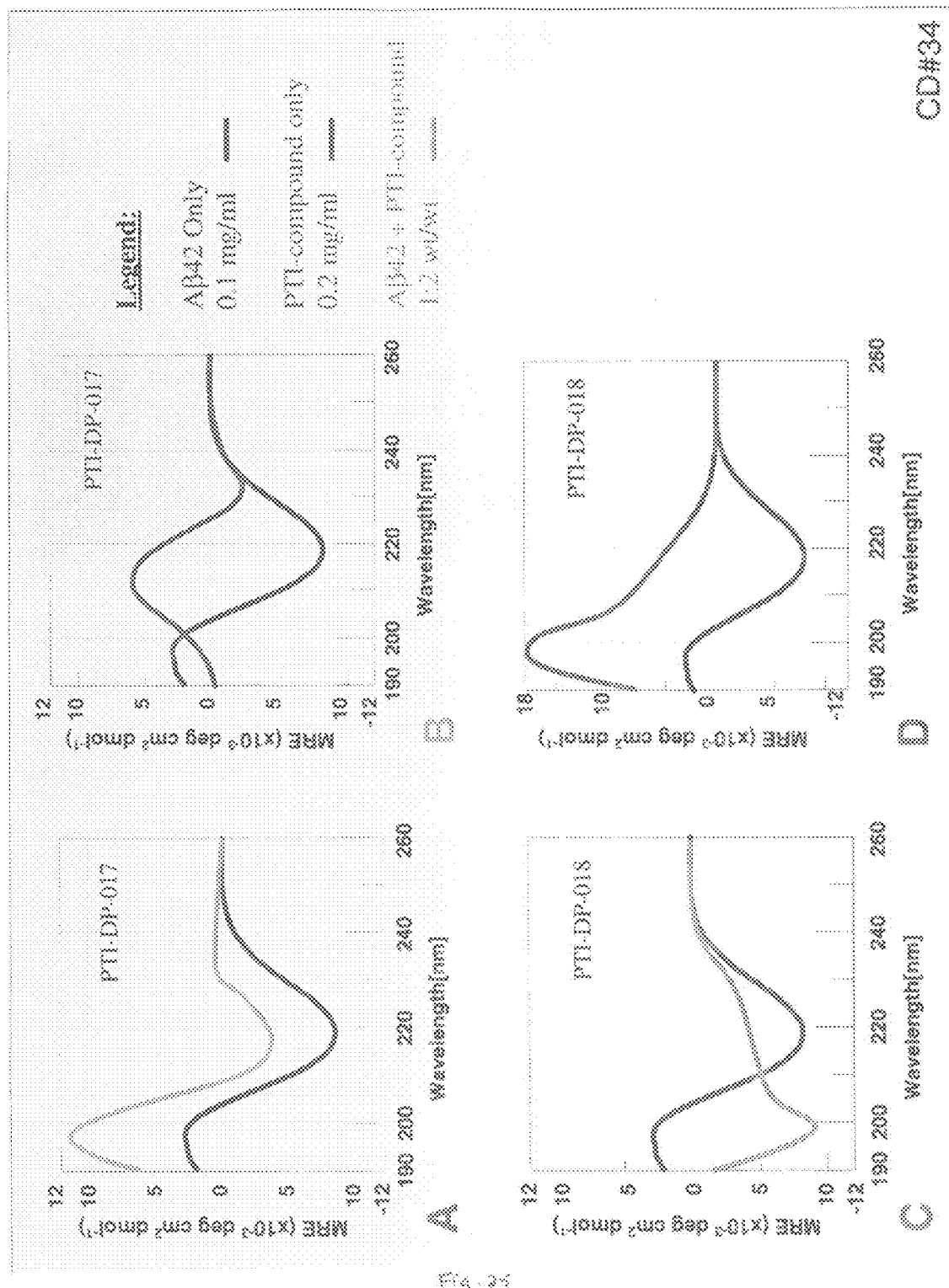

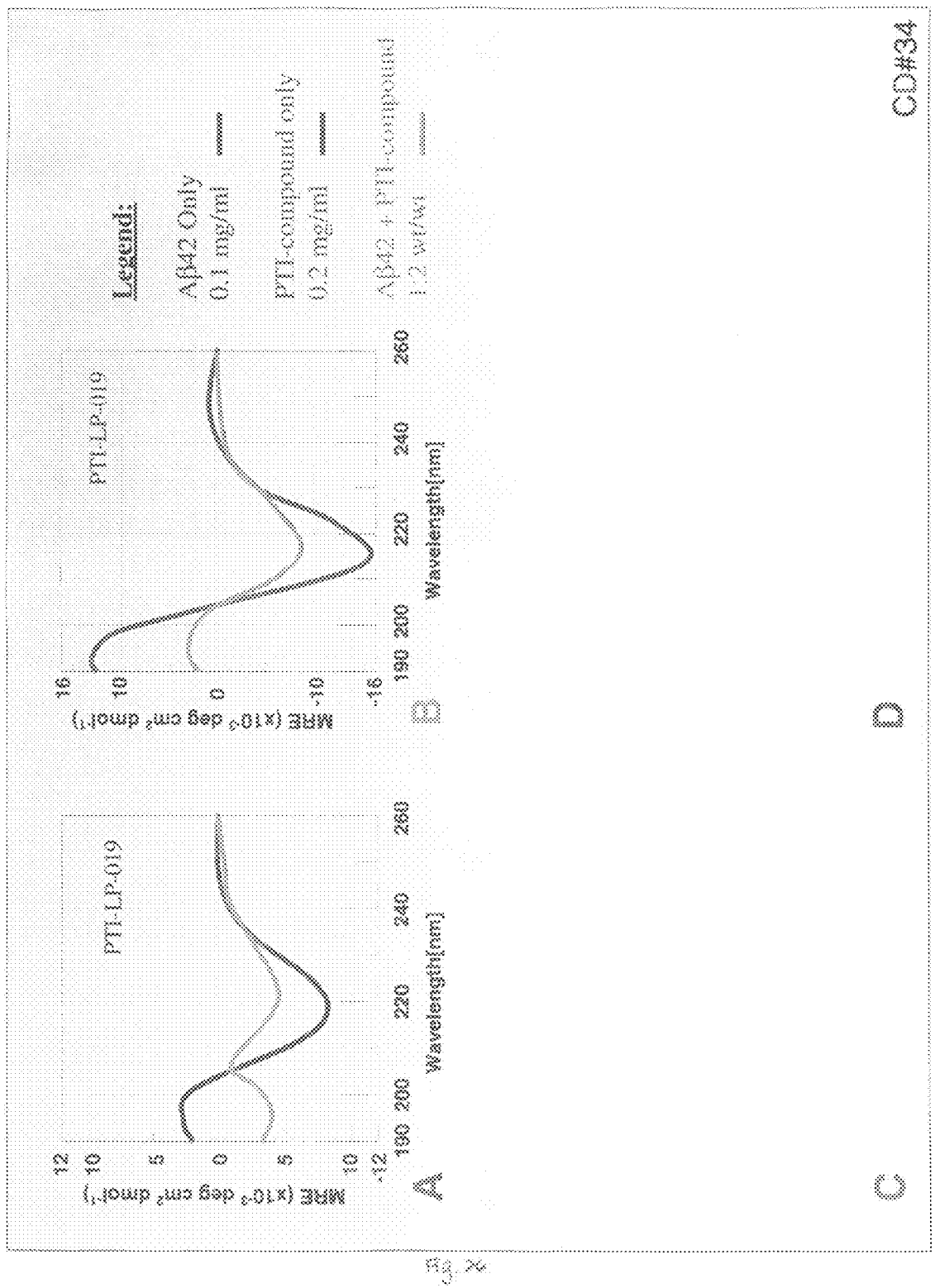

SEQUENCE LISTING

<160> NUMBER OF SEQ ID NOS: 108

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 1

Arg Lys Arg Leu Gln Val Gln Leu Ser Ile Arg Thr
  1               5                  10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Ala Phe Asp Ile Thr Tyr Val Arg Leu Lys Phe
  1               5                  10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Gln Val Phe Gln Val Ala Tyr Ile Ile Ile Lys Ala
  1               5                  10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

His Gln Thr Trp Thr Arg Asn Leu Gln Val Thr Leu
  1               5                  10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ile Ser Asn Val Phe Val Gln Arg Leu Ser Leu Ser
  1               5                  10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Ser Pro Pro Ser Val Lys Val Trp Gln Asp Ala
  1               5                  10

<210> SEQ ID NO 7
<211> LENGTH: 13
<212> TYPE: PRT
```

```
-continued

<213> ORGANISM: Artificial Sequence
<220> FEATURE:
<223> OTHER INFORMATION: Description of Artificial Sequence: Synthetic
      peptide

<400> SEQUENCE: 7

Arg Gly Leu Val Phe His Thr Gly Thr Lys Asn Ser Phe
  1               5                  10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Tyr Leu Ser Lys Gly Arg Leu Val Phe Ala Leu Gly
  1               5                  10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asn Asp Gly Lys Trp His Thr Val Val Phe Gly His
  1               5                  10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Asn Ser Thr Ile Ser Ile Arg Ala Pro Val Tyr
  1               5                  10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Leu Phe Leu Ala His Gly Arg Leu Val Phe Met
  1               5                  10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

His Pro Asp Asp Phe Val Phe Tyr Val Gly Gly Tyr
  1               5                  10
```

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Trp Leu Tyr Val Asp Asp Gln Leu Gln Leu Val Lys
 1               5                  10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Gln Ser Arg Gln His Ser Arg Ala Gly Gln Trp
 1               5                  10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Gly Gln Trp His Arg Val Ser Val Arg Trp Gly
 1               5                  10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Val Arg Trp Gly Met Gln Gln Ile Gln Leu Val Val
 1               5                  10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Thr Trp Ser Gln Lys Ala Leu His His Arg Val Pro
 1               5                  10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 18

Asp Gly Arg Trp His Arg Val Ala Val Ile Met Gly
 1               5                  10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Pro Val Asn Val Thr Ala Ser Val Gln Ile Gln
 1               5                  10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Pro Arg Leu Gln Phe Ser Leu Asp Ile Gln Thr
 1               5                  10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Asn Arg Leu His Leu Ser Met Leu Val Arg Pro
 1               5                  10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Ala Ser Ile Lys Val Ala Val Ser Ala Asp Arg
 1               5                  10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Ser Phe Gly Phe Gln Thr Phe Gln Pro Ser Gly
 1               5                  10

<210> SEQ ID NO 24
<211> LENGTH: 12
```

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Phe Lys Leu Pro Gln Glu Leu Leu Lys Pro Arg Ser
  1               5                  10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Lys Asn Ser Phe Met Ala Leu Tyr Leu Ser Lys Gly
  1               5                  10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Leu His Val Phe Tyr Asp Phe Gly Phe Ser Asn Gly
  1               5                  10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Val Leu Val Arg Val Glu Arg Ala Thr Val Phe Ser
  1               5                  10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Phe Leu Pro Leu Ala Leu Pro Asp Val Ala Pro Ile
  1               5                  10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Pro Leu Pro Ser Tyr Leu Gln Phe Val Gly Ile
```

```
              1               5                  10
```

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Val Gln Ile Gln Gly Ala Val Gly Met Arg Gly
 1               5                  10

<210> SEQ ID NO 31
<211> LENGTH: 416
<212> TYPE: PRT
<213> ORGANISM: Homo sapiens

<400> SEQUENCE: 31

Val Val Arg Leu Asn Asp Thr Val Gly Val Thr Lys Lys Cys Ser Glu
 1               5                  10                  15

Asp Trp Lys Leu Val Arg Ser Ala Ser Phe Ser Arg Gly Gly Gln Leu
                20                  25                  30

Ser Phe Thr Asp Leu Gly Leu Pro Pro Thr Asp His Leu Gln Ala Ser
            35                  40                  45

Phe Gly Phe Gln Thr Phe Gln Pro Ser Gly Ile Leu Leu Asp His Gln
        50                  55                  60

Thr Trp Thr Arg Asn Leu Gln Val Thr Leu Glu Asp Gly Tyr Ile Glu
 65                 70                  75                  80

Leu Ser Thr Ser Asp Ser Gly Gly Pro Ile Phe Lys Ser Pro Gln Thr
                85                  90                  95

Tyr Met Asp Gly Leu Leu His Tyr Val Ser Val Ile Ser Asp Asn Ser
            100                 105                 110

Gly Leu Arg Leu Leu Ile Asp Asp Gln Leu Leu Arg Asn Ser Lys Arg
        115                 120                 125

Leu Lys His Ile Ser Ser Arg Gln Ser Leu Arg Leu Gly Gly Ser
130                 135                 140

Asn Phe Glu Gly Cys Ile Ser Asn Val Phe Val Gln Arg Leu Ser Leu
145                 150                 155                 160

Ser Pro Glu Val Leu Asp Leu Thr Ser Asn Ser Leu Lys Arg Asp Val
                165                 170                 175

Ser Leu Gly Gly Cys Ser Leu Asn Lys Pro Pro Phe Leu Met Leu Leu
            180                 185                 190

Lys Gly Ser Thr Arg Phe Asn Lys Thr Lys Thr Phe Arg Ile Asn Gln
        195                 200                 205

Leu Leu Gln Asp Thr Pro Val Ala Ser Pro Arg Ser Val Lys Val Trp
    210                 215                 220

Gln Asp Ala Cys Ser Pro Leu Pro Lys Thr Gln Ala Asn His Gly Ala
225                 230                 235                 240

Leu Gln Phe Gly Asp Ile Pro Thr Ser His Leu Leu Phe Lys Leu Pro
                245                 250                 255

Gln Glu Leu Leu Lys Pro Arg Ser Gln Phe Ala Val Asp Met Gln Thr
            260                 265                 270

Thr Ser Ser Arg Gly Leu Val Phe His Thr Gly Thr Lys Asn Ser Phe
        275                 280                 285

Met Ala Leu Tyr Leu Ser Lys Gly Arg Leu Val Phe Ala Leu Gly Thr

```
        290                 295                 300
Asp Gly Lys Lys Leu Arg Ile Lys Ser Lys Glu Lys Cys Asn Asp Gly
305                 310                 315                 320

Lys Trp His Thr Val Val Phe Gly His Asp Gly Glu Lys Gly Arg Leu
                325                 330                 335

Val Val Asp Gly Leu Arg Ala Arg Glu Gly Ser Leu Pro Gly Asn Ser
            340                 345                 350

Thr Ile Ser Ile Arg Ala Pro Val Tyr Leu Gly Ser Pro Ser Gly
        355                 360                 365

Lys Pro Lys Ser Leu Pro Thr Asn Ser Phe Val Gly Cys Leu Lys Asn
370                 375                 380

Phe Gln Leu Asp Ser Lys Pro Leu Tyr Thr Pro Ser Ser Ser Phe Gly
385                 390                 395                 400

Val Ser Ser Cys Leu Gly Gly Pro Leu Glu Lys Gly Ile Tyr Phe Ser
                405                 410                 415

<210> SEQ ID NO 32
<211> LENGTH: 964
<212> TYPE: PRT
<213> ORGANISM: Mus musculus

<400> SEQUENCE: 32

Thr Ser Ile Ser Leu Tyr Met Lys Pro Pro Lys Pro Gln Thr Thr
1               5                   10                  15

Gly Ala Trp Val Ala Asp Gln Phe Val Leu Tyr Leu Gly Ser Lys Asn
            20                  25                  30

Ala Lys Lys Glu Tyr Met Gly Leu Ala Ile Lys Asn Asp Asn Leu Val
        35                  40                  45

Tyr Val Tyr Asn Leu Gly Met Lys Asp Val Glu Ile Leu Leu Asp Ser
    50                  55                  60

Lys Pro Val Ser Ser Trp Pro Ala Tyr Phe Ser Ile Val Lys Ile Glu
65                  70                  75                  80

Arg Val Gly Lys His Gly Lys Val Phe Leu Thr Val Pro Ser Ser Ser
                85                  90                  95

Ser Thr Ala Glu Glu Lys Phe Ile Lys Lys Gly Glu Phe Ala Gly Asp
            100                 105                 110

Asp Ser Leu Leu Asp Leu Thr Pro Glu Asp Thr Val Phe Tyr Val Gly
        115                 120                 125

Gly Val Pro Ala Asn Phe Lys Leu Pro Ala Ser Leu Asn Leu Pro Ser
    130                 135                 140

Tyr Ser Gly Cys Leu Glu Leu Ala Thr Leu Asn Asn Asp Val Ile Ser
145                 150                 155                 160

Leu Tyr Asn Phe Lys His Ile Tyr Asn Met Asp Pro Ser Lys Ser Val
                165                 170                 175

Pro Cys Ala Arg Asp Lys Leu Ala Phe Thr Gln Ser Arg Ala Ala Ser
            180                 185                 190

Tyr Phe Phe Asp Gly Ser Ser Tyr Ala Val Val Arg Asp Ile Thr Arg
        195                 200                 205

Arg Gly Lys Phe Gly Gln Val Thr Arg Phe Asp Ile Glu Ile Arg Thr
    210                 215                 220

Pro Ala Asp Asn Gly Leu Val Leu Leu Met Val Asn Gly Ser Met Phe
225                 230                 235                 240

Phe Ser Leu Glu Met Arg Asn Gly Tyr Leu His Val Phe Tyr Asp Phe
                245                 250                 255
```

```
Gly Phe Ser Asn Gly Pro Val His Leu Glu Asp Thr Leu Lys Lys Ala
            260                 265                 270
Gln Ile Asn Asp Ala Lys Tyr Arg Glu Ile Ser Ile Ile Tyr His Asn
        275                 280                 285
Asp Lys Lys Met Ile Leu Val Val Asp Arg Arg His Val Lys Ser Thr
    290                 295                 300
Asp Asn Glu Lys Lys Lys Ile Pro Phe Thr Asp Ile Tyr Ile Gly Gly
305                 310                 315                 320
Ala Pro Gln Glu Val Leu Gln Ser Arg Thr Leu Arg Ala His Leu Pro
                325                 330                 335
Leu Asp Ile Asn Phe Arg Gly Cys Met Lys Gly Ile Gln Phe Gln Lys
            340                 345                 350
Lys Asp Phe Asn Leu Leu Glu Gln Thr Glu Thr Leu Gly Val Gly Tyr
        355                 360                 365
Gly Cys Pro Glu Asp Ser Leu Ile Ser Arg Arg Ala Tyr Phe Asn Gly
    370                 375                 380
Gln Ser Phe Ile Ala Ser Ile Gln Lys Ile Ser Phe Phe Asp Gly Phe
385                 390                 395                 400
Glu Gly Gly Phe Asn Phe Arg Thr Leu Gln Pro Asn Gly Leu Leu Phe
                405                 410                 415
Tyr Tyr Thr Ser Gly Ser Asp Val Phe Ser Ile Ser Leu Asp Asn Gly
            420                 425                 430
Thr Val Val Met Asp Val Lys Gly Ile Lys Val Met Ser Thr Asp Lys
        435                 440                 445
Gln Tyr His Asp Gly Leu Pro His Phe Val Val Thr Ser Ile Ser Asp
    450                 455                 460
Thr Arg Tyr Glu Leu Val Val Asp Lys Ser Arg Leu Arg Gly Lys Asn
465                 470                 475                 480
Pro Thr Lys Gly Lys Ala Glu Gln Thr Gln Thr Thr Glu Lys Lys Phe
                485                 490                 495
Tyr Phe Gly Gly Ser Pro Ile Ser Pro Gln Tyr Ala Asn Phe Thr Gly
            500                 505                 510
Cys Ile Ser Asn Ala Tyr Phe Thr Arg Leu Asp Arg Asp Val Glu Val
        515                 520                 525
Glu Ala Phe Gln Arg Tyr Ser Glu Lys Val His Thr Ser Leu Tyr Glu
    530                 535                 540
Cys Pro Ile Glu Ser Ser Pro Leu Phe Leu Leu His Lys Gly Lys Lys
545                 550                 555                 560
Asn Ser Ser Lys Pro Lys Thr Asn Lys Gln Gly Glu Lys Ser Lys Asp
                565                 570                 575
Ala Pro Ser Trp Asp Pro Ile Gly Leu Lys Phe Leu Glu Gln Lys Ala
            580                 585                 590
Pro Arg Asp Ser His Cys His Leu Phe Ser Ser Pro Arg Ala Ile Glu
        595                 600                 605
His Ala Tyr Gln Tyr Gly Gly Thr Ala Asn Ser Arg Gln Glu Phe Glu
    610                 615                 620
His Glu Gln Gly Asp Phe Gly Glu Lys Ser Gln Phe Ser Ile Arg Leu
625                 630                 635                 640
Lys Thr Arg Ser Ser His Gly Met Ile Phe Tyr Val Ser Asp Gln Glu
                645                 650                 655
Glu Asn Asp Phe Met Thr Leu Phe Leu Ala His Gly Arg Leu Val Phe
            660                 665                 670
Met Phe Asn Val Gly His Lys Lys Leu Lys Ile Arg Ser Gln Glu Lys
```

```
                    675                 680                 685
Tyr Asn Asp Gly Leu Trp His Asp Val Ile Phe Ile Arg Glu Lys Ser
    690                 695                 700

Ser Gly Arg Leu Val Ile Asp Gly Leu Arg Val Leu Glu Glu Arg Leu
705                 710                 715                 720

Pro Pro Ser Gly Ala Ala Trp Lys Ile Lys Gly Pro Ile Tyr Leu Gly
                725                 730                 735

Gly Val Ala Pro Gly Arg Ala Val Lys Asn Val Gln Ile Thr Ser Val
            740                 745                 750

Tyr Ser Phe Ser Gly Cys Leu Gly Asn Leu Gln Leu Asn Gly Ala Ser
        755                 760                 765

Ile Thr Ser Ala Ser Gln Thr Phe Ser Val Thr Pro Cys Phe Glu Gly
770                 775                 780

Pro Met Glu Thr Gly Thr Tyr Phe Ser Thr Glu Gly Gly Tyr Val Val
785                 790                 795                 800

Leu Asp Glu Ser Phe Asn Ile Gly Leu Lys Phe Glu Ile Ala Phe Glu
                805                 810                 815

Val Arg Pro Arg Ser Ser Ser Gly Thr Leu Val His Gly His Ser Val
            820                 825                 830

Asn Gly Glu Tyr Leu Asn Val His Met Arg Asn Gly Gln Val Ile Val
        835                 840                 845

Lys Val Asn Asn Gly Val Arg Asp Phe Ser Thr Ser Val Thr Pro Lys
850                 855                 860

Gln Asn Leu Cys Asp Gly Arg Trp His Arg Ile Thr Val Ile Arg Asp
865                 870                 875                 880

Ser Asn Val Val Gln Leu Asp Val Asp Ser Glu Val Asn His Val Val
                885                 890                 895

Gly Pro Leu Asn Pro Lys Pro Val Asp His Arg Glu Pro Val Phe Val
            900                 905                 910

Gly Gly Val Pro Glu Ser Leu Leu Thr Pro Arg Leu Ala Pro Ser Lys
        915                 920                 925

Pro Phe Thr Gly Cys Ile Arg His Phe Val Ile Asp Ser Arg Pro Val
930                 935                 940

Ser Phe Ser Lys Ala Ala Leu Val Ser Gly Ala Val Ser Ile Asn Ser
945                 950                 955                 960

Cys Pro Thr Ala

<210> SEQ ID NO 33
<211> LENGTH: 956
<212> TYPE: PRT
<213> ORGANISM: Mus musculus

<400> SEQUENCE: 33

Thr Ala Leu Lys Phe His Ile Gln Ser Pro Val Pro Ala Pro Glu Pro
1               5                   10                  15

Gly Lys Asn Thr Gly Asp His Phe Val Leu Tyr Met Gly Ser Arg Gln
            20                  25                  30

Ala Thr Gly Asp Tyr Met Gly Val Ser Leu Arg Asn Gln Lys Val His
        35                  40                  45

Trp Val Tyr Arg Leu Gly Lys Ala Gly Pro Thr Thr Leu Ser Ile Asp
    50                  55                  60

Glu Asn Ile Gly Glu Gln Phe Ala Ala Val Ser Ile Asp Arg Thr Leu
65                  70                  75                  80

Gln Phe Gly His Met Ser Val Thr Val Glu Lys Gln Met Val His Glu
```

-continued

```
                        85                   90                    95
Ile Lys Gly Asp Thr Val Ala Pro Gly Ser Glu Gly Leu Leu Asn Leu
                100                 105                 110

His Pro Asp Asp Phe Val Phe Tyr Val Gly Gly Tyr Pro Ser Asn Phe
                115                 120                 125

Thr Pro Pro Glu Pro Leu Arg Phe Pro Gly Tyr Leu Gly Cys Ile Glu
            130                 135                 140

Met Glu Thr Leu Asn Glu Val Val Ser Leu Tyr Asn Phe Glu Gln
145                 150                 155                 160

Thr Phe Met Leu Asp Thr Ala Val Asp Lys Pro Cys Ala Arg Ser Lys
                165                 170                 175

Ala Thr Gly Asp Pro Trp Leu Thr Asp Gly Ser Tyr Leu Asp Gly Ser
                180                 185                 190

Gly Phe Ala Arg Ile Ser Phe Glu Lys Gln Phe Ser Asn Thr Lys Arg
            195                 200                 205

Phe Asp Gln Glu Leu Arg Leu Val Ser Tyr Asn Gly Ile Ile Phe Phe
        210                 215                 220

Leu Lys Gln Glu Ser Gln Phe Leu Cys Leu Ala Val Gln Glu Gly Thr
225                 230                 235                 240

Leu Val Leu Phe Tyr Asp Phe Gly Ser Gly Leu Lys Lys Ala Asp Pro
                245                 250                 255

Leu Gln Pro Pro Gln Ala Leu Thr Ala Ala Ser Lys Ala Ile Gln Val
            260                 265                 270

Phe Leu Leu Ala Gly Asn Arg Lys Arg Val Leu Val Arg Val Glu Arg
        275                 280                 285

Ala Thr Val Phe Ser Val Asp Gln Asp Asn Met Leu Glu Met Ala Asp
        290                 295                 300

Ala Tyr Tyr Leu Gly Gly Val Pro Pro Glu Gln Leu Pro Leu Ser Leu
305                 310                 315                 320

Arg Gln Leu Phe Pro Ser Gly Gly Ser Val Arg Gly Cys Ile Lys Gly
                325                 330                 335

Ile Lys Ala Leu Gly Lys Tyr Val Asp Leu Lys Arg Leu Asn Thr Thr
            340                 345                 350

Gly Ile Ser Phe Gly Cys Thr Ala Asp Leu Leu Val Gly Arg Thr Met
        355                 360                 365

Thr Phe His Gly His Gly Phe Leu Pro Leu Ala Leu Pro Asn Val Ala
        370                 375                 380

Pro Ile Thr Glu Val Val Tyr Ser Gly Phe Gly Phe Arg Gly Thr Gln
385                 390                 395                 400

Asp Asn Asn Leu Leu Tyr Tyr Arg Thr Ser Pro Asp Gly Pro Tyr Gln
                405                 410                 415

Val Ser Leu Arg Glu Gly His Val Thr Leu Arg Phe Met Asn Gln Glu
            420                 425                 430

Val Glu Thr Gln Arg Val Phe Ala Asp Gly Ala Pro His Tyr Val Ala
        435                 440                 445

Phe Tyr Ser Asn Val Thr Gly Val Trp Leu Tyr Val Asp Asp Gln Leu
        450                 455                 460

Gln Leu Val Lys Ser His Glu Arg Thr Thr Pro Met Leu Gln Leu Gln
465                 470                 475                 480

Pro Glu Glu Pro Ser Arg Leu Leu Leu Gly Gly Leu Pro Val Ser Gly
                485                 490                 495

Thr Phe His Asn Phe Ser Gly Cys Ile Ser Asn Val Phe Val Gln Arg
            500                 505                 510
```

-continued

```
Leu Arg Gly Pro Gln Arg Val Phe Asp Leu His Gln Asn Met Gly Ser
        515                 520                 525
Val Asn Val Ser Val Gly Cys Thr Pro Ala Gln Leu Ile Glu Thr Ser
    530                 535                 540
Arg Ala Thr Ala Gln Lys Val Ser Arg Arg Ser Arg Gln Pro Ser Gln
545                 550                 555                 560
Asp Leu Ala Cys Thr Thr Pro Trp Leu Pro Gly Thr Ile Gln Asp Ala
                565                 570                 575
Tyr Gln Phe Gly Gly Pro Leu Pro Ser Tyr Leu Gln Phe Val Gly Ile
            580                 585                 590
Ser Pro Ser His Arg Asn Arg Leu His Leu Ser Met Leu Val Arg Pro
        595                 600                 605
His Ala Ala Ser Gln Gly Leu Leu Ser Thr Ala Pro Met Ser Gly
    610                 615                 620
Arg Ser Pro Ser Leu Val Leu Phe Leu Asn His Gly His Phe Val Ala
625                 630                 635                 640
Gln Thr Glu Gly Pro Gly Pro Arg Leu Gln Val Gln Ser Arg Gln His
                645                 650                 655
Ser Arg Ala Gly Gln Trp His Arg Val Ser Val Arg Trp Gly Met Gln
            660                 665                 670
Gln Ile Gln Leu Val Val Asp Gly Ser Gln Thr Trp Ser Gln Lys Ala
        675                 680                 685
Leu His His Arg Val Pro Arg Ala Glu Arg Pro Gln Pro Tyr Thr Leu
    690                 695                 700
Ser Val Gly Gly Leu Pro Ala Ser Ser Tyr Ser Ser Lys Leu Pro Val
705                 710                 715                 720
Ser Val Gly Phe Ser Gly Cys Leu Lys Lys Leu Gln Leu Asp Lys Gln
                725                 730                 735
Pro Leu Arg Thr Pro Thr Gln Met Val Gly Val Thr Pro Cys Val Ser
            740                 745                 750
Gly Pro Leu Glu Asp Gly Leu Phe Phe Pro Gly Ser Glu Gly Val Val
        755                 760                 765
Thr Leu Glu Leu Pro Lys Ala Lys Met Pro Tyr Val Ser Leu Glu Leu
    770                 775                 780
Glu Met Arg Pro Leu Ala Ala Ala Gly Leu Ile Phe His Leu Gly Gln
785                 790                 795                 800
Ala Leu Ala Thr Pro Tyr Met Gln Leu Lys Val Leu Thr Glu Gln Val
                805                 810                 815
Leu Leu Gln Ala Asn Asp Gly Ala Gly Glu Phe Ser Thr Trp Val Thr
            820                 825                 830
Tyr Pro Lys Leu Cys Asp Gly Arg Trp His Arg Val Ala Val Ile Met
        835                 840                 845
Gly Arg Asp Thr Leu Arg Leu Glu Val Asp Thr Gln Ser Asn His Thr
    850                 855                 860
Thr Gly Arg Leu Pro Glu Ser Leu Ala Gly Ser Pro Ala Leu Leu His
865                 870                 875                 880
Leu Gly Ser Leu Pro Lys Ser Ser Thr Ala Arg Pro Glu Leu Pro Ala
                885                 890                 895
Tyr Arg Gly Cys Leu Arg Lys Leu Leu Ile Asn Gly Ala Pro Val Asn
            900                 905                 910
Val Thr Ala Ser Val Gln Ile Gln Gly Ala Val Gly Met Arg Gly Cys
        915                 920                 925
```

```
Pro Ser Gly Thr Leu Ala Leu Ser Lys Gln Gly Lys Ala Leu Thr Gln
    930                 935                 940

Arg His Ala Lys Pro Ser Val Ser Pro Leu Leu His
945                 950                 955

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Thr Arg Ile Ser Leu Gln Val Gln Leu Arg Lys Arg
  1               5                  10

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Lys Ile Ile Ile Tyr Ala Val Gln Phe Val Gln Arg
  1               5                  10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Leu Ala Phe Val Leu Arg Gly Lys Ser Leu Tyr
  1               5                  10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Met Phe Val Leu Arg Gly His Ala Leu Phe Leu Thr
  1               5                  10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Trp Arg Val Ser Val Arg His Trp Gln Gly Ala
  1               5                  10

<210> SEQ ID NO 39
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Met Ile Val Ala Val Arg His Trp Arg Gly Asp
 1               5                  10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Thr Leu Phe Phe Met Arg Leu Val His Ala Leu Gly
 1               5                  10

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Leu Pro Phe Phe Asp
 1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Gly Gln Trp His Arg Val
 1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Gln Trp His Arg Val Ser
 1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Trp His Arg Val Ser Val
```

```
                  1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Trp His Arg Val Ser Val Arg
  1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

His Arg Val Ser Val Arg Trp
  1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Val Ser Val Arg Trp Gly
  1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asp Gly Arg Trp His Arg Val
  1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Arg Trp His Arg Val Ala
  1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
```

-continued

```
      peptide

<400> SEQUENCE: 50

Arg Trp His Arg Val Ala Val
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Trp His Arg Val Ala Val Ile
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

His Arg Val Ala Val Ile Met
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Arg Val Ala Val Ile Met Gly
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Thr Leu Phe Leu Ala His Gly
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Phe Leu Ala His Gly Arg
1               5

<210> SEQ ID NO 56
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Phe Leu Ala His Gly Arg Leu
 1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Leu Ala His Gly Arg Leu Val
 1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ala His Gly Arg Leu Val Phe
 1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

His Gly Arg Leu Val Phe Met
 1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Leu Ala Phe Val Leu Arg
 1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61
```

```
Leu Ala Phe Val Leu Arg Gly
  1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ala Phe Val Leu Arg Gly Lys
  1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Phe Val Leu Arg Gly Lys Ser
  1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Val Leu Arg Gly Lys Ser Leu
  1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Leu Arg Gly Lys Ser Leu Tyr
  1               5

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Arg Lys Arg Leu Gln Val Gln Tyr
  1               5

<210> SEQ ID NO 67
<211> LENGTH: 8
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 67

Lys Arg Leu Gln Val Gln Leu Tyr
 1               5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Leu Gln Val Gln Leu Ser Tyr
 1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Leu Gln Val Gln Leu Ser Ile Tyr
 1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Val Gln Leu Ser Ile Arg Tyr
 1               5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Val Gln Leu Ser Ile Arg Thr Tyr
 1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Arg Gln Val Phe Gln Val Ala
 1               5

-continued

```
<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Val Phe Gln Val Ala Tyr
 1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Val Phe Gln Val Ala Tyr Ile
 1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Phe Gln Val Ala Tyr Ile Ile
 1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gln Val Ala Tyr Ile Ile Ile
 1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Val Ala Tyr Ile Ile Ile Lys
 1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78
```

```
Ala Tyr Ile Ile Ile Lys Ala
 1               5

<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Tyr Leu Ser Lys Gly Arg Leu Tyr
 1               5

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Leu Ser Lys Gly Arg Leu Val Tyr
 1               5

<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ser Lys Gly Arg Leu Val Phe Tyr
 1               5

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Lys Gly Arg Leu Val Phe Ala Tyr
 1               5

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Arg Leu Val Phe Ala Leu Tyr
 1               5

<210> SEQ ID NO 84
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 84

Arg Leu Val Phe Ala Leu Gly Tyr
 1               5

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Thr Leu Phe Leu Ala His Gly Tyr
 1               5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Leu Phe Leu Ala His Gly Arg Tyr
 1               5

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Phe Leu Ala His Gly Arg Leu Tyr
 1               5

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Leu Ala His Gly Arg Leu Val Tyr
 1               5

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ala His Gly Arg Leu Val Phe Tyr
 1               5
```

```
<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

His Gly Arg Leu Val Phe Met Tyr
 1               5

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Gly Gln Trp His Arg Val Tyr
 1               5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Gln Trp His Arg Val Ser Tyr
 1               5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Trp His Arg Val Ser Val Tyr
 1               5

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Trp His Arg Val Ser Val Arg Tyr
 1               5

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 95

His Arg Val Ser Val Arg Trp Tyr
 1               5

<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Val Ser Val Arg Trp Gly Tyr
 1               5

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Asp Gly Arg Trp His Arg Val Tyr
 1               5

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Arg Trp His Arg Val Ala Tyr
 1               5

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Arg Trp His Arg Val Ala Val Tyr
 1               5

<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Trp His Arg Val Ala Val Ile Tyr
 1               5

<210> SEQ ID NO 101
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 101

His Arg Val Ala Val Ile Met Tyr
 1               5

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Arg Val Ala Val Ile Met Gly Tyr
 1               5

<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Leu Ala Phe Val Leu Arg Tyr
 1               5

<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Leu Ala Phe Val Leu Arg Gly Tyr
 1               5

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ala Phe Val Leu Arg Gly Lys Tyr
 1               5

<210> SEQ ID NO 106
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Phe Val Leu Arg Gly Lys Ser Tyr
 1               5
```

```
<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Val Leu Arg Gly Lys Ser Leu Tyr
 1               5

<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Leu Arg Gly Lys Ser Leu Tyr Tyr
 1               5
```

SMALL PEPTIDES FOR THE TREATMENT OF ALZHEIMER'S DISEASE AND OTHER BETA-AMYLOID PROTEIN FIBRILLOGENESIS DISORDERS

This application is a continuation-in-part of U.S. patent application Ser. No. 09/962,955 filed Sep. 24, 2001 now U.S. Pat. No. 6,933,280 which is a continuation-in-part of U.S. patent application Ser. No. 09/938,275 filed Aug. 22, 2001 which is a continuation of U.S. patent application Ser. No. 08/947,057 filed Oct. 8, 1997 now abandoned. This application also claims priority to U.S. Provisional Application 60/461,655 filed Apr. 8, 2003.

This invention was made with government support under 1R43AG17787 awarded by the National Institute on Aging. The Government has certain rights in the invention.

TECHNICAL FIELD

This invention relates to the use of small (7 to 12 mer) laminin peptides and laminin derivatives for the treatment of Alzheimer's disease and other beta-amyloid protein fibrillogenesis disorders.

BACKGROUND OF THE INVENTION

Additional background for therapeutic use of laminin, and peptide fragments of laminin, in the treatment of Alzheimer's disease and other amyloidoses can be found in U.S. patent application Ser. No. 09/938,275 filed Aug. 22, 2001, and in U.S. patent application Ser. No. 09/962,955 filed Sep. 24, 2001, the text and drawings of each of which are hereby incorporated by reference into the present application as if fully set forth herein.

Beta-Amyloid Protein as a Therapeutic Target for Alzheimer's Disease

Alzheimer's disease (AD) is characterized by the deposition and accumulation of a 39-43 amino acid peptide termed the beta-amyloid protein, Aβ or β/A4 (Glenner and Wong, *Biochem. Biophys. Res. Comm.* 120:885-890. 1984; Masters et al, *Proc. Nat. Acad. Sci. U.S.A.* 82:4245-4249, 1985; Husby et al, *Bull. WHO* 71:105-108, 1993). Aβ is derived from larger precursor proteins termed beta amyloid precursor proteins (or APPs) of which there are several alternatively spliced variants. The most abundant forms of the APPs include proteins consisting of 695, 751 and 770 amino acids (Kitaguchi et al, *Nature* 331:530-532, 1988; Ponte et al, *Nature* 331:525-527, 1988; Tanzi et al, *Nature* 331:528-530, 1988). The small Aβ peptide is a major component that makes up the core of amyloid deposits called "plaques" in the brains of patients with AD. In addition, AD is characterized by the presence of numerous neurofibrillary "tangles", consisting of paired helical filaments which abnormally accumulate in the neuronal cytoplasm (Grundke-Iqbal et al *Proc. Natl. Acad. Sci. U.S.A.* 83:4913-4917, 1986; Kosik et al, *Proc. Natl. Acad. Sci. U.S.A.* 83:4044-4048, 1986; Lee et al, *Science* 251:675-678, 1991). The other major type of lesion found in AD brain is the accumulation of amyloid in the walls of blood vessels, both within the brain parenchyma and meningeal vessels that lie outside the brain. The amyloid deposits localized to the walls of blood vessels are referred to as cerebrovascular amyloid or congophilic angiopathy (Mandybur, *J. Neuropath. Exp. Neurol.* 45:79-90, 1986; Pardridge et al, *J. Neurochem.* 49:1394-1401, 1987). The pathological hallmarks of AD therefore are the presence of "plaques", "tangles", and cerebrovascular amyloid deposits.

For many years there has been an ongoing scientific debate as to the importance of "amyloid" in AD and whether the "plaques" and "tangles" characteristic of this disease, were a cause or merely the consequences of the disease. Recent studies indicate that amyloid is indeed a causative factor for AD and should not be regarded merely as a consequence. The Alzheimer's Aβ protein in cell culture has been shown to cause degeneration of nerve cells within a short time period (Pike et al, *Br. Res.* 563:311-314, 1991; *J. Neurochem.* 64:253-265, 1995). Studies suggest that it is the fibrillar structure, characteristic of all amyloids, that is mainly responsible for the neurologic effects. Aβ has also been found to be neurologic in slice cultures of hippocampus (Hadrian et al, *Neurobiol. Aging* 16:779-789, 1995) and induces nerve cell death in transgenic mice (Games et al, *Nature* 373:523-527, 1995; Hsiao et al, *Science* 274:99-102, 1996). Injection of Aβ into rat brain also causes memory impairment and neuronal dysfunction (Flood et al, *Proc. Natl. Acad. Sci. U.S.A.* 88:3363-3366, 1991; *Br. Res.* 663: 271-276, 1994). Convincing evidence that Aβ amyloid is directly involved in the pathogenesis of AD comes from genetic studies. It was discovered that the increased production of Aβ could result from mutations in the gene encoding, its precursor, APP (Van Broeckhoven et al, *Science* 248: 1120-1122, 1990; Murrell et al, *Science* 254:97-99, 1991; Haass et al, *Nature Med.* 1:1291-1296, 1995). The identification of mutations in the APP gene which causes early onset familial AD is a strong argument that Aβ and amyloid are central to the pathogenetic process underlying this disease. Four reported disease-causing mutations have now been discovered which demonstrate the importance of Aβ in causing familial AD (reviewed in Hardy, *Nature Gen.* 1:233-234, 1992). Lastly, recent studies suggest that a reduction in amyloid plaque load in APP transgenic mice lead to improvements in behavioral impairment and memory loss (Chen et al, *Nature* 408:978-982, 2000; Janus et al, *Nature* 408:979-982, 2000; Morgan et al, *Nature* 408:982-985, 2000). This is the strongest argument to date that implicates that reduction of Aβ amyloid load in brain should be a central target for the development of new and effective treatments of AD and related disorders.

Alzheimer's Disease and the Aging Population

Alzheimer's disease is a leading cause of dementia in the elderly, affecting 5-10% of the population over the age of 65 years (Jorm, *A Guide to Understanding of Alzheimer's Disease and Related Disorders*, New York University Press, New York, 1987). In AD, the parts of the brain essential for cognitive processes such as memory, attention, language, and reasoning degenerate. In some inherited forms of AD, onset is in middle age, but more commonly, symptoms appear from the mid-60's onward. AD today affects 4-5 million Americans, with slightly more than half of these people receiving care in many different health care institutions. The prevalence of AD and other dementias doubles every 5 years beyond the age of 65, and recent studies indicate that nearly 50% of all people age 85 and older have symptoms of AD (NIH Progress Report on AD, National Institute on Aging, 2000). Thirty-three million people of the total population of the United States are age 65 and older, and this will climb to 51 million people by the year 2025 (NIH Progress Report on AD, National Institute on Aging, 2000). The annual economic toll of AD in the United States in terms of health care expenses and lost wages of both patients and their caregivers is estimated at $80 to $100 billion (NIH Progress Report on AD, National Institute on Aging, 2000).

Laminin and its Presence in Alzheimer's Disease

Laminin is a large glycoprotein complex of 850 kDa which normally resides on the basement membrane and is produced by a variety of cells including embryonic, epithelial and tumor cells (Foidart et al *Lab. Invest.* 42:336-342, 1980; Timpl, *Eur. J. Biochem.* 180:487-502, 1989). Laminin interacts with various extracellular matrix components including heparan sulfate proteoglycans (Riopelle and Dow, *Br. Res.* 525:92-100, 1990; Battaglia et al, *Eur. J. Biochem.* 208:359-366, 1992), heparin (Sakashita et al, *FEBS Letts.* 116:243-246, 1980; Del-Rosso et al, *Biochem. J.* 199:699-704, 1981; Skubitz et al, *J. Biol. Chem.* 263:4861-4868, 1988) and type IV collagen (Terranova et al, *Cell* 22:719-726, 1980; Rao et al, *Biochem. Biophys. Res. Comm.* 128: 45-52, 1985; Charonis et al, *J. Cell Biol.* 100:1848-1853, 1985; Laurie et al, *J. Mol. Biol.* 189:205-216, 1986). Laminin is composed of three distinct polypeptide chains, A1, B1 and B2 (also referred to as alpha-1, β1 and gamma-1, respectively), joined in a multidomain cruciform structure possessing three short arms and one long arm (Burgèson et al, *Matrix Biol.* 14:209-211, 1994). Studies involving in vitro self-assembly and the analysis of cell-formed basement membranes have shown that the three short arms interact to form a polymer which is a part of a basement membrane network (Yurchenco et al, *J. Biol. Chem.* 260:7636-7644, 1985; *J. Cell Biol.* 117:1119-1133, 1992; Yurchenco and Cheng, *J. Biol. Chem.* 268:17286-17299, 1993). In addition to its role in basement membrane formation (Kleinman et al, *Biochem.* 22:4969-4974, 1983), laminin also plays important roles in a number of fundamental biological processes including promotion of neurite outgrowth (Lander et al, *Proc. Natl. Acad. Sci. U.S.A.* 82:2183-2187, 1985; Bronner-Fraser and Lallier, *J. Cell Biol.* 106:1321-1329, 1988) and cell adhesion (Engvall et al, *J. Cell Biol.* 103:2457-2465, 1986). Injury to adult brain also induces laminin production by astrocytes (Liesi et al, *EMBO J.* 3:683-686, 1984) indicating its role in repair processes. In AD and Down's syndrome, laminin is believed to be present in the vicinity of Aβ amyloid plaques (Perlmutter and Chui, *Br. Res. Bull.* 24:677-686, 1990; Murtomaki et al, *J. Neurosc. Res.* 32:261-273, 1992; Perlmutter et al, *Micro. Res. Tech.* 28:204-215, 1994). Previous studies have also indicated that the various isoforms of APP of AD bind laminin (Narindrasorasak et al, *Lab. Invest.* 67:643-652, 1992) and other basement membrane components, including perlecan (Narindrasorasak et al, *J. Biol. Chem.* 266:12878-12883, 1991), fibronectin and type IV collagen (Narindrasorasak et al, *J. Biol. Chem.* 270:20583-20590, 1995).

DISCLOSURE OF THE INVENTION

This application is a continuation-in-part of U.S. patent application Ser. No. 09/962,955 filed Sep. 24, 2001, which is a continuation-in-part of U.S. patent application Ser. No. 09/938,275 filed Aug. 22, 2001, the text and drawings of each of which are hereby incorporated by reference into the present application as if fully set forth herein.

Laminin-derived peptides are disclosed which demonstrate greater efficacy in inhibiting and/or disrupting amyloid fibrils than that of iAβ5, a known peptide currently under development as a beta-amyloid disease therapeutic.

Methods are disclosed herein for the treatment and diagnosis of Alzheimer's disease and other disorders that involve the accumulation and persistence of beta-amyloid protein (Aβ), sometimes referred to herein as "beta-amyloid protein fibrillogenesis disorders". Methods are disclosed for treating Alzheimer's disease and other Aβ disorders, comprising administering to a subject or patient a therapeutically effective dose of at least one laminin globular domain-derived L- or D-form peptide, such as small 7-12 mer peptides disclosed herein, or an analog or a derivative thereof. In one exemplary embodiment, the laminin peptide which is a potent Aβ amyloid inhibitory agent is selected from the group consisting of AG73 (SEQ ID NO:1), C-16 (SEQ ID NO:2), A-13 (SEQ ID NO:3), HA3G47 (SEQ ID NO:4), HA3G58 (SEQ ID NO:5), HA3G67 (SEQ ID NO:6), HA3G74 (SEQ ID NO:7), HA3G76 (SEQ ID NO:8), HA3G79 (SEQ ID NO:9), HA3G83 (SEQ ID NO:10), A4G82 (SEQ ID NO:11), A5G15 (SEQ ID NO:12), A5G56 (SEQ ID NO:13), A5G80 (SEQ ID NO:14), A5G81 (SEQ ID NO:15), A5G82 (SEQ ID NO: 16), A5G84 (SEQ ID NO:17), A5G101 (SEQ ID NO:18), A5G109 (SEQ ID NO:19), hereinafter referred to for easy reference as Sequence Group A, but more preferably selected from the group consisting of AG73 (SEQ ID NO:1), A-13 (SEQ ID NO:3), HA3G76 (SEQ ID NO:8), A4G82 (SEQ ID NO:11), A5G81 (SEQ ID NO: 15) and A5G101 (SEQ ID NO:18), hereinafter referred to for easy reference as Sequence Group B.

The laminin peptides of the present invention may be prepared by known chemical synthetic methods or by biotechnological methods. Assays useful for the screening and identification of laminin peptide analogs as inhibitors of Aβ fibrillogenesis are also disclosed. In addition, methods are disclosed for the labeling of polypeptides derived from the invention for diagnosis of Alzheimer's and other Aβ amyloidoses.

The present invention relates to the novel and surprising discovery that laminin globular-domain derived peptides are inhibitors of Alzheimer's disease amyloidosis, and therefore have potential use for the therapeutic intervention of Alzheimer's disease and related Aβ disorders.

It is therefore an object of the present invention is to provide a method for treating Alzheimer's disease and other disorders involving the formation and persistence of Aβ, comprising the administration of laminin-derived peptides.

Another object of the present invention is to disclose specific laminin globular domain-derived peptides and other novel analogs and derivatives thereof, the administration of which comprises a method for treating Alzheimer's disease and other Aβ amyloidoses.

The invention also relates to pharmaceutical compositions comprising the laminin globular domain-derived peptides and other analogs and derivatives of such peptides, or pharmaceutically acceptable salts thereof for use in the treatment of Alzheimer's disease and other Aβ amyloidoses.

As used herein the term "laminin globular domain-derived peptide" is used to include each laminin globular domain-derived peptide which was surprisingly found to inhibit Aβ fibrillogenesis as disclosed herein, analogs, derivative and fragments thereof that retain the activity of the complex peptide. The term analogs are intended to include variants on the peptide molecule brought about, for example, homologous substitution of individual or several amino acid residues. The term derivative is used to include minor chemical changes that may be made to each of the laminin globular domain-derived peptides themselves or analogs thereof that maintain the biological activity of each of the parent peptides disclosed.

The invention also discloses methods to utilize the laminin-derived peptides as diagnostic or imaging agents for Alzheimer's disease and other Aβ amyloidoses.

The invention also discloses methods to utilize antibodies made against laminin-derived peptides as therapeutic agents for the treatment of Alzheimer's disease and other Aβ amyloid disorders.

A primary object of the present invention is to establish new therapeutic methods for Alzheimer's disease and other disease involving the accumulation of Aβ. These Aβ diseases include, but are not limited to, the amyloid associated with Alzheimer's disease and Down's syndrome, and various forms of cerebral amyloidosis, known to those knowledgeable in the art.

A primary object of the present invention is to use laminin globular domain derived peptides as potent inhibitors of Aβ amyloid formation, deposition, accumulation and/or persistence in Alzheimer's disease and other Aβ amyloidoses. Laminin globular domain derived peptides include, but are not limited to, the peptides of Sequence Group A, and more preferably the peptides of Sequence Group B and/or A5G109 (SEQ ID NO:19).

Yet another object of the present invention is to use analogs or derivatives thereof of each of the laminin globular domain derived peptides as potent inhibitors of Aβ amyloid formation, deposition, accumulation and/or persistence in Alzheimer's disease and other Aβ amyloidoses. Laminin globular domain derived peptides include but are not limited to, the peptides of Sequence Group A, and more preferably the peptides of Sequence Group B.

Yet another object of the present invention is to use peptidomimetic compounds modeled from the laminin globular domain peptides disclosed herein, including but not limited to, the peptides of Sequence Group A.

Yet another aspect of the present invention is to make use of laminin globular domain-derived peptides including, but not limited to, the peptides of Sequence Group A, and fragments or analogs thereof, as potential therapeutics to inhibit the deposition, formation and accumulation of fibrillar amyloid in Alzheimer's disease and other Aβ amyloidosis disorders, and to enhance the clearance and/or removal of pre-formed amyloid deposits in brain (for Alzheimer's disease and Down's syndrome and other Aβ amyloidoses).

Yet another object of the present invention is to use the laminin globular domain-derived peptides of the present invention, and all constituents, analogs or variants thereof, including peptides which have at least 70% identity to the sequences disclosed herein. Specific laminin globular domain-derived peptides as described above may be derived from any species including, but are not limited to, human, murine, bovine, porcine, and/or equine species.

Yet another object of the present invention is to use laminin globular domain-derived peptides as described herein as a specific indicator for the presence and extent of laminin breakdown in brain by monitoring biological fluids including, but not limited to, cerebrospinal fluid, blood, serum, urine, saliva, sputum and stool.

Yet another object of the present invention is to make use of peptides or analogs or derivatives thereof as described herein, including but not limited to, the peptides of Sequence Group A, as potential blocking therapeutics for the interaction of laminin and laminin-derived fragments in a number of biological processes and diseases (such as in Alzheimer's disease, Down's syndrome and other amyloid diseases).

Another object of the present invention is to use pills, tablets, caplets, soft and hard gelatin capsules, lozenges, sachets, cachets, vegicaps, liquid drops, elixers, suspensions, emulsions, solutions, syrups, tea bags, aerosols (as a solid or in a liquid medium), suppositories, sterile injectable solutions, and sterile packaged powders, which contain laminin globular domain-derived peptides, including but not limited to, the peptides of Sequence Group A, and analogs, derivatives or fragments thereof, to treat patients with Alzheimer's disease and other Aβ amyloidoses.

Yet another object of the present invention is to provide compositions and methods involving administering to a subject a therapeutic dose of laminin globular domain-derived peptides, which inhibit Aβ amyloid deposition, including but not limited to, the peptides of Sequence Group A, and analogs, derivatives or fragments thereof. Accordingly, the compositions and methods of the invention are useful for inhibiting amyloidosis in disorders in which amyloid deposition occurs. The peptides of the invention can be used therapeutically to treat amyloidosis or can be used prophylactically in a subject susceptible to amyloidosis. The methods of the invention are based, at least in part, in directly inhibiting Aβ amyloid fibril formation, and/or causing dissolution of pre-formed Aβ amyloid fibrils.

Yet another object of the present invention is to provide pharmaceutical compositions for treating Aβ amyloidosis. The pharmaceutical compositions include a therapeutic compound of the invention in an amount effective to inhibit Aβ amyloid deposition and a pharmaceutically acceptable vehicle.

Yet a further aspect of the present invention is to use anti-idiotypic antibodies to laminin-derived protein fragments and/or laminin-derived polypeptides as potent inhibitors of amyloid formation, deposition, accumulation and/or persistence in Alzheimer's disease and other Aβ amyloidoses.

Another aspect of the invention is to provide new and novel polyclonal and/or monoclonal peptide antibodies which can be utilized in a number of in vitro assays to specifically detect Aβ-binding laminin derived protein fragments and/or Aβ-binding laminin derived polypeptides in human tissues and/or biological fluids. Polyclonal or monoclonal antibodies that are made specifically against a peptide portion or fragment of laminin which interacts with Aβ can be utilized to detect and quantify amyloid disease specific laminin fragments in human tissues and/or biological fluids. These antibodies can be made by administering the peptides in antigenic form to a suitable host. Polyclonal or monoclonal antibodies may be prepared by standard techniques known to those skilled in the art.

Another object of the present invention is to use laminin-derived polypeptides referred to above, for the detection and specific localization of laminin peptides important in the amyloid diseases in human tissues, cells, and/or cell culture using standard immunohistochemical techniques.

Yet another aspect of the present invention is to use antibodies recognizing any of the Aβ-binding laminin fragments, and/or laminin-derived polypeptides including, but not limited to, the peptides of Sequence Group A, and analogs, derivatives or fragments thereof, for in vivo labeling; for example, with a radionucleotide, for radioimaging to be utilized for in vivo diagnosis, and/or for in vitro diagnosis.

Another object of the present invention is to use Aβ-binding laminin-derived polypeptides or fragments thereof, in conjunction with polyclonal and/or monoclonal antibodies generated against these peptide fragments, using in vitro assays to detect amyloid disease specific autoantibodies in human biological fluids. Specific assay systems can be utilized to not only detect the presence of autoantibodies against Aβ-binding laminin-derived protein fragments or polypeptides thereof in biological fluids, but also to monitor the progression of disease by following elevation or diminution of laminin protein fragments and/or laminin-derived polypeptide autoantibody levels.

Another aspect of the invention is to utilize laminin-derived protein fragments and/or laminin-derived polypeptide antibodies and/or molecular biology probes for the detection of these laminin derivatives in human tissues in the amyloid diseases.

Yet another object of the present invention is to use the laminin-derived protein fragments or polypeptides of the present invention in each of the various therapeutic and diagnostic applications described above. The laminin-derived protein fragments include, but are not limited to, a ~55 kDa fragment of laminin generated by trypsin digestion, a ~55 kDa fragment of laminin generated by elastase digestion, and a ~30 kDa fragment of laminin generated by trypsin digestion. The laminin-derived polypeptides include, but are not limited to, the peptides of Sequence Group A, and analogs, derivatives or fragments thereof, including peptides which have at least 70% identity to the sequences disclosed herein. Specific laminin-derived protein fragments or peptides as described above may be derived from any species including, but are not limited to, human, murine, bovine, porcine, and/or equine species.

Another object of the invention is to provide polyclonal and/or monoclonal peptide antibodies that can be utilized in a number of in vitro assays to specifically detect laminin protein fragments or polypeptides in human tissues and/or biological fluids. Polyclonal or monoclonal antibodies made specifically against a peptide portion or fragment of any of the laminin fragments or polypeptides described herein can be utilized to detect and quantify laminin-derived protein fragments or laminin-derived polypeptides in human tissues and/or biological fluids. These antibodies can be made by isolating and administering the laminin-derived fragments and/or polypeptides in antigenic form to a suitable host. Polyclonal or monoclonal antibodies may be prepared by standard techniques by one skilled in the art.

Yet another object of the present invention is to use laminin-derived fragment or polypeptide-derived antibodies as described herein as a specific indicator for the presence and extent of laminin breakdown in brain by monitoring biological fluids including, but not limited to, cerebrospinal fluid, blood, serum, urine, saliva, sputum, and stool.

Yet another object of the present invention is to use laminin-derived fragment or polypeptide antibodies as described herein as a specific indicator for the presence, extent and/or progression of Alzheimer's disease and/or other brain amyloidoses by monitoring biological fluids including, but not limited to, cerebrospinal fluid, blood, serum, urine, saliva, sputum, and stool.

Yet another object of the present invention is to use laminin-derived fragment or polypeptide-derived antibodies as described herein as a specific indicator for the presence and extent of laminin breakdown in systemic organs by monitoring biological fluids including, but not limited to, cerebrospinal fluid, blood, serum, urine, saliva, sputum, and stool.

Yet another object of the present invention is to use laminin-derived fragment or polypeptide antibodies as described herein as a specific indicator for the presence and extent of amyloidosis in type II diabetes by monitoring biological fluids including, but not limited to, cerebrospinal fluid, blood, serum, urine, saliva, sputum, and stool.

Yet another object of the present invention is to use laminin-derived fragment or polypeptide antibodies as described herein as a specific indicator for the presence and extent of amyloidosis in other systemic amyloidoses by monitoring biological fluids including, but not limited to, cerebrospinal fluid, blood, serum, urine, saliva, sputum, and stool.

Yet another object of the present invention is to make use of peptides or fragments of laminin as described herein, including but not limited to, the peptides of Sequence Group A, and fragments thereof, as potential blocking therapeutics for the interaction of laminin and laminin-derived fragments in a number of biological processes and diseases (such as in Alzheimer's disease and other amyloid diseases described herein).

Yet another object of the invention is to utilize specific laminin-derived fragment or polypeptide antibodies, as described herein, for the detection of these laminin fragments in human tissues in the amyloid diseases.

Preferred pharmaceutical compositions have at least one laminin peptide or fragment thereof selected from the Sequence Group A consisting of AG73 (SEQ ID NO:1), C-16 (SEQ ID NO:2), A-13 (SEQ ID NO:3), HA3G47 (SEQ ID NO:4), HA3G58 (SEQ ID NO:5), HA3G67 (SEQ ID NO:6), HA3G74 (SEQ ID NO:7), HA3G76 (SEQ ID NO:8), HA3G79 (SEQ ID NO:9), HA3G83 (SEQ ID NO:10), A4G82 (SEQ ID NO:11), A5G15 (SEQ ID NO:12), A5G56 (SEQ ID NO:13), A5G80 (SEQ ID NO:14), A5G81 (SEQ ID NO:15), A5G82 (SEQ ID NO: 16), A5G84 (SEQ ID NO:17), A5G101 (SEQ ID NO:18) and A5G109 (SEQ ID NO:19).

In preferred embodiments the compositions (all from Sequence Group B) have the structure Arg-Lys-Arg-Leu-Gln-Val-Gln-Leu-Ser-Ile-Arg-Thr (SEQ ID NO: 1) or Arg-Gln-Val-Phe-Gln-Val-Ala-Tyr Ile-Ile-Ile-Lys-Ala (SEQ ID NO:3) or Tyr-Leu-Ser-Lys-Gly-Arg-Leu-Val-Phe-Ala-Leu-Gly (SEQ ID NO:8) or Thr-Leu-Phe-Leu-Ala-His-Gly-Arg-Leu-Val-Phe-Met (SEQ ID NO:11) or Ala-Gly-Gln-Trp-His-Arg-Val-Ser-Val-Arg-Trp-Gly (SEQ ID NO:15) or Asp-Gly-Arg-Trp-His-Arg-Val-Ala-Val-Ile-Met-Gly (SEQ ID NO:18).

Alternate preferred compositions and pharmaceutical compositions have at least one laminin peptide or fragment thereof selected from the Sequence Group D consisting of DP2 D-A13, DP3 D-HA3G76, DP4 D-A4G82, DP5 D-A5G81, DP6 D-A5G101, DP7 D-HA3G47, DP8 D-HA3G58, DP9 D-HA3G74, DP10 D-HA3G83, DP11 D-A5G82, DP13 D-R-AG73, DP14 D-R-A13, DP15 D-R-HA3G76, DP16 D-R-A4G82, and DP17 D-R-A5G81, and more preferably from the Sequence Group E consisting of DP2 D-A13, DP4 D-A4G82, DP5 D-A5G81, DP6 D-A5G101, DP8 D-HA3G58, DP10 D-HA3G83, DP14 D-R-A13, DP15 D-R-HA3G76 and DP16 D-R-A4G82.

In any of the above structures or sequences, the individual amino acids may be either L- or D-amino acids. The pharmaceutical composition have a therapeutically effective amount of any of the above structures or sequences, preferably together with a pharmaceutically acceptable carrier, diluent or excipient.

In any of the above structures or sequences, the nomenclature or symbolic representation of any or all of the individual amino acids may be given by either the standard 3-letter abbreviation for the amino acid, or the standard single letter code for the amino acid, and sometimes both in appropriate cases.

Preferred pharmaceutical agents for treating Aβ amyloidosis in a patient have a therapeutically effective amount of a polypeptide selected from Sequence Group B or A5G109 (SEQ ID NO:19), and have an Aβ amyloid inhibitory activity or efficacy greater than 30%, as compared to duly established controls, such as patients who do not received the preferred pharmaceutical agent.

An important Aβ amyloidosis to which the disclosed therapeutics are addressed is Alzheimer's disease. A preferred therapeutically effect amount of disclosed polypeptide is a dosage in the range of from about 10 µg to about 50 mg/kg body weight/per day, and more preferably in the range of from about 100 µg to about 10 mg/kg body weight per day.

The pharmaceutical agent may advantageously be administered in a parenterally injectable or infusible form or orally.

A method is also disclosed to diagnose a disease or susceptibility to Aβ amyloidosis related to the level of laminin-derived polypeptides. First the levels of laminin-derived polypeptides in a sample are determined, whereby the levels are indicative of the presence of Aβ amyloidosis, susceptibility to Aβ amyloidosis, or progression of Aβ amyloidosis. In preferred methods the laminin-derived polypeptides are selected from the group consisting of Sequence Group B and/or A5G109 (SEQ ID NO:19).

The sample assayed may be a biological fluid, and the biological fluid may be serum derived from humans.

A method of making an antibody is also disclosed, the method producing antibodies from a peptide sequence selected from the group consisting of Sequence Group B and/or A5G109 (SEQ ID NO:19), and fragments thereof. The method preferably includes production of at least one type of antibody selected from the group consisting of polyclonal, monoclonal, chimeric, and anti-idiotypic antibodies and monitoring a biological fluid for the presence and extent of laminin-derived polypeptides as an indicator for the extent of an amyloid disease and radiolabeling the antibodies for radioimaging or in vivo diagnosis for detection of laminin-derived protein fragments or laminin-derived polypeptides.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings are illustrative of embodiments of the invention and are not meant to limit the scope of the invention.

FIG. 6 is a schematic representation of the sequence of murine alpha-4 chain globular domain peptides disclosed herein (SEQ ID NO: 32).

FIG. 7 is a schematic representation of the sequence of murine alpha-5 chain globular domain peptides disclosed herein (SEQ ID NO: 33).

FIG. 8 is a table which includes laminin globular domain-derived peptides (SEQ ID NOS 1, 20-21, 2, 22, 3, 23 4-6, 24, 7, 25, 8-10, 26, 11-12, 27-28, 13, 29, 14-19, and 30, respectively in order of appearance) which can disrupt/disassemble pre-formed Alzheimer's Aβ 1-40 fibrils.

[Designation FIG. 11 intentionally left unused at this time]

FIGS. 12A-F are laminin-derived peptide sequences for 12-13 mer peptides DP1-18 and LP19-25, and 7 mer peptides DP 26-49.

FIG. 13 is a graph of in vitro screening of peptides DP1-6, DP13-18, and LP19, 25 demonstrating their effects on inhibition of Ab 1-42 amyloid fibrils (Alzheimer's Disease) as assessed by a Thioflavin T fluorometry assay.

Figure 14:
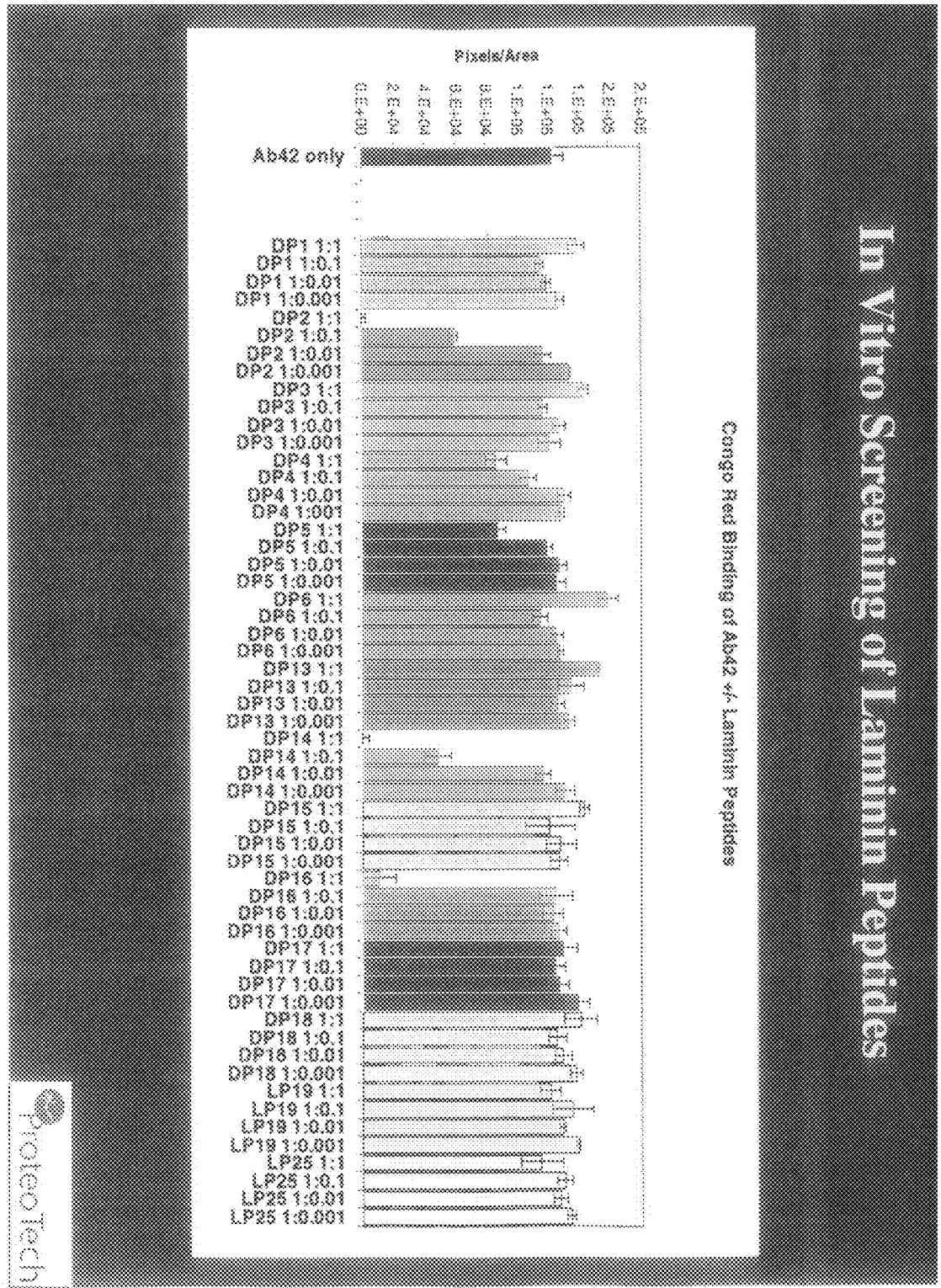

FIG. 14 is a graph of in vitro screening of peptides DP1-6, DP13-18, and LP19, 25 demonstrating their effects on inhibition of Ab 1-42 amyloid fibrils as assessed by a Congo Red binding assay.

FIG. 15 is a graph of in vitro screening of peptides DP2, 14, 7-12, LP 19, 25, AG73, A4G82, iAβ5, and A5G101 demonstrating their effects on inhibition of Ab 1-42 amyloid fibrils as assessed by a Thioflavin T fluorometry assay.

Figure 16:
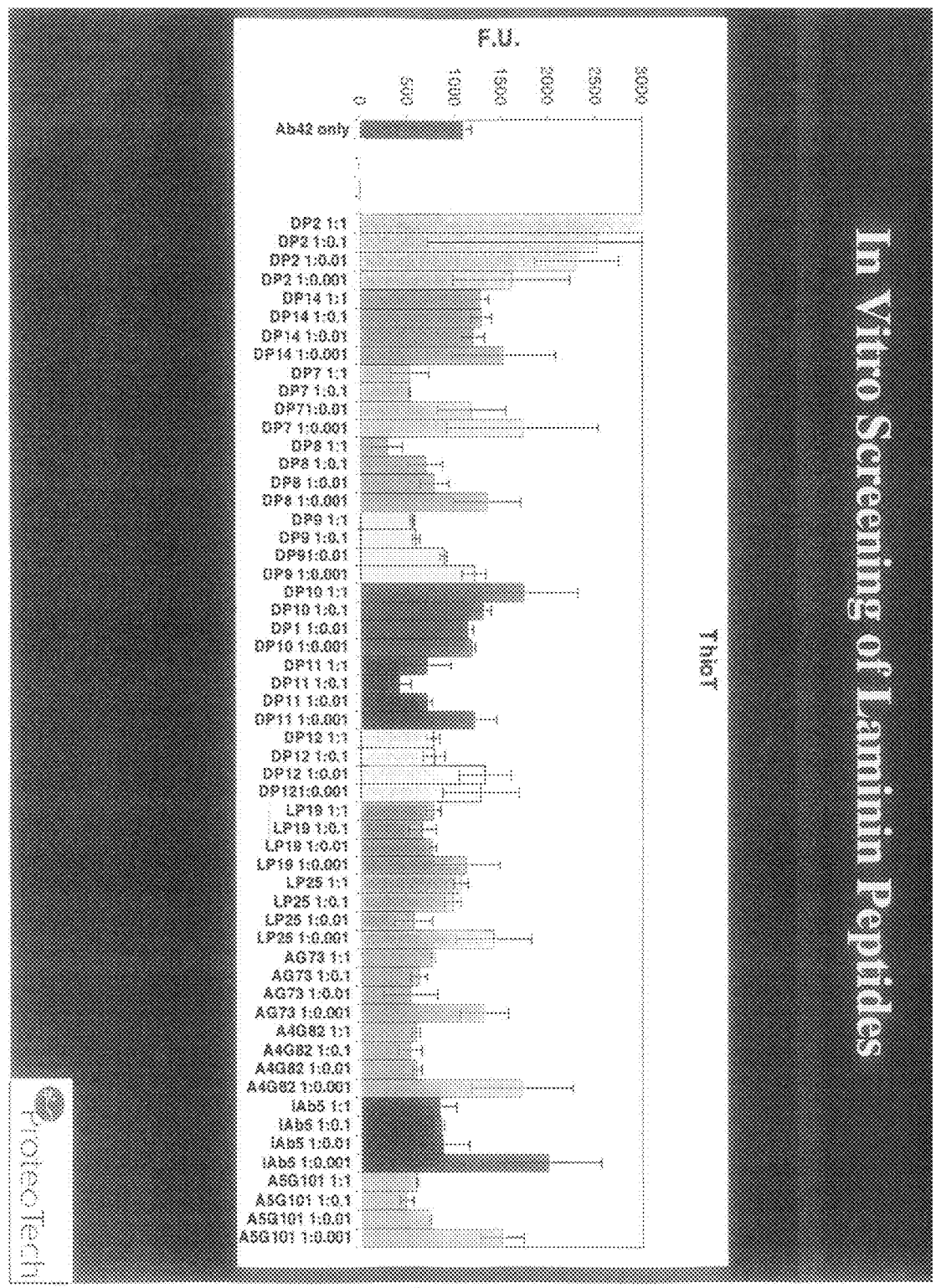
Figure 16:
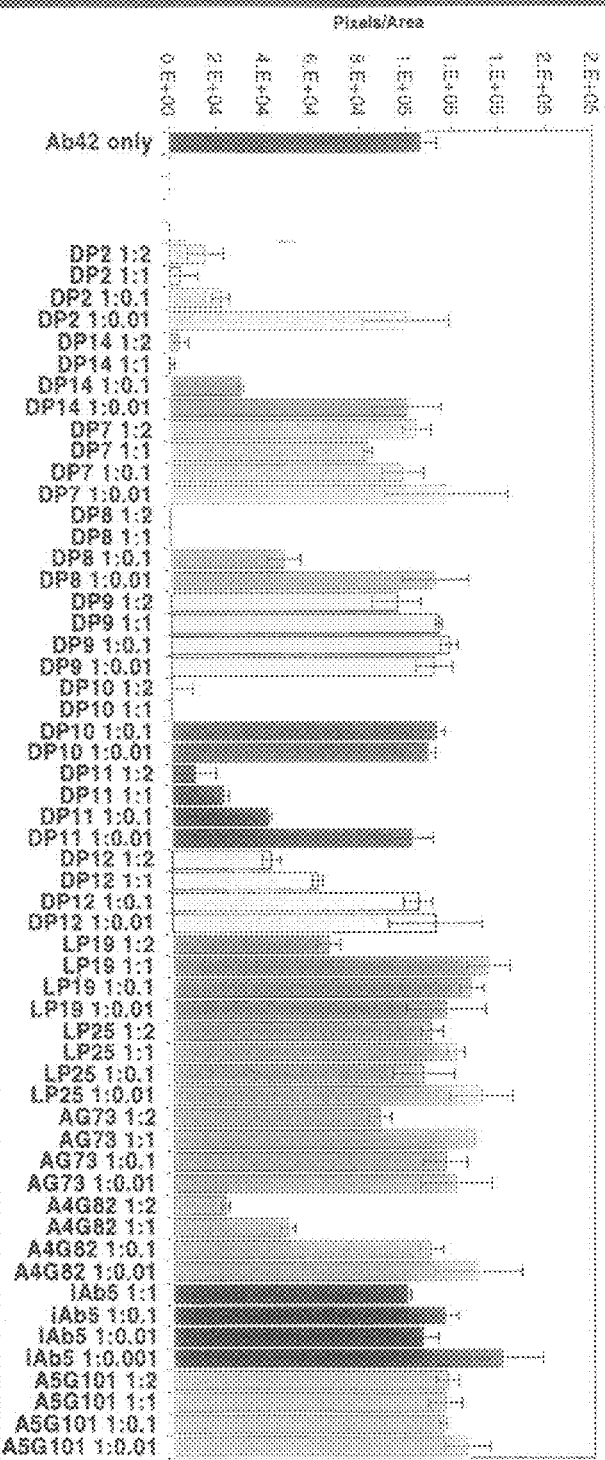
Figure 17:
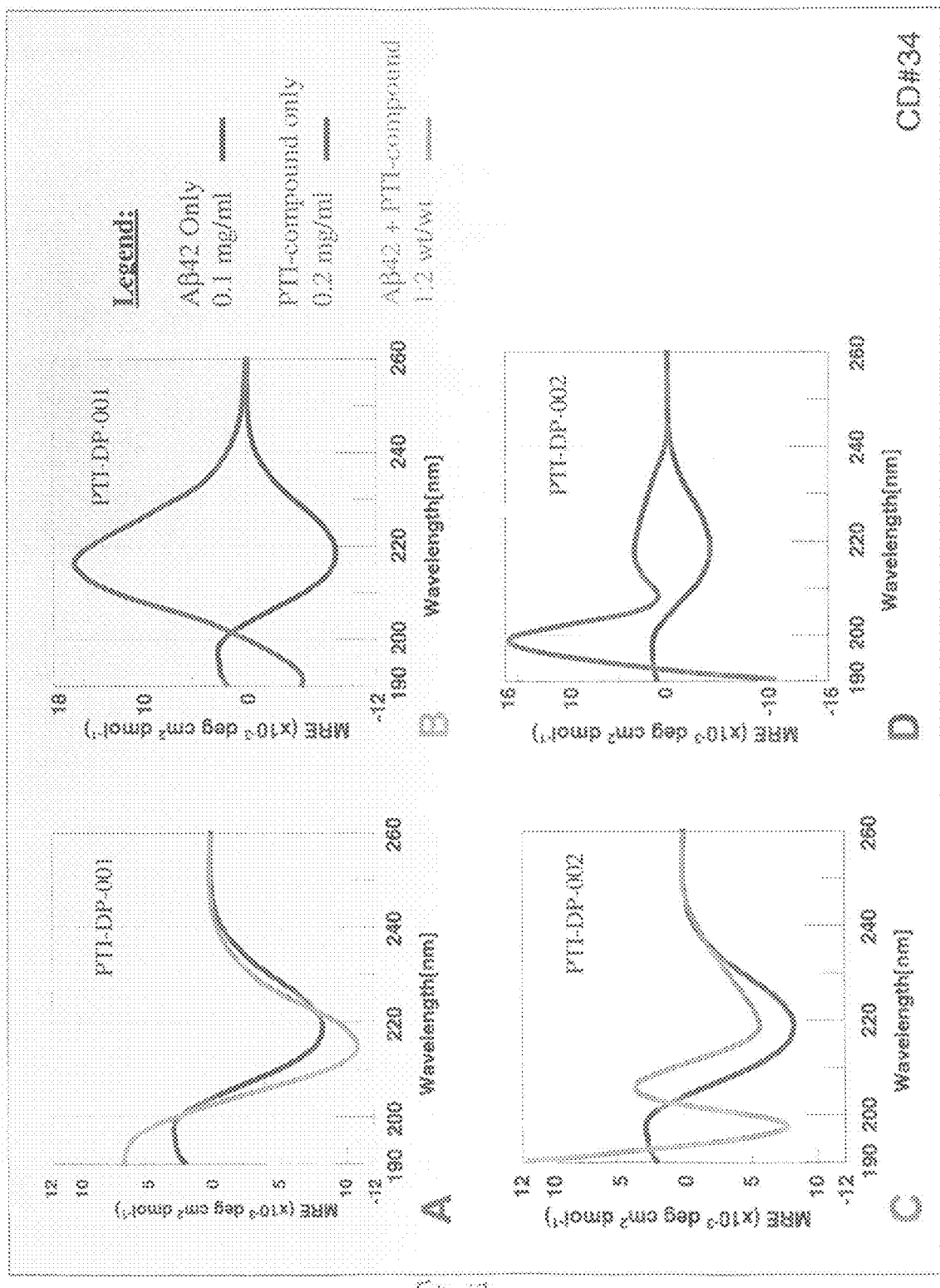
Figure 18:
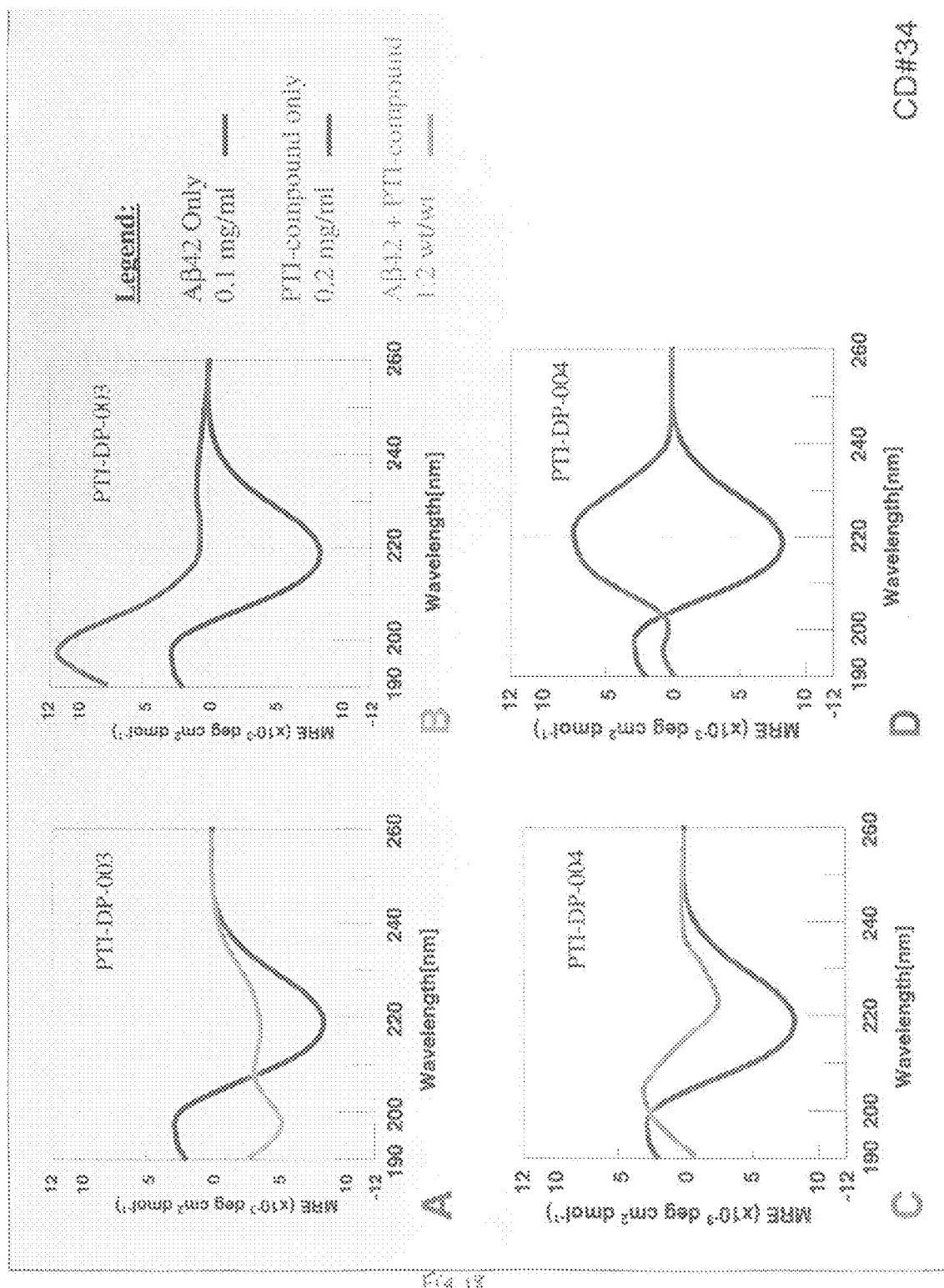
Figure 19:
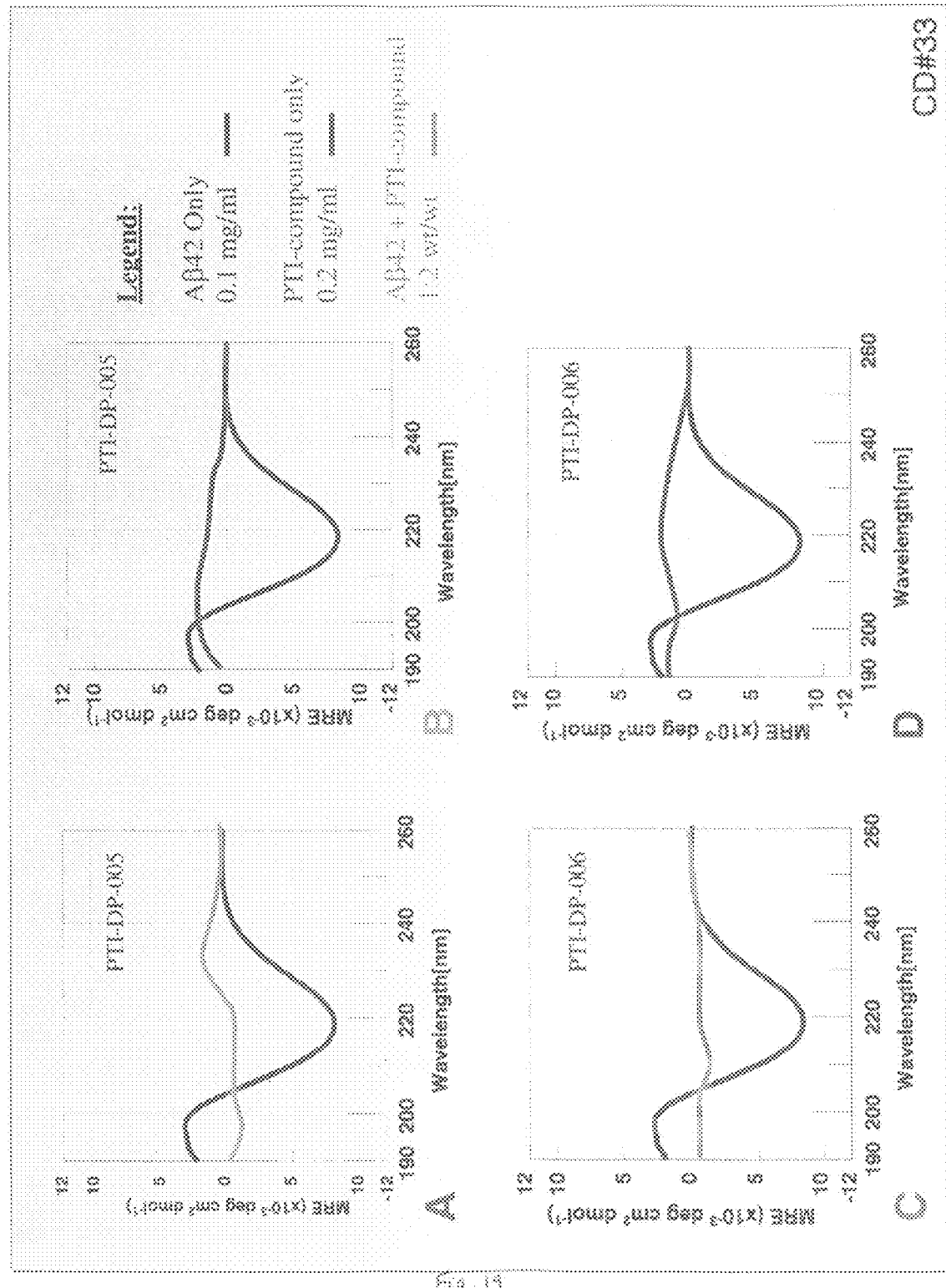
Figure 20:
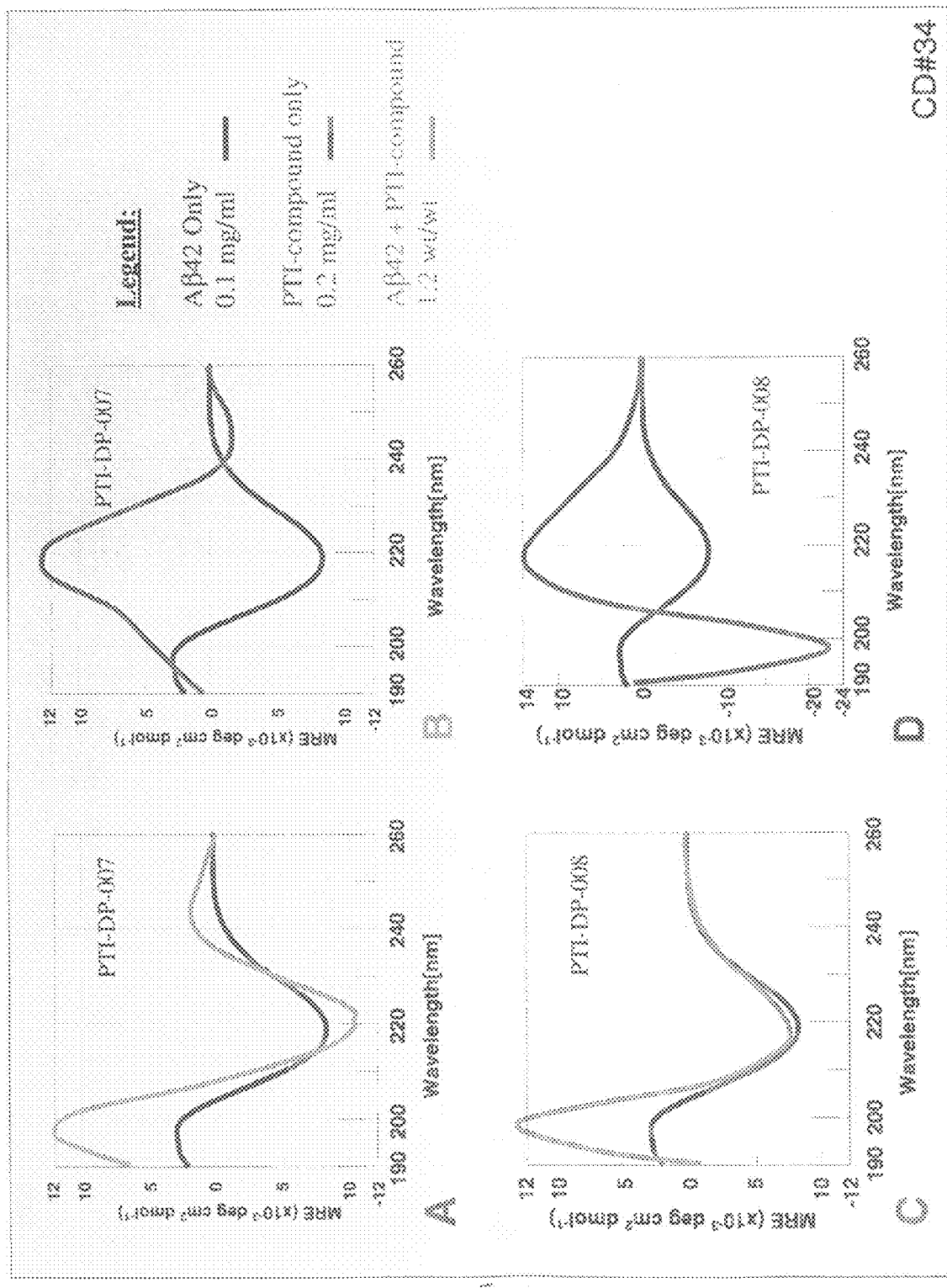
Figure 34:
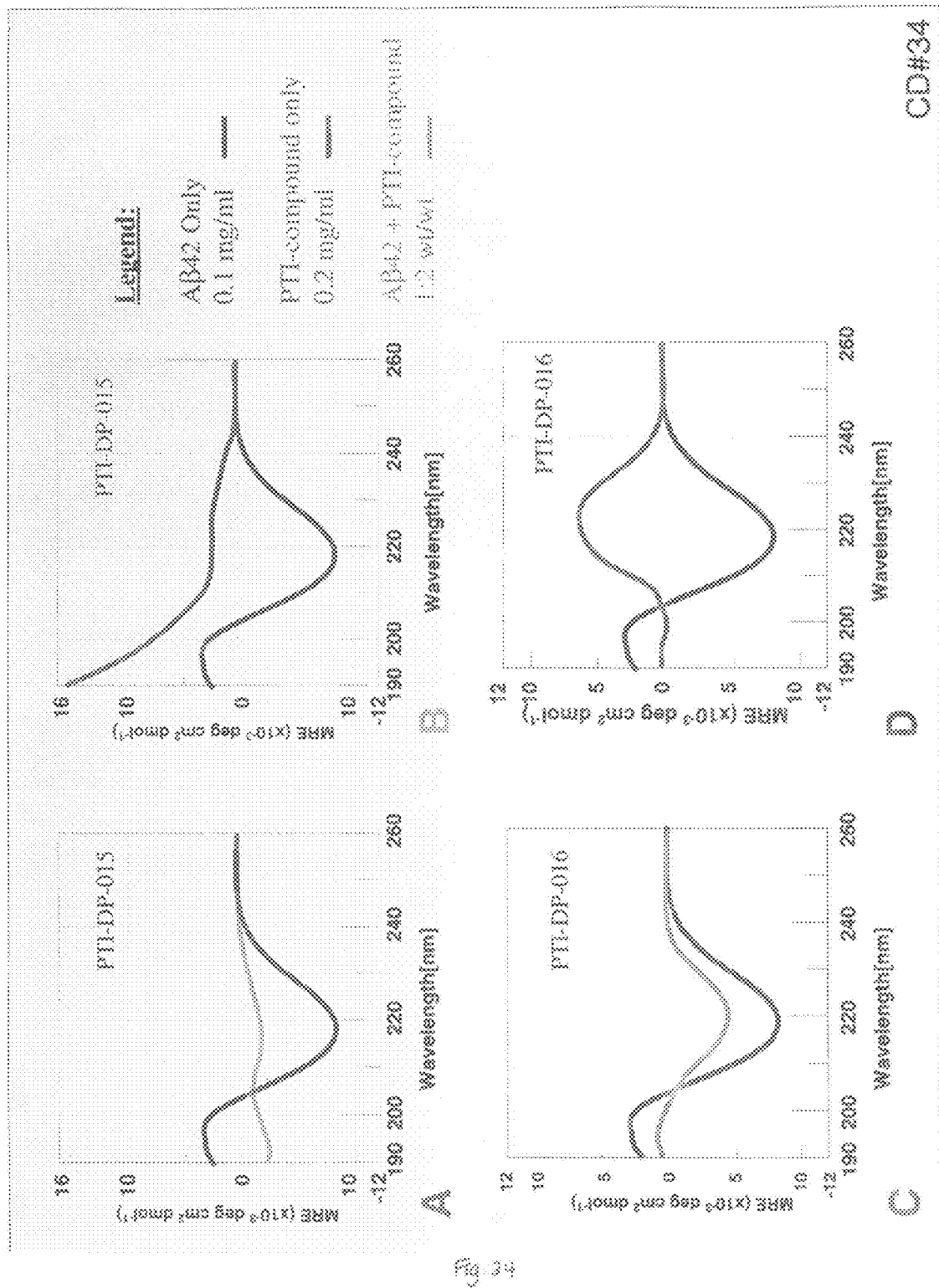

FIG. 16 is a graph of in vitro screening of peptides DP2, 14, 7-12, LP 19, 25, AG73, A4G82, iAβ5, and A5G101 demonstrating their effects on inhibition of Ab 1-42 amyloid fibrils as assessed by a Congo Red binding assay.

FIGS. 17*a-d* are graphs of peptides DP1-2 demonstrating their effects on inhibition of Ab 1-42 amyloid fibrils as assessed by circular dichroism spectroscopy (CD).

FIGS. 18*a-d* are graphs of peptides DP3-4 demonstrating their effects on inhibition of Ab 1-42 amyloid fibrils as assessed by CD.

FIG. 17A-D are graphs of peptides DP1-2 demonstrating their effects on inhibition of Aβ 1-42 amyloid fibrils as assessed by circular dichroism spectroscopy (CD).

FIG. 18A-D are graphs of peptides DP3-4 demonstrating their effects on inhibition of Aβ 1-42 amyloid fibrils as assessed by CD.

FIG. 19A-D are graphs of peptides DP5-6 demonstrating their effects on inhibition of Aβ 1-42 amyloid fibrils as assessed by CD.

FIG. 20A-D are graphs of peptides DP7-8 demonstrating their effects on inhibition of Aβ 1-42 amyloid fibrils as assessed by CD.

FIG. 21A-D are graphs of peptides DP9-10 demonstrating their effects on inhibition of Aβ 1-42 amyloid fibrils as assessed by CD.

FIG. 22A-D are graphs of peptides DP11-12 demonstrating their effects on inhibition of Aβ 1-42 amyloid fibrils as assessed by CD FIG. 23A-D are graphs of peptides DP13-14 demonstrating their effects on inhibition of Aβ 1-42 amyloid fibrils as assessed by CD.

FIG. 24A-D are graphs of peptides DP15-16 demonstrating their effects on inhibition of Aβ 1-42 amyloid fibrils as assessed by CD.

FIG. 25A-D are graphs of peptides DP17-18 demonstrating their effects on inhibition of Aβ 1-42 amyloid fibrils as assessed by CD.

FIG. 26A-B are graphs of peptide LP19 demonstrating its effects on inhibition of Aβ 1-42 amyloid fibrils as assessed by CD.

BEST MODE OF CARRYING OUT THE INVENTION

Accordingly the use of laminin-derived peptides for the treatment of Alzheimer's disease and other Aβ amyloidoses is disclosed. Specifically observed and isolated laminin globular domain-derived peptides disclosed herein have the ability to inhibit Aβ fibril formation, and cause a disruption of pre-formed Aβ amyloid fibrils, and therefore possess therapeutic potential in the treatment of Alzheimer's disease and other disorders involving the formation, deposition, accumulation and persistence of Aβ.

Pharmaceutically acceptable salts of the peptides disclosed in the present invention include both salts of the carboxy groups and the acid addition salts of the amino groups of the peptide molecule. Salts of the carboxy groups may be formed by methods known in the art and include inorganic salts such as sodium, calcium ammonium, ferric or zinc salts and the like and salts with organic bases such as those formed with amines such as triethanolamine, arginine or lysine, piperidine, procaine and the like. Acid addition salts include salts with mineral acids such as hydrochloric acid and sulphuric acid and salts of organic acids such as acetic acid or oxalic acid.

The pharmaceutical composition may contain laminin-derived peptides such as those disclosed herein as unique peptides or in polymerized or conjugated form attached to macromolecular carriers or polymers. The compositions may optionally contain pharmaceutically acceptable excipients. In an alternative embodiment the composition may contain the laminin-derived peptide alone.

The route of administration includes oral, intravenous, intra-peritoneal, intra-muscular, subcutaneous, intra-articular, intra-nasal, intra-thecal, intra-dermal, transdermal or by inhalation. An effective dose of each of the laminin-derived peptides disclosed herein as potential therapeutics for use in treating Aβ amyloidosis in Alzheimer's disease and other disorders be from about 1 µg to 500 mg/kg body weight, per single administration, which may readily be determined by one skilled in the art. The dosage depends upon the age, sex, health, and weight of the recipient, kind of concurrent therapy, if any, and frequency of treatment.

As used herein the laminin-derived polypeptides of the present invention may consist of –L amino acid, –D amino acids or a mixture of both forms. Amino acids in nature usually consist of –L amino acids. However, substitution with –D amino acids may demonstrate enhanced Aβ amyloid inhibitory activity, enhanced bioavailability due to less degradation in biological fluids (such as plasma), and enhanced penetration across the blood-brain-barrier. Polypeptides having an identical amino acid sequence to that found within a parent peptide but which all or part of the L-amino acids have been substituted with D-amino acids is part of the present invention for the development of therapeutics to treat Alzheimer's disease and other Aβ amyloidoses.

The –L or –D amino acids of the laminin-derived polypeptides of the present invention are further intended to include other peptide modifications, including derivatives, analogs and mimetics, that retain the ability of the polypeptides to inhibit Aβ amyloidosis as described herein. The terms "analog", "derivative" and "mimetic" as used herein are intended to include molecules which mimic the chemical structure of a L or D-peptidic structure, and retain the functional properties of a L- or D-peptidic structure. Approaches to designing peptide analogs, derivatives and mimetics are known in the art. For example, see P. S. Farmer, in *Drug Design*, E. J. Ariens, ed., Academic Press, New York, 1980, v. 10, pp. 119-143; Ball and Alewood, *J. Mol. Recognition* 3:55, 1990; Morgan and Gainor, *Ann. Rep. Med. Chem.* 24:243, 1989; and Freidinger, *Trends Pharmacol. Sci.* 10:270, 1989. See also Sawyer, "Peptidomimetic design and chemical approaches to peptide metabolism", in M D Taylor and G L Amidon, eds., in *Peptide-Based Drug Design: Controlling Transport and Metabolism*, Ch. 17, 1995; Smith et al, *J. Am. Chem. Soc.* 117:11113-11123, 1995; Smith et al, *J. Am. Chem. Soc.* 116:9947-9962, 1994; and Hirschman et al, *J. Am. Chem. Soc.* 115:12550-12568, 1993.

As used herein, a "derivative" of a therapeutic compound (e.g. a peptide or polypeptide) refers to a form of the peptide in which one or more reaction groups of the compound have been derivatized with a substituent group. Examples of peptide derivatives include peptides in which an amino acid side chain, the peptide backbone, or the amino- or carboxy-terminus has been derivatized (e.g., peptidic compounds with methylated amide linkages). As used herein an analog of a therapeutic compound refers to a compound which retains chemical structures necessary for functional activity (i.e. Aβ inhibitory activity), yet which also contains certain chemical structures which differ from the parent peptide. An example of an analog of a naturally occurring peptide is a peptide which includes one or more non-naturally-occurring amino acids. As used herein, a "mimetic" of a compound refers to a compound in which chemical structures of the compound are necessary for functional activity have been replaced with other chemical structures which mimic the conformation of the compound or peptides thereof. Examples of peptidomimetics include peptide compounds in which the peptide backbone is substituted with one or more benzodiazepine molecules (see James et al, *Science* 260: 1937-1942, 1993).

Analogs of the polypeptide compounds of the invention are intended to include compounds in which one or more L- or –D amino acids of the peptide structure are substituted with a homologous amino acid such that the properties of the original polypeptide are maintained. Preferably conservative amino acid substitutions are made at one or more amino acid residues. A "conservative amino acid substitution" in one in which the amino acid residue is replaced with an amino acid residue having a similar side chain. Families of amino acid residues having similar side chains have been defined in the art, including basic side chains (e.g. lysine, arginine, histidine), acidic side chains (e.g., aspartic acid, glutamic acid), uncharged polar side chains (e.g., glycine, asparagines, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine), and aromatic side chains (e.g., tyrosine, phenylalanine, tryptophan, histidine). Non-limiting examples of homologous substitutions that can be made in the peptidic structures of the invention include substitution of phenylalanine with tyrosine, leucine with valine, or other natural or non-natural amino acid having an aliphatic side chain and/or substitution of valine with leucine or other natural or non-natural amino acid having an aliphatic side chain.

As used herein "pharmaceutically acceptable carrier" includes any and all solvents, dispersion media, coatings, antibacterial and antifungal agents, isotonic and absorption delaying agents, and the like that are physiologically compatible. In one embodiment, the carrier is suitable for parenteral administration. Preferably, the carrier is suitable for administration into the central nervous system (e.g. intraspinally or intracerebrally). Alternatively, the carrier can be suitable for intravenous, intraperitoneal or intramuscular administration. In another embodiment, the carrier is suitable for oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is compatible with the active compound, use thereof in the pharmaceutical compositions of the invention is contemplated. Supplementary active compounds can also be incorporated into the compositions.

As used here in "Aβ amyloidoses" refers to amyloid diseases which involve the formation, deposition, accumulation and/or persistence of Aβ (i.e. beta-amyloid protein), including but not limited to Aβ containing 39-43 amino acids in length, but more preferably, Aβ 1-40, or Aβ 1-42, and mixtures or fragments thereof.

"Aβ amyloidoses" and "Aβ fibrillogenesis diseases" include, but are not limited to Alzheimer's disease, Down's syndrome, forms of familial amyloidosis, cerebrovascular amyloidosis and cerebral hemorrhage, cystatin C amyloid angiopathy, hereditary cerebral hemorrhage with amyloidosis (Dutch type), hereditary cerebral hemorrhage with amyloidosis (Icelandic type), and inclusion body myositis.

These and other features and advantages of the present invention will become more fully apparent when the following detailed description of the invention is read in conjunction with the accompanying figures which are illustrative of embodiments of the invention only, and are not meant to limit the scope of the invention.

Figure 1:
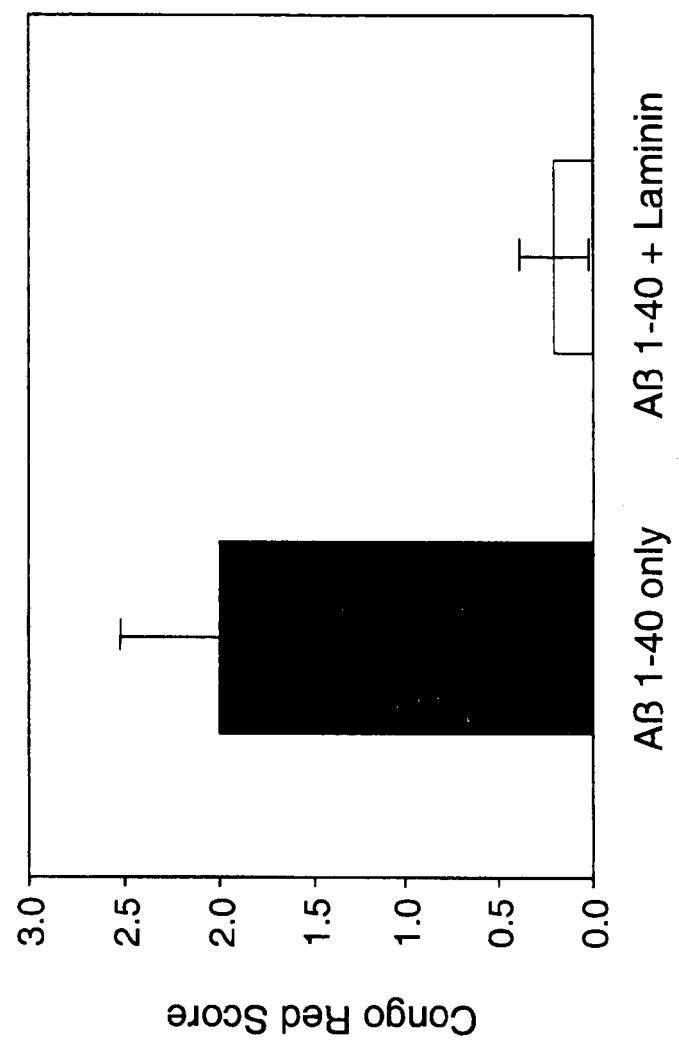
FIG. 1 is a graph demonstrating an inhibitory effect of Aβ amyloid deposition into rodent hippocampus by laminin.

FIG. 1 is a graph demonstrating inhibition of fibrillar Aβ amyloid deposition into rodent hippocampus by laminin. Laminin caused a significant 90% inhibition of Aβamyloid deposition in brain.

Figure 2:
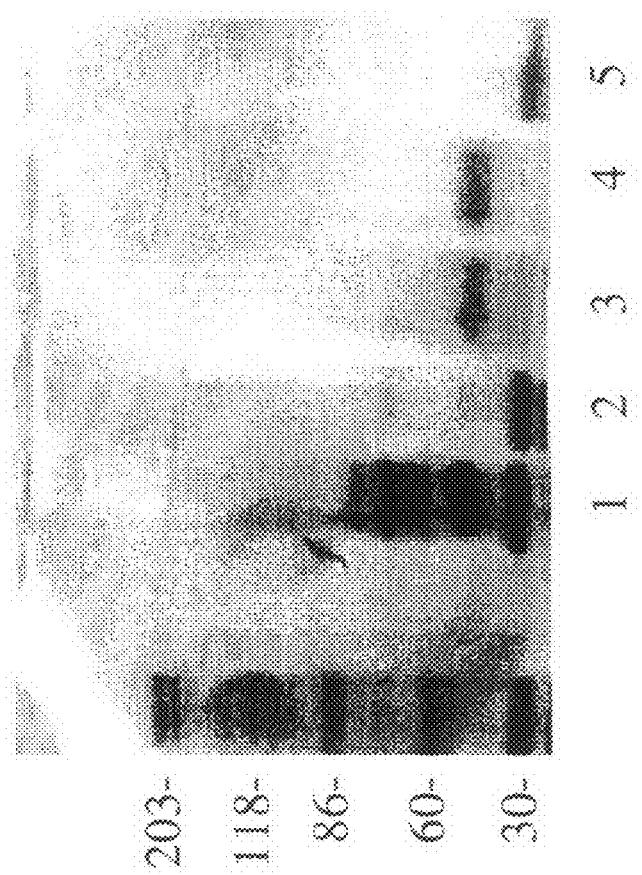
FIG. 2 is a copy of a black and white photograph of a Coomassie blue stained gel demonstrating purification and isolation of fragments of laminin which strongly interact with Aβ.

FIG. 2 is a black and white photograph of a Coomassie blue stained gel demonstrating purification and isolation of a ~55 kilodalton fragment of laminin, and a ~30 kilodalton subfragment of laminin, identified as fragments of laminin which strongly interact with Aβ.

Figure 3:
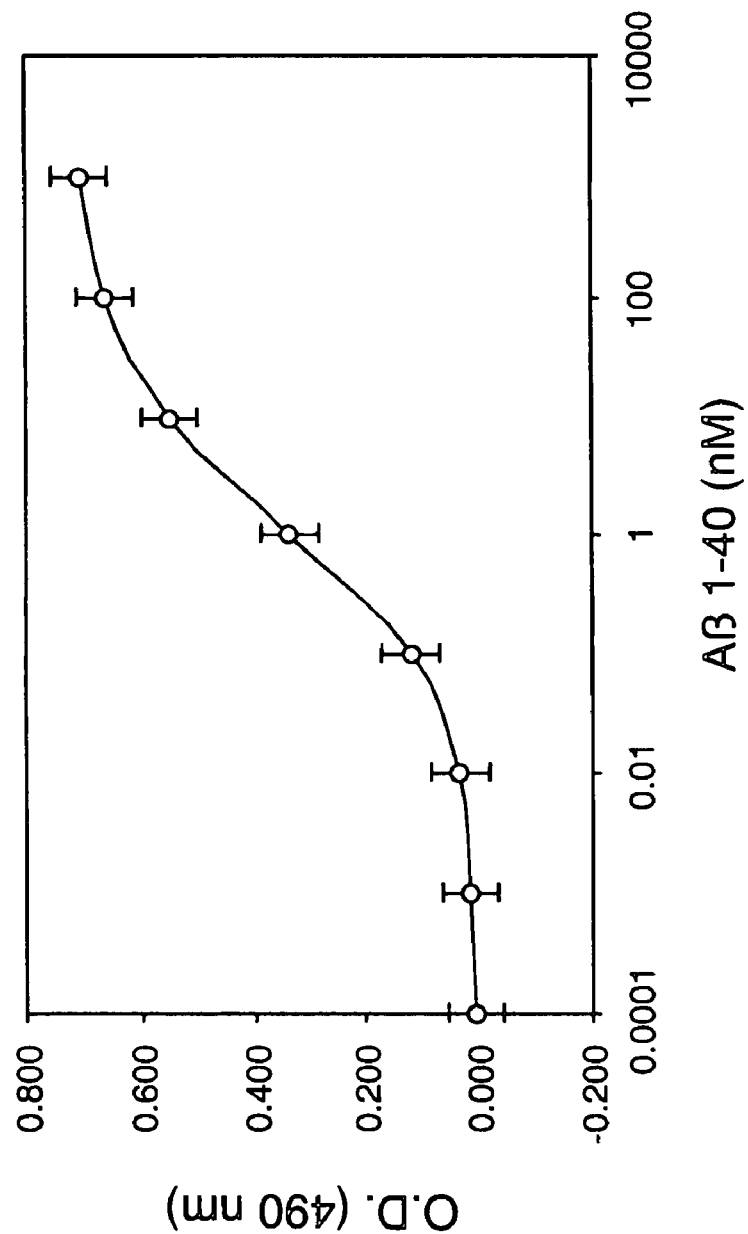
FIG. 3 is a graph demonstrating the strong binding interaction of Alzheimer's Aβ to the ~55 kilodalton laminin fragment. A single dissociation constant with a $K_d=2.0\times10^{-9}$ was determined.

FIG. 3 is a graph demonstrating the strong binding interaction of Alzheimer's Aβ to the ~55 kilodalton laminin fragment. A single dissociation constant with a $K_d=2.0\times10^{-9}$ was determined.

Figure 4:
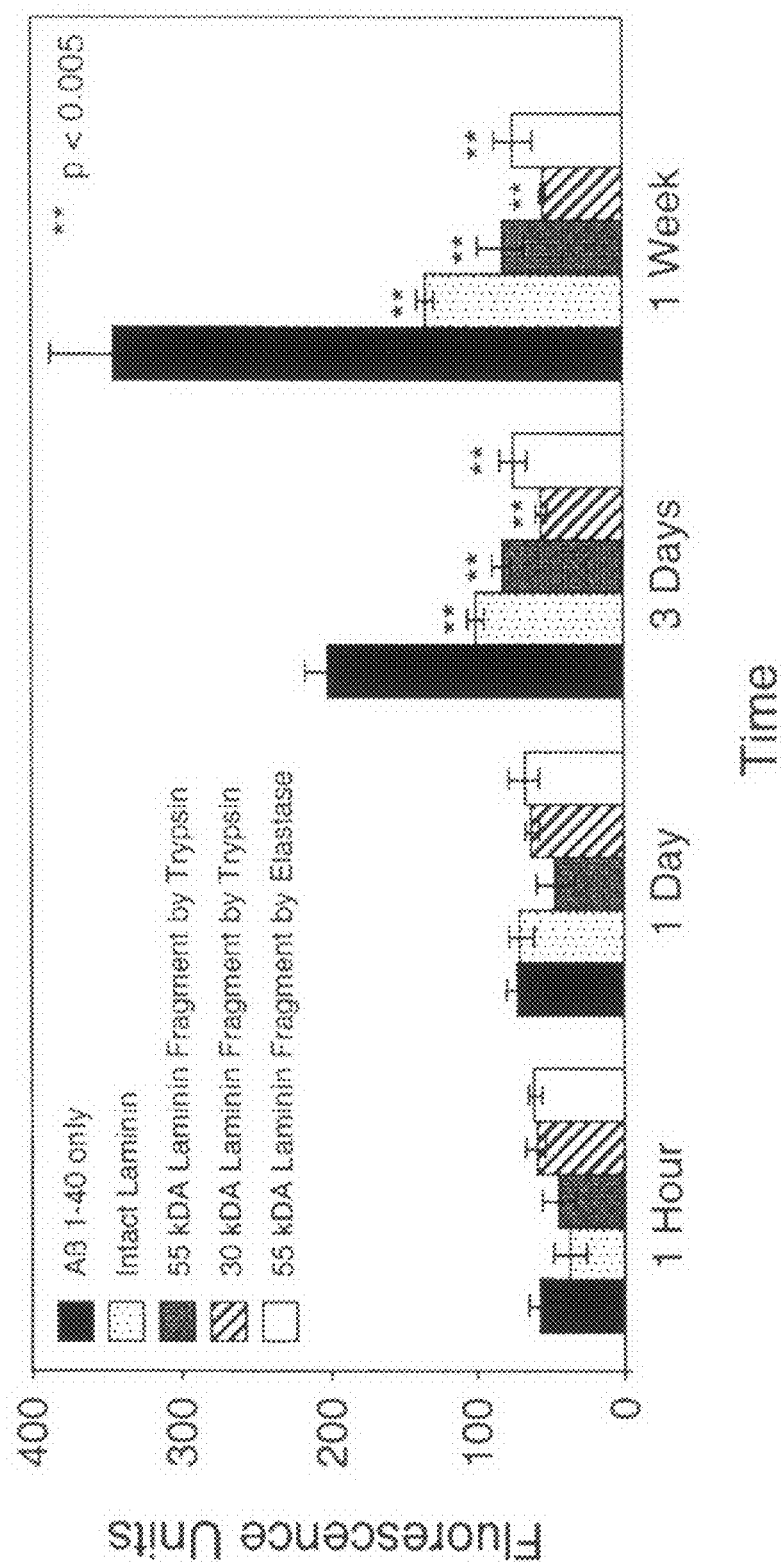
FIG. 4 is a graph demonstrating the inhibition of Alzheimer's Aβ fibril formation by selected fragments disclosed herein.

FIG. 4 is a graph demonstrating the inhibition of Alzheimer's Aβ fibril formation by various protease-generated laminin fragments. Intact laminin, ~55 kilodalton and ~30 kilodalton laminin-fragments obtained by trypsin digestion, and a ~55 kilodalton fragment of laminin obtained by elastase digestion, all significantly inhibited Alzheimer's Aβ fibril formation at 3 and 7 days.

Figure 5:
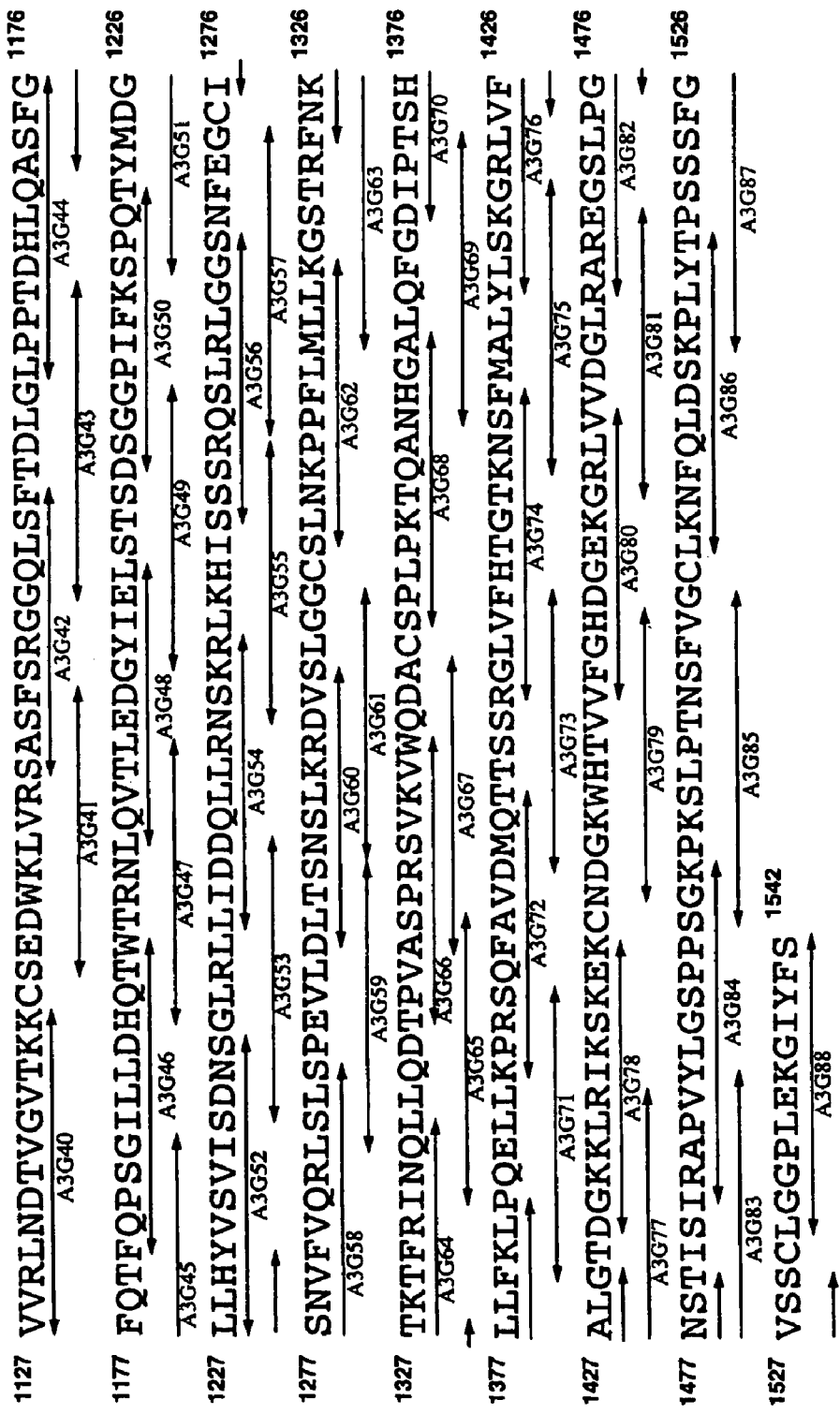
FIG. 5 is a schematic representation of the sequence of human alpha-3 chain globular domain peptides disclosed herein (SEQ ID NO:31).

FIG. 5 is a schematic that demonstrates the sequence of peptides derived from the human alpha-3 chain globular domain that was used for screening for Alzheimer's Aβ amyloid inhibitory activity. A total of 49 12-14 amino acid peptides (labeled A3G40 to A3G88) were synthesized and used for screening studies.

FIG. 6 is a schematic that demonstrates the sequence of peptides derived from the mouse alpha-4 chain globular domain that was used for screening for Alzheimer's Aβ amyloid inhibitory activity. A total of 117 12-14 amino acid peptides (labeled A4G-1 to A4G-116) were synthesized and used for screening studies.

FIG. 7 is a schematic that demonstrates the sequence of peptides derived from the mouse alpha-5 chain globular domain that was used for screening for Alzheimer's Aβ amyloid inhibitory activity. A total of 133 12-14 amino acid peptides (labeled A5G-1 to A5G-113) were synthesized and used for screening studies.

FIG. 8 is a table that identifies the laminin globular domain-derived peptides which can disrupt/disassemble pre-formed Alzheimer's Aβ 1-40 fibrils.

Figure 9:
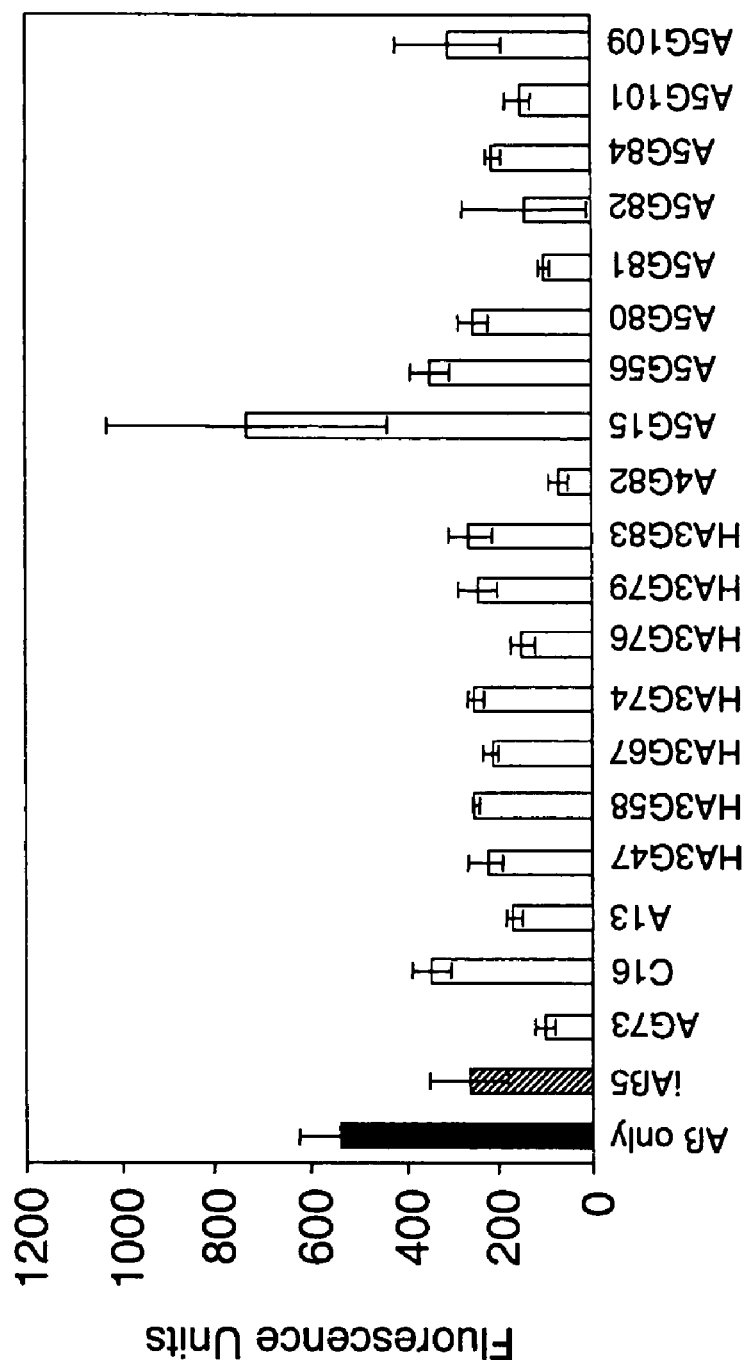
FIG. 9 is a graph demonstrating further testing of selected laminin globular-domain derived peptides against pre-formed Alzheimer's Aβ 1-42 fibrils.

FIG. 9 is a graph demonstrating the further testing of selected laminin globular-domain derived peptides against pre-formed Alzheimer's Aβ 1-42 fibrils.

Figure 10:
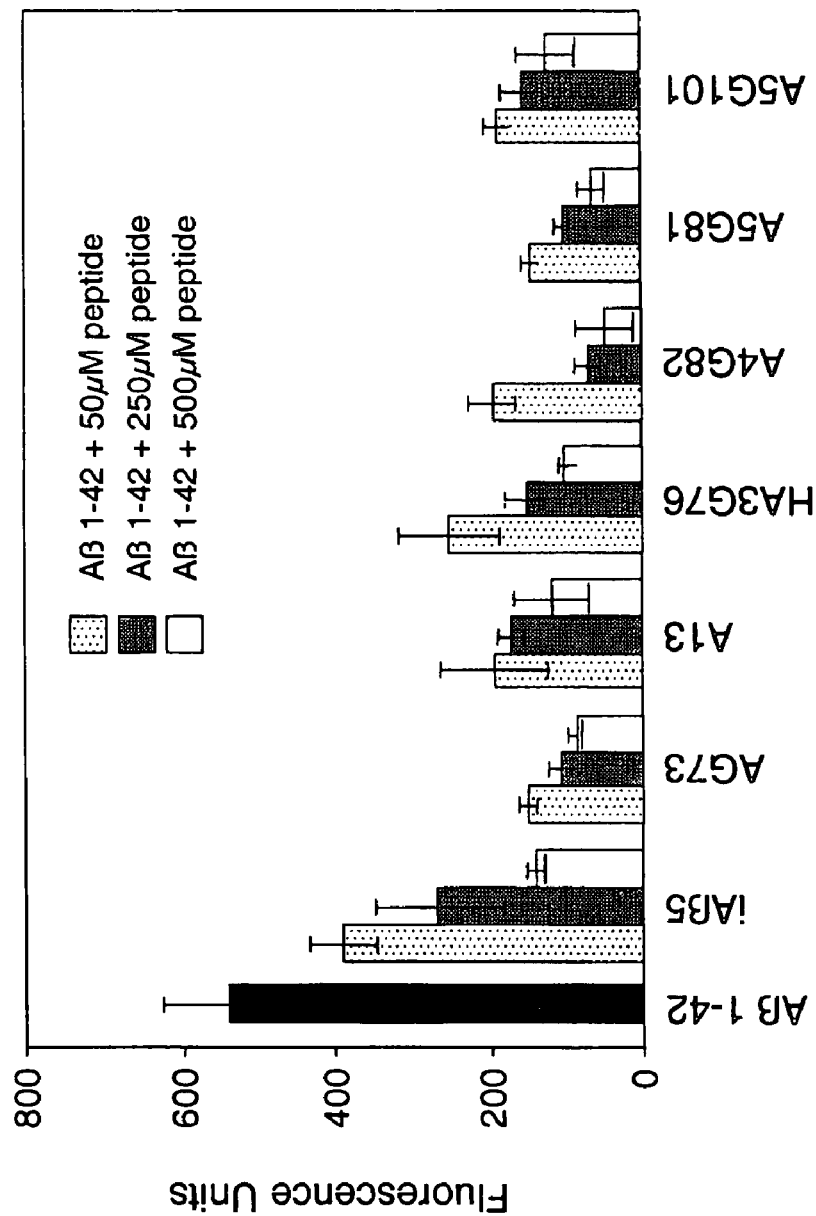
FIG. 10 is a graph demonstrating dose-dependent disruption/disassembly of pre-formed Aβ 1-42 fibrils by laminin globular domain-derived peptides.
Figure 18:
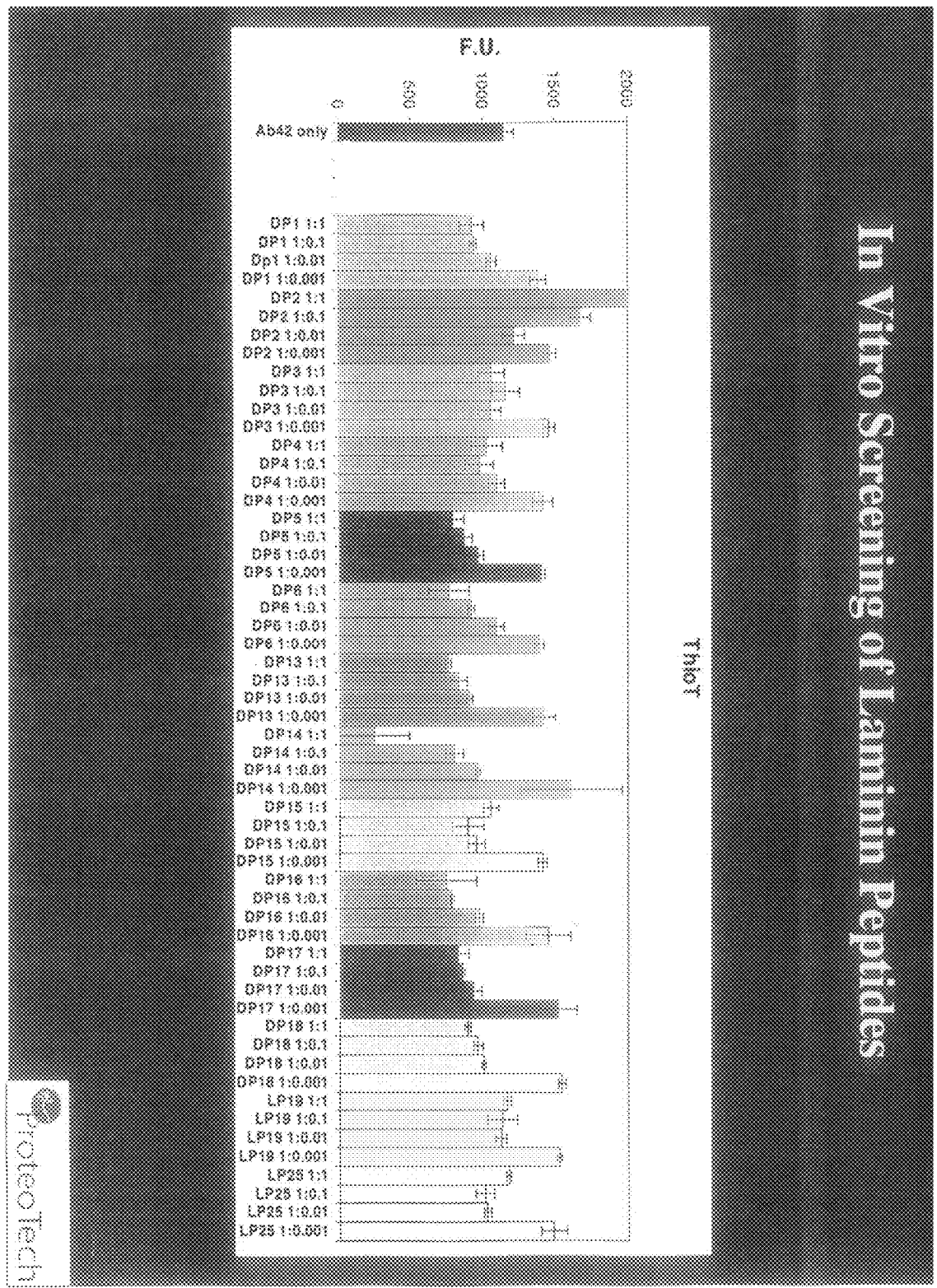

FIG. 10 is a graph demonstrating dose-dependent disruption/disassembly of pre-formed Aβ 1-42 fibrils by laminin globular domain-derived peptides.

FIGS. 12A-F are laminin peptide sequences for 12-13 mer peptides DP1-18 and LP19-25, and 7 mer peptides DP 26-49.

FIG. 13 is a graph of in vitro screening of peptides DP1-6, DP13-18, and LP19, 25 demonstrating their effects on inhibition of Ab 1-42 amyloid fibrils (Alzheimer's Disease) as assessed by a Thioflavin T fluorometry assay.

FIG. 14 is a graph of in vitro screening of peptides DP1-6, DP13-18, and LP19, 25 demonstrating their effects on inhibition of Ab 1-42 amyloid fibrils as assessed by a Congo Red binding assay.

FIG. 15 is a graph of in vitro screening of peptides DP2, 14, 7-12, LP 19, 25, AG73, A4G82, iAβ5, and A5G101 demonstrating their effects on inhibition of Ab 1-42 amyloid fibrils as assessed by a Thioflavin T fluorometry assay.

FIG. 16 is a graph of in vitro screening of peptides DP2, 14, 7-12, LP 19, 25, AG73, A4G82, iAβ5, and A5G101 demonstrating their effects on inhibition of Ab 1-42 amyloid fibrils as assessed by a Congo Red binding assay.

FIG. 17A-D are graphs of peptides DP1-2 demonstrating their effects on inhibition of Aβ 1-42 amyloid fibrils as assessed by circular dichroism spectroscopy (CD).

FIG. 18A-D are graphs of peptides DP3-4 demonstrating their effects on inhibition of Aβ 1-42 amyloid fibrils as assessed by CD.

FIG. 19A-D are graphs of peptides DP5-6 demonstrating their effects on inhibition of Aβ 1-42 amyloid fibrils as assessed by CD.

FIG. 20A-D are graphs of peptides DP7-8 demonstrating their effects on inhibition of Aβ 1-42 amyloid fibrils as assessed by CD.

FIG. 21A-D are graphs of peptides DP9-10 demonstrating their effects on inhibition of Aβ 1-42 amyloid fibrils as assessed by CD.

FIG. 22A-D are graphs of peptides DP11-12 demonstrating their effects on inhibition of Aβ 1-42 amyloid fibrils as assessed by CD FIG. 23A-D are graphs of peptides DP13-14 demonstrating their effects on inhibition of Aβ 1-42 amyloid fibrils as assessed by CD.

FIG. 24A-D are graphs of peptides DP15-16 demonstrating their effects on inhibition of Aβ 1-42 amyloid fibrils as assessed by CD.

FIG. 25A-D are graphs of peptides DP17-18 demonstrating their effects on inhibition of Aβ 1-42 amyloid fibrils as assessed by CD.

FIG. 26A-B are graphs of peptide LP19 demonstrating its effects on inhibition of Aβ 1-42 amyloid fibrils as assessed by CD.

EXAMPLES

The following examples are provided to disclose in detail preferred embodiments of the potent inhibitory effects of laminin fragments, and laminin globular domain-derived peptides on Aβ fibrillogenesis. However, it should not be construed that the invention is limited to these specific examples.

Example 1

Screening of Peptides from the Globular Domain Regions of Different Laminin Chains A series of overlapping 12-14 amino acid peptides against the globular domain regions of the alpha-1, alpha-3 (FIG. 5), alpha-4 (FIG. 6) and alpha-5 (FIG. 7) chain of laminin were synthesized. More than 300 (12-14 amino acid) peptides corresponding to the globular domain regions of the various laminin chains were synthesized manually using the 9-fluorenylmethoxy-carbonyl (FMOC) method and C-terminal amides. The respective amino acids were condensed manually in a stepwise manner using 4-(2",4"-dimethoxyphenyl-FMOC-amino-methyl)-phenoxy resin (Rink, *Tetrahedron Lett.* 28:3787-3790, 1987). The amino acid side chain protecting groups were removed as described previously (Nomizu et al, *J. Biol. Chem.* 269:30386-30392, 1994; *J. Biol. Chem.* 270: 20583-20590, 1995). The resulting protected synthetic peptide resins were de-protected and cleaved from the resins using trifluoroacetic acid-thianisole-m-cresol ethanedithiol-$H_2O$ (80:5:5:5:5) at 20° C. for 3 hours. Crude peptides were then precipitated and washed with ethyl ether and purified by reverse phase HPLC using a Vydac 5C18 column with a gradient of water/acetonitrile containing 0.1% trifluoroacetic acid. The purity of the peptides was confirmed by analytical HPLC. The identity of each peptide was confirmed using a Sciex API IIIE triple quadruple ion spray mass spectrometer (Otaka et al *J. Org. Chem.* 60:3967-3974, 1995). More than 300 peptides were synthesized for Aβ amyloid inhibitory activity screening using Thioflavin T fluorometry (Castillo et al *J. Neurochem.* 69:2452-2465, 2000). For initial screening studies, 25 μM of pre-formed Aβ 1-40 fibrils were incubated for 7 days with various 12-14 amino acid laminin globular domain-derived peptides at an Aβ:peptide molar ratio of 1:6. Of 300 peptides screened, only 30 peptides (listed in FIG. 8) were found to demonstrate a disruption/disassembly greater than 20%. The significance was determined using the paired t-test and comparing fluorescence units ±S.D. (n=3) of Aβ alone versus Aβ +laminin-derived peptides.

Example 2

Laminin Globular Domain Peptides that Disrupt/Disassemble Pre-Formed Aβ Fibrils

FIG. 8 lists 30 laminin globular domain peptides that were able to cause a disruption/disassembly of pre-formed Aβ 1-42 fibrils. These Alzheimer's amyloid inhibitor peptides included 3 peptides from the laminin alpha-1 chain globular domain (peptides AG73, LAM-L, and A13; FIG. 8), 1 peptide from the laminin gamma-1 chain (peptide C-16; FIG. 8), 11 peptides from the laminin alpha-3 chain globular domain (peptides A3; HA3G45; HA3G47; HA3G58; HA3G67; HAG371; HAG374; HAG375; HAG376; HAG379, and HAG383; FIG. 8), 2 peptides from the laminin alpha-4 chain globular domain (peptides A4G31 and A4G82; FIG. 8), and 12 peptides from the laminin alpha-5 chain globular domain (peptides A5; A5G15; A5G35; A5G46; A5G46; A5G56; A5G71; A5G80; A5G81; A5G82; A5G84; A5G101; A5G109 and A5G110; FIG. 8).

Example 3

Further Testing of Selected Laminin Globular Domain-Derived Peptides for Aβ 1-42 Amyloid Fibril Inhibitory Activity From the screening results shown in Example 2 and FIG. 8, 19 peptides (out of >300 screened) were identified that were effective in causing a >25% disruption/disassembly of pre-formed Aβ 1-40 fibrils. These included peptides AG73 (SEQ ID NO:1), C-16 (SEQ ID NO: 2), A-13 (SEQ ID NO:3), HA3G47 (SEQ ID NO: 4), HA3G58 (SEQ ID NO: 5), HA3G67 (SEQ ID NO: 6), HA3G74 (SEQ ID NO: 7), HA3G76 (SEQ ID NO: 8), HA3G79 (SEQ ID NO: 9), HA3G83 (SEQ ID NO: 10), A4G82 (SEQ ID NO: 11), A5G15 (SEQ ID NO: 12), A5G56 (SEQ ID NO: 13), A5G80 (SEQ ID NO: 14), A5G81 (SEQ ID NO: 15), A5G82 (SEQ ID NO: 16), A5G84 (SEQ ID NO:17), A5G101 (SEQ ID NO: 18) and A5G109 (SEQ ID NO: 19) (Sequence Group A).

These selected laminin globular domain-derived peptides were then tested for their effectiveness to also disrupt/disassemble pre-formed Aβ 1-42 fibrils (FIG. 9). In this latter study, selected laminin globular domain-derived peptides were incubated with pre-formed Aβ 1-42 fibrils at an Aβ:peptide molar ratio of 1:10. Direct comparisons were made to iAβ5, a 5 amino-acid (LPFFD; SEQ ID NO: 41) Aβ inhibitor previously identified as a potent inhibitor of Aβ fibrillogenesis (Soto et al, *Nature Med.* 4:822-826, 1998). The results demonstrate that six laminin globular domain-derived peptides were significantly more effective than iAβ5 in causing a disruption/disassembly of preformed Aβ 1-42 fibrils (FIG. 9). These laminin-derived peptides included peptides from the laminin alpha-1 chain [(i.e. AG73—SEQ ID NO:1; A 13-SEQ ID NO 3), the laminin alpha-3 chain (i.e. HA3G76—SEQ ID NO:8), the laminin alpha-4 chain (i.e. A4G82—SEQ ID NO: 11) and the laminin alpha-5 chain (i.e. A5G81—SEQ ID NO:15; A5G101-SEQ ID NO: 18). It should be noted that two of these Aβ inhibiting peptides were derived from the globular domain of the laminin alpha-1 chain, and the more effective of these two peptides (i.e. AG73-SEQ ID NO:1) was precisely located within the 4th globular domain of the laminin-1 chain, and found to bind very tightly to Aβ (FIG. 8). In our studies (described above), the AG73 (SEQ ID NO:1) peptide disrupted Aβ 1-42 fibrils by 81% when used at an Aβ:peptide molar ratio of 1:10. In comparison, this peptide was 31% more effective than the previously described iAβ5 peptide (Soto et al, *Nature Med.* 4:822-826 1998), which in our studies only dissociated pre-formed Aβ 1-42 fibrils by 50%. At an Aβ:peptide molar ratio of 1:2, the AG73 peptide (SEQ ID NO:1) was also found to disrupt/disassemble pre-formed Aβ 1-42 fibrils by 72%, whereas the iAβ5 peptide only caused a 27% disruption/disassembly (FIG. 9). The other laminin fragment reported in the literature (Monji et al, *Neurosc. Lett.* 251:65-68, 1998) required an Aβ:peptide molar ratio of 1:10 to obtain a 50% inhibition of Aβ fibril formation, whereas our newly identified AG73 peptide (SEQ ID NO:1) only required an Aβ:peptide molar ratio of 1:1 to achieve the same level of inhibition. Assuming that the 12-amino acid peptide, AG73 (SEQ ID NO:1), represents a single-site of Aβ binding, we can be confident that we are close to theoretically optimum inhibition. During this screening process, we also identified 5 other peptides in the alpha 3, 4, and 5 chains that were most effective in disrupting/causing a disassembly of pre-formed Aβ fibrils (see FIG. 8).

Example 4

Dose-Dependent Disassembly of Pre-Formed Aβ 1-42 Fibrils by Laminin Globular Domain-Derived Peptides The next study was implemented to determine whether the six selected laminin globular domain-derived peptides were capable of causing a dose-dependent disassembly/disruption of pre-formed AD amyloid fibrils containing Aβ 1-42. As shown in FIG. 10, disruption of pre-formed AD amyloid fibrils by all six selected laminin-derived peptides occurred following a 7-day incubation period, and in a dose-dependent manner. Significant (p<0.001) disassembly/disruption of pre-formed AD amyloid fibrils containing Aβ 1-42 was observed in the presence of laminin globular domain-derived peptides and iAβ5. Whereas iAβ5 was effective at all molar ratios tested, the selected laminin peptides were more potent (p<0.05) than iAβ5 at Aβ:peptide molar ratios of 1:2 and 1:10, with the laminin globular domain derived-peptides showing a range of inhibition from 53-87% compared to a range of inhibition from 27-50% for iAβ5. At an Aβ:peptide molar ratio of 1:20, the laminin-derived peptides AG73 (SEQ ID NO:1), HA3G76 (SEQ ID NO:8), A5G81 (SEQ ID NO:15), A4G82 (SEQ ID NO:11) were all still significantly (p<0.001) more effective than iAβ5. Both A5G101 (SEQ ID NO:18) and A13 (SEQ ID NO:3) have a similar effectiveness to iAβ5 at an Aβ:peptide molar ratio of 1:20. This study therefore demonstrated that we have identified specific candidate laminin globular domain-derived peptides that caused a disassembly/disruption of pre-formed AD amyloid fibrils in a dose-dependent manner following a 7-day incubation.

Example 5

Synthesis of Laminin Globular Domain Analogs

Laminin globular domain-derived peptides (as described above) can be produced in both the L- and D-amino acid forms. In addition, truncated peptides and peptide analogs can be assembled for use as potential potent therapeutic peptides for the treatment of Aβ fibrillogenesis in Alzheimer's disease and related disorders. These peptides can be produced by methods well known to one skilled in the art. For example, L- and D-laminin globular domain-derived peptides could be synthesized on peptide synthesizers known to those skilled in the art, such as an Advanced ChemTech Model 396 multiple peptide synthesizer (Louisville, Ky.) using an automated protocol established by the manufacturer for 0.025 mmole scale synthesis. Double couplings are performed on all cycles using 2-(1H-benzotriazol-1-yl)-1,1,3,3-tetramethyluronium hexafluorophosphate (HBTU)/N,N-diisopropylethylamine (DIEA)/HOBt/FMOC-AA in four-fold excess for 30 minutes followed by DIC/HOBt/FMOC-AA in fourfold excess for 45 minutes. The peptide is then deprotected and removed from the resin by treatment with TFA/water (95%/5%) for 3 hours and then precipitated with cold ether. The resulting solid is pelleted by centrifugation (2400 rpm×10 min), and the ether is discarded. The solid is then be re-suspended in ether and re-centrifuged for the second time after which the ether is decanted for the second time. The solid is dissolved in 10% acetic acid and lyophilized to dryness (~30 mg for 12 amino acid peptides; 18 mg for 7 amino acid peptides). The crude peptide is purified by preparative HPLC using instruments known to those skilled in the art such as a HP 1100 series with diode array detector, with a Vydac C18 column (21× 250 mm) using a 15%-40% acetonitrile gradient over 80 minutes, at a flow rate of 5 ml/min. The primary fraction is collected and re-analyzed for purity using analytical HPLC to ensure a single symmetrical peak at all wavelengths. The confirmation of structures and sequences is based on comparison of predicted molecular weights to molecular weights obtained by mass spectroscopy. These analyses are performed using instruments known to those skilled in the art, such as a Sciex API IIIE triple quadruple ion spray mass spectrometer, for example.

Laminin globular domain derived 12-13 amino acid peptides showing the more favorable Aβ amyloid inhibitory activity as described in Examples above include, but are not limited to:

1) AG73 RKRLQVQLSIRT (Arg-Lys-Arg-Leu-Gln-Val-Gln-Leu-Ser-Ile-Arg-Thr) SEQ ID NO: 1

2) A13 RQVFQVAYIIIKA (Arg-Gln-Val-Phe-Gln-Val-Ala-Tyr-Ile-Ile-Ile-Lys-Ala) SEQ ID NO: 3

3) HA3G76 YLSKGRLVFALG (Tyr-Leu-Ser-Lys-Gly-Arg-Leu-Val-Phe-Ala-Leu-Gly) SEQ ID NO: 8

4) A4G82 TLFLAHGRLVFM(Thr-Leu-Phe-Leu-Ala-His-Gly-Arg-Leu-Val-Phe-Met) SEQ ID NO: 11

5) A5G81 AGQWHRVSVRWG (Ala-Gly-Gln-Trp-His-Arg-Val-Ser-Val-Arg-Trp-Gly) SEQ ID NO: 15, and 6) A5G101 DGRWHRVAVIMG (Asp-Gly-Arg-Trp-His-Arg-Val-Ala-Val-Ile-Met-Gly) SEQ ID NO: 18.

These laminin globular domain-derived peptides, such as the six just above from Sequence Group B, can be synthesized using L- or D-amino acids.

Once the above peptides are made, their D-amino acid forms and their parent L-amino acid forms may advantageously be assayed in vitro for amyloid inhibitory activity as described below. Those that are found to be efficacious are analyzed further in a number of different in vitro assays such as, to determine their binding affinity to Aβ, their ability to inhibit Aβ-Aβ self interactions (using a solid phase immunoassay), their effects on disruption/disassembly of β-pleated sheet (using Thioflavin T fluorometry, Congo Red binding assay, and circular dichroism spectroscopy), and their ability to inhibit Aβ fibril formation (by electron microscopy). Peptides that are active are further tested in cell culture for cellular toxicity, and for their potential to inhibit Aβ-induced neurotoxicity. If incorporation of tyrosine is found to reduce amyloid inhibitory activity, this step can be stepped by using a radio labeled D-amino acid as one of the reagents during synthesis to enhance biostability.

Active peptides can be linked to polyamine (putrescine, spermidine, or spermine) at the carboxy-terminal ends (Poduslo and Curran, *J. Neurochem.* 67:734-741, 1996) using the following procedure, as an example. Briefly, 2 ml of 0.4 M polyamine (putrescine, spermidine, or spermine), pH 4.7 (adjusted with HCl) is used to dissolve 1 mg of peptide. To this, 0.2 g of water-soluble 1-ethyl-3-(3-dimethylaminopropyl)carbodiamide is added. The reaction is stirred for 4 hours at room temperature and maintained at pH 4.7. The solution is purified by preparative HPLC, using instruments known to those skilled in the art, such as a HP 1100 series with diode array detector, with Vydac C18 column (21×250 mm) using 15%-40% acetonitrile gradient over 80 minutes at a flow rate of 5 ml/min. Peptide peaks are pooled and lyophilized for further analysis. Some of the peptides ((those containing glutamate (E) or aspartate (D)) have a variable number of polyamines attached to them and thus are pooled separately from those containing one polyamine. The number of polyamines is determined based on the molecular weight increase from the parent peptide as determined, using instruments known to those skilled in the art, such as a Sciex API IIIE triple quadruple ion spray mass spectrometer. The polyamine-linked forms of peptides can also be assayed for amyloid-inhibitory activity (described below). Further truncation of peptides can be performed in a similar manner depending on the potency of the resulting 7 amino acid peptide-analogs. Those that are determined to be efficacious are synthesized in labeled forms either by iodination of the tyrosine residues, or during synthesis using radiolabeled amino acids. The bio-stability of polyamine linkages can also be determined using $^{14}C$ labeled polyamine available from Sigma (Sigma Chem. Co. St Louis, Mo., U.S.A.).

For the radio-iodination of peptide's tyrosine residues, the following procedure is used. Briefly, 0.5 mg of lyophilized peptides in a microcentrifuge tube is dissolved in 200 µl of 0.5M phosphate buffer (pH 7.4), and Na $^{125}I$ solution (2-10 µl; 0.2-1.0 mCi; ICN) is added. The iodination reaction is initiated by the addition of IodoBeads (Pierce, Rockford, Il). The tubes will be capped and left at room temperature. After 15 minutes, the reactions are stopped by removing the Iodo-Beads. The $^{125}I$-labeled peptides are then applied to 1 gm of C18 sorbent (Varian Bond ElutOSPE column, Walnut Creek, Calif.) and washed with 10 volumes of water containing 0.1% (w/v) cold iodine. Labeled peptides are then be eluted with 3 volumes of 50% (v/v) acetonitrile water, and the radioactivity is determined using instruments known to those skilled in the art, such as a MicroBeta TRILUX liquid Scintillation and luminescence counter (Wallac, Turku, Finland), and the radiolabeled peptides are lyophilized.

Example 6

In Vitro Testing to Determine Efficacy of Laminin Globular Domain-Derived Peptides as Aβ Amyloid Inhibitory Agents The following are in vitro screening assays which are examples of testing procedures to determine the efficacy of L- and D-laminin globular domain derived peptides and analogs, as potential Aβ amyloid inhibitory agents.

Thioflavin T Fluorometry Assays

Inhibition of Aβ fibril formation: Various peptides synthesized as outlined above can be tested for potential Aβ amyloid inhibitory activity using in vitro assays. Thioflavin T fluorometry, which measures the amount of amyloid fibrils formed (LeVine III, *Protein Sci.* 2:404-410, 1993; *Amyloid: Int. J. Exp. Clin. Invest.* 2:1-6, 1995; Naiki and Nakakuki, *Lab. Invest.*, 74:374-383, 1996; Castillo et al, *J. Neurochem.* 69:2452-2465, 1997) can first be used to identify synthetic peptides capable of inhibiting Aβ 1-40 amyloid fibril formation. For these studies, 25 µM of Aβ 1-40 (Bachem Inc) is incubated in microcentrifuge tubes at 37° C. for 1 week (in triplicate), either alone, or in the presence of 25 µM, 50 µM or 250 µM of parent peptides or peptide-analogs (at Aβ:peptide molar ratios of 1:1; 1:2 and 1:10- or alternatively Aβ:peptide weight/weight ratios of 1:1, 1:0.1, 1:0.01, 1:0.001) in 150 mM Tris HCl, 10 mM NaCl, pH 7.0 (TBS). 50 µl aliquots are taken for analysis at 1 hour, 1 day, 3 days and 1 week and added to 1.2 ml of 100 µM Thioflavin T and 50 mM NaPO4 (pH 6.0), respectively. Fluorescence emission at 480 nm is measured on a Turner model 450 fluorometer at an excitation wavelength of 450 nm. For each determination, the fluorometer is calibrated by zeroing in the presence of the Thioflavin T reagent alone, and by setting the 50 ng/ml riboflavin (Sigma) in the Thioflavin T reagent to 1800 fluorescence units. All fluorescence determinations are based on these references and any fluorescence given off by peptides in the presence of the Thioflavin T reagent is always subtracted from all pertinent readings. Our experience indicates that Thioflavin T does not give off any false fluorescence in the presence of laminin-derived peptides, nor do these peptides cause any quenching problems. Previous studies have also indicated that increasing concentrations of fibrillar Aβ gives a proportional increase in fluorescence in the presence of 100 µM Thioflavin T, ruling out the presence of any disproportionate inner filter effects at this Thioflavin T concentration (Castillo et al *J. Neurochem.* 69:2452-2465, 1997).

Disruption/Disassembly of Pre-formed Aβ Amyloid Fibrils: One can also determine the dose-dependent ability of laminin globular domain-derived peptides (and peptide analogs) to disrupt/disassemble preformed Aβ 1-40 and 1-42 fibrils. In these studies the peptides identified as inhibitors of Aβ 1-40 amyloid fibril formation (as described above) are used. For studies involving fibrillar Aβ 1-40, 1 mg of Aβ 1-40 (Bachem Inc) is dissolved in 1.0 ml of double distilled water (1 mg/ml solution) and then incubated at 37° C. for 1 week to cause abundant fibril formation. Aβ 1-42, which is already fibrillar, does not require pre-incubation at 37° C. (as with Aβ 1-40), and is utilized immediately. For all of these studies, 25 µM of fibrillar amyloid (Aβ 1-40 or Aβ 1-42 is incubated in the presence of 150 mM Tris-HCl, 10 mM NaCl (pH 7.0), in the presence or absence of 25 µM, 50 µM, 125 µM and 250 µM of the various parent peptides or peptide-analogs previously synthesized, giving approximate Aβ:peptide molar ratios of 1:1, 1:2, 1:5, 1:10. All samples, including controls (i.e. Aβ only, blank only or test-compound only) are tested in triplicate. Following an overnight, 3-day or 7-day incubation at 37° C., 50 µl aliquots are added to 1.2 ml of 100 µM Thioflavin T (Sigma) in 50 mM NaPO4 (pH 6.0) for fluorometry readings as described above.

Statistical Analysis: For the fibril formation/disruption assays as described above, comparisons of Aβ 1-40 or Aβ 1-42 in the presence or absence of peptides is based on paired Student's t tests with data shown as mean +/−S.E., or ANOVA, depending on the particular study. Significance is reported at the 95% ($p<0.05$), 99% ($p<0.01$), and 99.9% ($p<0.001$) confidence levels.

Congo red Staining Assays: Aliquots (5 µl) from the incubation assays as described above are also be analyzed by air-drying aliquots on gelatin-coated slides, followed by Congo red staining (Puchtler et al, *J. Histochem. Cytochem.* 10:355-364, 1962). This technique has been effective in providing corroborating evidence of potential Aβ amyloid fibril inhibitors. A decrease in Congo red staining (i.e. red/green birefringence as viewed under polarized light) of fibrillar Aβ amyloid in the presence of peptides will confirm that a disruption/disassembly of amyloid fibril architecture has taken place. Further analysis of the most potent peptides identified at the light microscopic level will also analyzed by negative stain electron microscopy as described below.

Negative Stain Electron Microscopy: Laminin globular domain-derived peptides (or peptide analogs) able to inhibit Aβ 1-40 fibril formation, and disrupter/disassemble preformed Aβ 1-42 fibrils, as determined by Thioflavin T fluorometry and Congo red staining assays, (as described above), can be confirmed by negative stain electron microscopy. For confirmation of inhibition of Aβ 1-40 fibril formation, laminin globular domain-derived peptides (or peptide analogs) are incubated with 50 μM of freshly solubilized Aβ 1-40 (Bachem) at Aβ:peptide molar ratios of 1:1, 1:2 and 1:10, for increasing times (i.e. 0 hours, 1 day, 3 days and 7 days) to observe any time-dependent and dose-dependent inhibition of Aβ 1-40 fibril formation. Comparisons are made to Aβ 1-40 only. Negatively stained Aβ fibrils are prepared by floating pioloform, carbon-coated grids on peptide solutions (200 μg/ml of Aβ 1-40) in the presence of absence of various concentrations of laminin globular domain-derived peptides (as described above). To control for pH changes, peptides are dissolved in buffered solutions of 20 mM glycine (for pH 2 to 3 and pH 9 to 10) or 20 mM Tris-HCl (for pH 6 to 8). After the grids are blotted and air-dried, the samples are stained with either 2% (w/v) uranyl acetate or 1% (w/v) phosphotungstic acid and visualized, and photographed, with instruments known to those skilled in the art, such as a Phillips CM-10 electron microscope, using 80 kv accelerating voltage. The ability of peptides to disrupt the structure of amyloid fibrils can be qualitatively determined. In another study, negative stain electron microscopy can be utilized to confirm which laminin globular domain-derived peptides (or peptide analogs) are effective in disruption/disassembly of pre-formed Aβ 1-42 fibrils. For these studies, 50 μM of fibrillized Aβ 1-42 (prepared fresh) is incubated with laminin globular domain-derived peptides (or peptide analogs) at Aβ:peptide molar ratios of 1:1, 1:2 and 1:10 at 37° C. for 7 days. Aliquots are taken at 0, 1, 3, and 7 days of incubation for analysis by negative stain electron microscopy as described above. Inhibitors/disruptors of Aβ fibrillogenesis are identified by their ability to form amorphous non-fibrillar material. High magnification measurements (i.e. 100,000×) of Aβ amyloid fibrils (fibril diameter usually 7-10 nm) are compared to materials observed at 7 days following incubation with different peptides (as described above).

Example 7

Further In Vitro Testing to Determine Efficacy of Laminin Globular Domain-Derived Peptides as Aβ Amyloid Inhibitory Agents The following are further in vitro screening assays which are examples of testing procedures to determine the efficacy of the D-forms of laminin globular domain derived peptides and analogs as potential Aβ amyloid inhibitory agents.

FIGS. 12*a-f* are laminin peptide sequences for the following peptides that are the subject of these discussions and of FIGS. 13-26 herein. In the following tables and discussion, L is the L-form of the peptide, D (or D-) is used to denote, or as a prefix for, the D-form of the peptide (as distinguished from the L-form of the same peptide), D-R (or D-R-) is used to denote, or as a prefix for, the D-R-form of a D-form peptide, where the D-R-form is the reverse form of the D-peptide. Through the remainder of peptide efficacy discussion herein, peptides may be referred to either in the standard positional nomenclature (such as A5G101), with or without a D- or L-prefix (such as D-A5G101), or as the peptide's corresponding D-form peptide (DP) specimen number (such as DP6), or as the peptide's corresponding L-form peptide (LP) specimen number (such as LP24), or as the reverse D-form peptide's corresponding (DP) specimen number (such as DP18) and/or its standard reverse positional nomenclature (such as D-R-A5G101), or any combination of these.

| Peptide designation | D | D-R | L |
| --- | --- | --- | --- |
| AG73 | DP1 | DP13 | LP19 |
| A13 | DP2 | DP14 | LP20 |
| HA3G82 | DP3 | DP15 | LP21 |
| A4G82 | DP4 | DP16 | LP22 |
| A5G81 | DP5 | DP17 | LP23 |
| A5G101 | DP6 | DP18 | LP24 |

LP25 herein is synonymous with iAβ5. In addition 6 new 12-13 mer D-form

| Peptide | D |
| --- | --- |
| HA3G47 | DP7 |
| HA3G58 | DP8 |
| HA3G74 | DP9 |
| HA3G83 | DP10 |
| A5G82 | DP11 |
| A5G109 | DP12 |

A5G81 (DP5) also has six 7 mer truncations labeled DP26-31; A5G101 (DP6) has six 7 mer truncations labeled DP32-37; A4G82 (DP4) has six 7 mer truncations labeled DP38-38; and rHA3G76 (DP15, reverse DP3) has six 7 mer truncations labeled DP44-49.

Dose-Dependent Disassembly/Disruption of Pre-Formed Aβ 1-42 Fibrils by Selected Laminin Globular Domain Derived Peptides Thioflavin T fluorometry (ThioT), Congo Red (CR) and circular dichroism (CD) spectroscopy methods (see FIGS. 13-26) were used to assess the potential disruption ability of laminin globular domain derived peptides (12-13 mers) on pre-formed Aβ 1-42 fibrils (an important therapeutic target for Alzheimer's disease and other beta amyloid diseases). Testing of the top 6 laminin derived-peptides (including AG73, A13, HA3G76, A4G82, A5G81 and A5G101) and comparisons to the potential inhibitory activity of iAβ5 were determined. By Thioflavin T fluorometry, the results demonstrated that many of these laminin globular domain derived-peptides showed significant inhibition compared to iAβ5 (LP25). Additionally, circular dichroism spectroscopy studies (FIGS. 17-26) were implemented to confirm the results obtained by Thioflavin T fluorometry.

Circular dichroism (CD) spectroscopy is an effective means to assess whether one mechanism of action involves the test compound's ability to disrupt the β-pleated sheet secondary structure present in Aβ fibrils. In on study, the typical pattern of a predominant β-pleated sheet structure (with a minima at 218 nm) was observed with Aβ 1-42 fibrils following 3 days of incubation (see FIGS. 17*a* through 26*a*). No observable effect on disruption of β-sheet in Aβ 1-42 fibrils was found for iAβ5 at an Aβ42:iAβ5 molar ratio of 1:5. In contrast, for example, laminin derived-peptide DP1 AG73, showed a marked disruption of β-sheet structure as observed in a decrease in the minima band at 218 nm. A similar disruption of Aβ 1-42 fibrils was observed with laminin derived-peptide DP5 A5G81, and to a lesser extent when using laminin derived peptide DP4 A4G82. Other favorably acting peptides include DP3, 6-7, 9-10, 12-13 and 15-18. Similar observations were obtained using fourier transform infrared (FTIR) spectroscopy, wherein it was observed that the indicated laminin derived peptides also significantly disrupted the β-sheet of Aβ 1-42 fibrils, and iAβ5 had no observable effect. These studies indicate that the selected 12-13 mer laminin derived peptides (in D-amino acid form) are effective as Aβ fibril disrupters and that one potential mechanism of action is disruption of β-sheet secondary structure characteristic of Aβ amyloid fibrils.

Synthesis of D-Form Laminin Globular Domain-Derived Peptides

We have now synthesized the D-form of the 6 parent 12-13 amino acid peptides discussed above as Sequence Group B (all L-forms) as showing superior Aβ amyloid inhibitory activity. Since we earlier tested the L-form of each of the 6 laminin derived peptides, we chose to synthesize the D-amino acid form of the same 6 laminin derived peptides. Those D-form amino acids synthesized are: DP1) AG73 (RKRLQVQLSIRT) (SEQ ID NO: 1), DP2) A13 (RQVFQVAYIIKA) (SEQ ID NO: 3), DP3) HA3G76 (YLSKGRLVFALG) (SEQ ID NO: 8), DP4) A4G82 (TLFLAHGRLVFM) (SEQ ID NO: 11), DP5) A5G81 (AGQWHRVSVRWG) (SEQ ID NO: 15), and DP6) A5G101 (DGRWHRVAVIGM) (SEQ ID NO: 18). The D amino acid form of these peptides is believed to offer some therapeutic advantage over L-form peptides, since the D amino acid peptides are known to be more resistant to in vivo protease degradation. In addition, the reverse sequences (DP13-18) of all 6 D-form peptides described above were also synthesized to determine if reversing the sequence alters potential Aβ amyloid inhibitory activity. Lastly, a group of another 6 D amino acid 12-13 mer peptides (DP7-12) were also synthesized, and these represents 6 additional laminin derived peptides (also already tested in L amino acid form) that were only somewhat less effective than the first 6 peptides described above, still maintaining >25% Aβ fibril disrupting ability.

The six peptides from Sequence Group B, in either L- or D-form can be truncated into shorter 5 to 7 L- or D-amino acid peptides (for example) with or without tyrosine at the C-terminal end.

For example, representative DP1 D-AG73 peptide truncations (the resulting 7 L- or D-amino acid peptides synthesized and tested for amyloid inhibitory activity) are RKRLQVQ(Y) (SEQ ID NO: 66), KRLQVQL(Y) (SEQ ID NO: 67), RLQVQLS(Y) (SEQ ID NO: 68), LQVQLSI(Y) (SEQ ID NO: 69), QVQLSIR(Y) (SEQ ID NO: 70) and, VQLSIRT(Y) (SEQ ID NO: 71).

For example, for DP2 D-A 13 peptide truncation, a resulting (7 L- or D-amino acid) peptides synthesized and tested for amyloid inhibitory activity is RQVFQVA (SEQ ID NO: 72), QVFQVAY (SEQ ID NO: 73), VFQVAYI (SEQ ID NO: 74), FQUVAYII (SEQ ID NO: 75), QYAYIII (SEQ ID NO: 76), VAYIIIK (SEQ ID NO: 77), and AYIIIKA (SEQ ID NO: 78).

For example, for DP3 D-HA3G76 peptide truncation, a resulting (7 L- or D-amino acid) peptides synthesized and tested for amyloid inhibitory activity is YLSKGRL(Y) (SEQ ID NO: 79), LSKGRLV(Y) (SEQ ID NO: 80), SKGRLVF(Y) (SEQ ID NO: 81), KGRLVFA(Y) (SEQ ID NO: 82), GRLVFAL(Y) (SEQ ID NO: 83), and RLVFALG(Y) (SEQ ID NO: 84).

For example, for DP4 D-A4G82 peptide truncation, a resulting (7 L- or D-amino acid) peptides synthesized and tested for amyloid inhibitory activity is DP38 TLFLAHG(Y) (SEQ ID NO: 85), DP39 LFLAHGR(Y) (SEQ ID NO: 86), DP40 FLAHGRL(Y) (SEQ ID NO: 87), DP41 LAHGRLV(Y) (SEQ ID NO: 88), DP42 AHGRLVF(Y) (SEQ ID NO: 89), and DP43 HGRLVFM(Y) (SEQ ID NO: 90).

For example, for DP5 D-A5G81 peptide truncation, a resulting (7 L- or D-amino acid) peptides synthesized and tested for amyloid inhibitory activity is DP 26 AGQWHRV(Y) (SEQ ID NO: 91), DP27 GQWHRVS(Y) (SEQ ID NO: 92), DP28 QWHRVSV(Y) (SEQ ID NO: 93), DP29 WHRVSVR(Y) (SEQ ID NO: 94), DP30 HRVSVRW(Y) (SEQ ID NO: 95), and DP31 RVSVRWG(Y) (SEQ ID NO: 96).

For example, for DP6 D-A5G101 peptide truncation, a resulting (7 L- or D-amino acid) peptides synthesized and tested for amyloid inhibitory is DP 32 DGRWHRV(Y) (SEQ ID NO: 97), DP33 GRWHRVA(Y) (SEQ ID NO: 98), DP34 RWHRVAV(Y) (SEQ ID NO: 99), DP35 WHRVAVI(Y) (SEQ ID NO: 100), DP36 HRVAVIM(Y) (SEQ ID NO: 101), and DP37 RVAVIMG(Y) (SEQ ID NO: 102).

In addition, for DP15 D-R-HA3G76 peptide truncation, a resulting (7 L- or D-amino acid) peptides synthesized and tested for amyloid inhibitory activity is DP44 GLAFVLR(Y) (SEQ ID NO: 103), DP45 LAFVLRG(Y) (SEQ ID NO: 104), DP46 AFVLRGK(Y) (SEQ ID NO: 105), DP47 FVLRGKS(Y) (SEQ ID NO: 106), DP48 VLRGKSL(Y) (SEQ ID NO: 107), and DP49 LRGKSLY(Y) (SEQ ID NO: 108).

As before with the above discussed 12-13 mer peptides, once the above peptides are made, their D-amino acid forms and their parent L-amino acid forms, along with the truncated 7 L- or D-amino acid peptides as described above, may advantageously be assayed in vitro for amyloid inhibitory activity as described herein. Those that are found to be efficacious are analyzed further in a number of different in vitro assays such as, to determine their binding affinity to Aβ, their ability to inhibit Aβ-Aβ self interactions (using a solid phase immunoassay), their effects on disruption/disassembly of β-pleated sheet (using circular dichroism spectroscopy), and their ability to inhibit Aβ fibril formation (by electron microscopy). Peptides that are active are further tested in cell culture for cellular toxicity, and for their potential to inhibit Aβ-induced neurotoxicity. If incorporation of tyrosine is found to reduce amyloid inhibitory activity, this step can be stepped by using a radio labeled D-amino acid as one of the reagents during synthesis to enhance bio-stability.

Thioflavin T Fluorometry Assay

A first set then of 12 synthesized six D-form peptides based upon the top performing six L-form peptides such as A13 discussed above, and respective reverse sequences of the six D-form peptides, was subjected to a battery of tests for potential ability of each tested peptide to disrupt/disassemble Aβ 1-42 fibrils as described above. Twelve laminin-peptides D-AG73 DP1, D-A13 DP2, D-HA3G82 DP3, D-A4G82 DP4, D-A5G81 DP5, D-A5G111 DP6, D-R-AG73 DP13, D-R-A13 DP14, D-R-HA3G76 DP15, D-R-A4G82 DP16, D-R-A5G81 DP17, and D-R-A5G101 DP 18 were tested.

Using a Thioflavin T fluorometry assay of these 12 laminin-derived peptides, the D-form of laminin derived-peptide A13 (as described above) DP2 and its reverse D-form DP14 respectively, were most effective. In one study shown in FIG. 13, 25 μM Aβ 1-42 was incubated with decreasing concentrations of test peptides (at an Aβ:peptide wt/wt ratio of 1:1, 1:0.1, 1:0.01 and 1:0.001) for 3 days. The D-form reverse peptide of A13, D-R-A13 or DP14, was found to disrupt Aβ 1-42 fibrils by 79.1% when incubated at a 1:1 wt/wt ratio, and by 31.2% when incubated at a 1:0.1 wt/wt ratio. In comparison, in this particular study iAβ5, LP25, was found not to significantly disrupt Aβ 1-42 fibrils under the same conditions. The order of 5 of the most effective laminin derived peptides to disrupt Aβ 1-42 fibrils at a 1:1 wt/wt ratio as determined by Thioflavin T fluorometry is D-R-A13 DP14 (79.1%)>D-R-A4G82 DP16 (36%) >D-A5G101 D6 and D-R-AG73 DP13 (both 34%)>D-A5G81 DP5 (32%).

A second set of six synthesized D-form peptides, D-HA3G47 DP7, D-HA3G58 DP8, D-HA3G74 DP9, D-HA3G83 DP10, D-A5G82 DP11, and D-A5G109 DP12, was also subjected to the same test for their potential to disrupt/disassemble Aβ 1-42 fibrils as described above. FIG. 15 shows results of the same Thioflavin T fluorometry assay discussed just above, where 25 μM Aβ 1-42 was incubated with decreasing concentrations of test peptides (at an Aβ:peptide wt/wt ratio of 1:1, 1:0.1, 1:0.01 and 1:0.001) for 3 days. The D-form peptide of HA3G58 DP8 was found to disrupt Aβ 1-42 fibrils by ~75% when incubated at a 1:1 wt/wt ratio, and by ~40% when incubated at a 1:0.1 wt/wt ratio. In comparison, iAβ5, LP25, was found not to significantly disrupt Aβ 1-42 fibrils under the same conditions. The order of 4 of the most effective laminin derived peptides to disrupt Aβ 1-42 fibrils at a 1:1 wt/wt ratio as determined by Thioflavin T fluorometry is D (form) HA3G58 DP8>D-A4G82 DP4=D-A5G101 D6=D-HA3G74 DP9 (all ~50%).

Congo Red Binding Assay

Using a Congo red (CR) binding assay, see FIG. 14, the ability of the 12 synthesized peptides, D-AG73 DP1, D-A13 DP2, D-HA3G82 DP3, D-A4G82 DP4, D-A5G81 DP5, D-A5G101 DP6, D-R-AG73 DP13, D-R-A13 DP14, D-R-HA3G76 DP15, D-R-A4G82 DP16, D-R-A5G81 DP17, and D-R-A5G101 DP18, to inhibit the binding of Congo red to Aβ 1-42 fibrils was also assessed. This assay is another measure of a test peptide's ability to disrupt Aβ fibrils. Superior laminin derived peptide inhibition of CR binding to Aβ 42 fibrils was again found to be D-R-A 13, DP14, which caused a 100% inhibition when used at an Aβ:peptide wt/wt ratio of 1:1, and a 75.1% inhibition when used at a 1:0.1 wt/wt ratio. In comparison, LP25 iAβ5 only inhibited Congo red binding by 39.6% at a 1:1 wt/wt ratio, and by 31.8% when used at a 1:0.01 wt/wt ratio. The order of 5 of the most effective laminin derived peptides to inhibit Congo red binding to Aβ 42 fibrils at a 1:1 wt/wt ratio as determined by this assay is D-R-A 13 DP14 (100%)>D-A 13 DP2 (99%) >D-R-A4G82 DP16 (94.8%)>D-A4G82 DP4 (55.0%)>D-A5G81 DP5 (54.5%). These results obtain notwithstanding that DP2 D-A13 and its reverse peptide DP14 D-R-A13 appear to contain substantial intrinsic β-sheet structure of their own, which is picked up in the ThioT assay.

Using a Congo red (CR) binding assay, see FIG. 16, the ability of the same synthesized peptides, D-HA3G47 DP7, D-HA3G58 DP8, D-HA3G74 DP9, D-HA3G83 DP10, D-A5G82 DP11, and D-A5G109 DP12, as discussed with respect to FIG. 15 to inhibit the binding of Congo red to Aβ 1-42 fibrils was also assessed. Superior laminin derived peptide inhibition of CR binding to Aβ 42 fibrils was found to be HA3G58 DP8 and HA3G83 DP10, both of which caused a 100% inhibition when used at an Aβ:peptide wt/wt ratio of 1:1, and a 100% inhibition when used at a 1:0.1 wt/wt ratio. In comparison, LP25 iAβ5 did not significantly inhibit Congo red binding at a 1:1 wt/wt ratio. The order of 5 of the most effective laminin derived peptides to inhibit Congo red binding to Aβ 42 fibrils at a 1:1 wt/wt ratio as determined by this assay is D-HA3G58 DP8 and D-HA3G83 DP10 (both 100%)>D-R-A13 DP14 (~95%) >D-A5G82 DP11 (~90%)>D-A13 DP2 (~85%).

Circular Dichroism Spectroscopy

Circular dichroism (CD) spectroscopy/FTIR studies and negative stain electron microcopy studies were also done to confirm the potential disruptive/inhibitory effects of the laminin derived peptides as described above. In one CD study the effects of different laminin derived peptides on disruption of Aβ 1-42 fibrils was assessed following a 3-day incubation of test peptides at an Aβ:peptide wt/wt ratio of 1:2 (~1:6 Aβ:peptide molar ratio). The results shown in FIGS. 17-26 demonstrate that DP6 D-A5G101 and DP5 D-A5G81 were most effective in causing an almost complete disruption (i.e. ~95%) of Aβ 1-42 β-sheet structure. Also effective but to a lesser extent (50-60% disruption) were DP17 D-R-A5G81, DP16 D-R-A4G82 and DP14 D-R-A13. As these 3 latter peptides appear to contain intrinsic β-sheet structure of their own (especially DP14 D-R-A13), sometimes making the CD data difficult to interpret. On the other hand, both DP6 D-A5G101 and DP5 D-A5G81 peptides contain little intrinsic β-sheet structure themselves. For further data on amino acid sequences for respective DP numbers 1-18 and CD ellipticity loss, see Table 1 at the end of this specification.

Further Aspects and Utilizations of the Invention

Laminin-Derived Polypeptides

One therapeutic application of the present invention is to use laminin-derived polypeptides as potent inhibitors of Aβ amyloid formation, deposition, accumulation and/or persistence, in Alzheimer's disease, Down's syndrome and other amyloid disorders involving Aβ fibrillogenesis.

The polypeptide referred to above may be a natural polypeptide, a synthetic polypeptide or a recombinant polypeptide. The polypeptides, derivatives or analogs referred to herein may be a) one in which one or more of the amino acid residues are substituted with a conserved or non-conserved amino acid residue and such substituted amino acid residue may or may not be encoded by the genetic code, or b) in which one or more of the amino acid residues includes a substituent group, or c) one in which the mature polypeptide is fused with another compound, such as a compound used to increase the half-life of the polypeptide (for example, polylysine), or d) one in which the additional amino acids are fused to the mature polypeptide, such as a leader or secretory sequence or a sequence which is employed for purification of the mature polypeptide or a proprotein sequence. Such polypeptides, derivatives and analogs are deemed to be within the scope of the invention.

Protein conformation is an essential component of protein-protein, protein-substrate, protein-agonist, protein-antagonist interactions. Changes in the component amino acids of protein sequences can result in changes that have little or no effect on the resultant protein conformation. Conversely, changes in the peptide sequences can have effects on the protein conformation resulting in reduced or increased protein-protein interactions. Such changes and their effects are generally disclosed in *Proteins: Structures and Molecular Properties* by Thomas Creighton, W.H. Freeman and Company, New York, 1984 which is hereby incorporated by reference.

It will be appreciated by those skilled in the art that changes can be made to the disclosed laminin polypeptides, derivatives or analogs, that increase, decrease or otherwise have no effect on the binding of laminin or fragments thereof to Aβ amyloid. In addition, it will be appreciated by those skilled in the art that various post-translational modifications such as phosphorylation, glycosylation and the like, will alter the binding of laminin polypeptides, derivatives or analogs to Aβ amyloid.

The polypeptides of the present invention include the polypeptides described herein, including but not limited to AG73 (SEQ ID NO:1), C-16 (SEQ ID NO:2), A-13 (SEQ ID NO:3), HA3G47 (SEQ ID NO:4), HA3G58 (SEQ ID NO:5), HA3G67 (SEQ ID NO:6), HA3G74 (SEQ ID NO:7), HA3G76 (SEQ ID NO:8), HA3G79 (SEQ ID NO:9), HA3G83 (SEQ ID NO:10), A4G82 (SEQ ID NO:11), A5G15 (SEQ ID NO:12), A5G56 (SEQ ID NO:13), A5G80 (SEQ ID NO:14), A5G81 (SEQ ID NO:15), A5G82 (SEQ ID NO: 16), A5G84 (SEQ ID NO:17), A5G101 (SEQ ID NO:18), A5G109 (SEQ ID NO:19) (Sequence Group A), and fragments thereof, as well as polypeptides which preferably have at least a 70%, and more preferably a 90% identity, to the polypeptides described above. "% Identity" as used herein for peptides means the same amino acids in the same place. Thus a ten amino acid peptide that is identical to another ten amino acid peptide, except for one amino acid, is 90% identical. If a ten amino acid peptide has the same ten amino acids in the same number of each amino acid as another ten amino acid peptide, but two amino acids are juxtaposed with each other, then the two amino acids have an 80% identity with each other, and so forth.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture), or from a virus (such as with the use of phage display techniques known to those skilled in the art). Depending upon the host employed in a recombinant procedure, the polypeptides of the present invention may be glycosylated or may be non-glycosylated. Polypeptides of the invention may also include an initial methionine amino acid residue.

Chemical polypeptide synthesis is a rapidly evolving area in the art, and methods of solid phase polypeptide synthesis are well-described in the following references, hereby entirely incorporated by reference (Merrifield, *J. Amer. Chem. Soc.* 85:2149-2154, 1963; Merrifield, *Science* 232: 341-347, 1986; Fields, *Int. J. Polypeptide Prot. Res.* 35, 161, 1990).

Recombinant production of laminin polypeptides can be accomplished according to known method steps. Standard reference works setting forth the general principles of recombinant DNA technology include Watson, Molecular Biology of the Gene, Volumes I and II, The Benjamin/Cummings Publishing Company Inc., publisher, Menlo Park, Calif. 1987; Ausubel et al, eds., *Current Protocols in Molecular Biology*, Wiley Interscience, publisher, New York, N.Y. 1987; 1992; and Sambrook et al, *Molecular Cloning: A Laboratory Manual*, Second Edition, Cold Spring Harbor Laboratory, publisher, Cold Spring Harbor, N.Y. 1989, the entire contents of which references are herein incorporated by reference.

The polypeptides of the present invention may also be utilized as research reagents and materials for discovery of treatments and diagnostics for human diseases.

Antibodies

Antibodies generated against the polypeptides corresponding to specific sequences recognizing the laminin fragments of the present invention which bind Aβ can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptides from tissue expressing that polypeptide. Preferred embodiments include, but are not limited to, Sequence Group A, and fragments thereof, as well as polypeptides which have at least 70% identity and more preferably a 90% identity to the polypeptides described above.

The term "antibody" is meant to include polyclonal antibodies, monoclonal antibodies, chimeric antibodies, anti-idiotypic antibodies to antibodies specific for laminin-derived protein fragments or polypeptides of the present invention.

Polyclonal antibodies are heterogeneous populations of antibody molecules derived from the sera of animals immunized with an antigen.

A monoclonal antibody contains a substantially homogeneous population of antibodies specific to antigens, which population contains substantially similar epitope binding sites. For preparation of monoclonal antibodies, any technique which provides antibodies produced by continuous cell line cultures can be used. Examples include the hybridoma technique (Kohler and Milstein, *Nature* 256:495-497, 1975), the trioma technique, the human B-cell hybridoma technique (Kozbor et al, *Immunology Today* 4:72, 1983), and the EBV-hybridoma technique to produce human monoclonal antibodies (Cole et al, in *Monoclonal Antibodies and Cancer Therapy*, Alan R. Liss, Inc., pp. 77-96, 1985). Such antibodies may be of any immunoglobulin class including IgG, IgM, IgE, IgA, GILD and any subclass thereof.

Chimeric antibodies are molecules different portions of which are derived from different animal species, such as those having variable region derived from a murine monoclonal antibody and a human immunoglobulin constant region, which are primarily used to reduce immunogenicity in application and to increase yields in production. Chimeric antibodies and methods for their production are known in the art (ex. Cabilly et al, *Proc. Natl. Acad. Sci. U.S.A* 81:3273-3277, 1984; Harlow and Lane: *Antibodies: A Laboratory Manual*, Cold Spring Harbor Laboratory 1988).

An anti-idiotypic antibody is an antibody which recognizes unique determinants generally associated with the antigen-binding site of an antibody. An anti-idiotypic antibody can be prepared by immunizing an animal of the same species and genetic type (e.g., mouse strain) as the source of the monoclonal antibody with the monoclonal antibody to which an anti-idiotypic antibody is being prepared. The immunized animal will recognize and respond to the idiotypic determinants of the immunizing antibody by producing an antibody to these idiotypic determinants (the anti-idiotypic antibody). See, for example, U.S. Pat. No. 4,699,880, which is herein incorporated by reference.

The term "antibody" is also meant to include both intact molecules as well as fragments thereof, such as, for example, Fab and F(ab")$_2$, which are capable of binding antigen. Fab and F(ab")$_2$ fragments lack the Fc fragment of intact antibody, clear more rapidly from the circulation, and may have less non-specific tissue binding than an intact antibody (Wahl et al, *J. Nucl. Med.* 24:316-325, 1983).

The antibodies or fragments of antibodies, useful in the present invention may be used to quantitatively or qualitatively detect laminin-derived fragments in a sample or to detect presence of cells which express a laminin polypeptide of the present invention. This can be accomplished by immunofluorescence techniques employing a flourescently labeled antibody coupled with light microscopic, flow cytometric or fluorometric detection.

One of the ways in which a laminin fragment antibody can be detectably labeled is by linking the same to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorometric, or by visual means. Enzymes which can be used detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colormetric methods which employ a chromogenic substrate for the enzyme. Detection can be accomplished by colormetric methods which employ a chromogenic substrate for the enzyme. Detection can also be accomplished by visual comparison of the extent of enzymatic reaction of a substrate with similarly prepared standards (see Harlow and Lane, *Antibodies: A Laboratory Manual*, Cold Spring Harbor Laboratory 1988; Ausubel et al, eds., *Current Protocols in Molecular Biology*, Wiley Interscience, N.Y. 1987, 1992).

Detection may be accomplished using any of a variety of other immunoassays. For example, by radiolabeling of the antibodies or antibody fragments, it is possible to detect R-PTPase through the use of a radioimmunoassay (RIA). A good description of RIA may be found in *Laboratory Techniques and Biochemistry in Molecular Biology*, by Work et al, North Holland Publishing Company, NY (1978) with particular reference to the chapter entitled "An Introduction to Radioimmune Assay and Related Techniques" by Chard, incorporated entirely by reference herein. The radioactive isotope can be detected by such means as the use of a gamma-counter, a scintillation counter or by autoradiography.

It is also possible to label a laminin fragment polypeptide antibody with a fluorescent compound. When the flourescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine, commercially available, e.g., from Molecular Probes, Inc. (Eugene, Oreg., U.S.A.).

The antibody can also be detectably labeled using fluorescence emitting metals such as $^{152}$EU, or other of the lanthanide series. These metals can be attached to the antibody using such metal groups as diethylenetriamine pentaacetic acid (EDTA).

The antibody can also be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt, and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, lucifers and aequorin.

The antibodies (or fragments thereof) useful in the present invention may be employed histologically, as in immunofluorescence or immunoelectron microscopy, for in situ detection of a laminin fragment of the present invention. In situ detection may be accomplished by removing a histological specimen from a patient, and providing the labeled antibody of the present invention to such a specimen. The antibody (or fragment) is preferably provided by applying or by overlaying the labeled antibody (or fragment) to a biological sample. Through the use of such a procedure, it is possible to determine not only the presence of a laminin fragment polypeptide but also its distribution on the examined tissue. Using the present invention, those of ordinary skill will readily perceive that any of a wide variety of histological methods (such as staining procedures) can be modified in order to achieve such in situ detection.

Antibodies against laminin fragments and/or laminin-derived polypeptides which interact with Aβ or other amyloid proteins, or derivatives thereof are also disclosed herein. These antibodies can be used for a number of important diagnostic and/or therapeutic applications as described herein. In one aspect of the invention, polyclonal and/or monoclonal antibodies made against laminin fragments and/ or laminin-derived polypeptides which bind Aβ or other amyloid proteins, may be utilized for Western blot analysis (using standard Western blotting techniques knowledgeable to those skilled in the art) to detect the presence of amyloid protein-binding laminin fragments or amyloid protein-binding laminin polypeptides in human tissues and in tissues of other species. Western blot analysis can also be used to determine the apparent size of each amyloid protein-binding laminin fragment. In addition, Western blotting following by scanning densitometry (known to those skilled in the art) can be used to quantitate and compare levels of each of the laminin fragments or polypeptides in tissue samples, biological fluids or biopsies obtained from individuals with specific diseases (such as the amyloid diseases) in comparison to tissue samples, biological fluids or biopsies obtained from normal individuals or controls. Biological fluids, include, but are not limited to, blood, plasma, serum, cerebrospinal fluid, sputum, saliva, urine and stool.

In yet another aspect of the invention, polyclonal and/or monoclonal antibodies made against laminin fragments and/ or laminin-derived peptides which bind Aβ or other amyloid proteins, can be utilized for immunoprecipitation studies (using standard immunoprecipitation techniques known to one skilled in the art) to detect laminin fragments and/or laminin-derived peptides which bind Aβ or other amyloid proteins, in tissues, cells and/or biological fluids. Use of the laminin fragment and/or laminin-derived peptide antibodies for immunoprecipitation studies can also be quantitated to determine relative levels of laminin fragments and/or laminin-derived peptides which interact with Aβ or other amyloid proteins, in tissues, cells and/or biological fluids. Quantitative immunoprecipitation can be used to compare levels of laminin fragments and/or laminin amyloid protein-binding peptides in tissue samples, biological fluids or biopsies obtained from individuals with specific diseases (such as the amyloid diseases) in comparison to tissue samples, biological fluids or biopsies obtained from normal individuals or controls.

Therapeutic Applications

Yet another aspect of the present invention is to make use of laminin fragments and/or laminin-derived polypeptides as amyloid inhibitory therapeutic agents. The laminin-derived peptide sequences or fragments can be synthesized utilizing standard techniques (i.e. using an automated synthesizer). Laminin fragments and/or laminin-derived polypeptides which bind A$\beta$ or other amyloid proteins, can be used as potential blocking therapeutics for the interaction of laminin in a number of biological processes and diseases (such as in the amyloid diseases described above). In a preferred embodiment, specific laminin-derived polypeptides may be used to aid in the inhibition of A$\beta$ amyloid formation, deposition, accumulation, and/or persistence in a given patient. Likewise, in another preferred embodiment anti-idiotypic antibodies made against laminin fragments and/or laminin-derived polypeptides (as described above) may be given to a human patient as potential blocking antibodies to disrupt continued A$\beta$ amyloid formation, deposition, accumulation and/or persistence in the given patient.

Preparations of laminin-derived polypeptides for parenteral administration include sterile aqueous or non-aqueous solutions, suspensions, and emulsions, which may contain axillary agents or excipients which are known in the art. Pharmaceutical compositions such as tablets, pills, tablets, caplets, soft and hard gelatin capsules, lozenges, sachets, cachets, vegicaps, liquid drops, elixers, suspensions, emulsions, solutions, syrups, tea bags, aerosols (as a solid or in a liquid medium), suppositories, sterile injectable solutions, sterile packaged powders, can be prepared according to routine methods and are known in the art.

In yet another aspect of the invention, laminin fragments and/or laminin-derived polypeptides may be used as an effective therapy to block A$\beta$ amyloid formation, deposition, accumulation and/or persistence as observed in the amyloid diseases. For example, the invention includes a pharmaceutical composition for use in the treatment of amyloidoses comprising a pharmaceutically effective amount of a laminin fragment and/or laminin-derived polypeptide anti-idiotypic antibody and a pharmaceutically acceptable carrier. The compositions may contain the laminin fragments and/or laminin-derived polypeptide anti-idiotypic antibody, either unmodified, conjugated to a potentially therapeutic compound, conjugated to a second protein or protein portion or in a recombinant form (i.e. chimeric or bispecific laminin fragment and/or laminin polypeptide antibody). The compositions may additionally include other antibodies or conjugates. The antibody compositions of the invention can be administered using conventional modes of administration including, but not limited to, topical, intravenous, intra-arterial, intraperitoneal, oral, intralymphatic, intramuscular or intralumbar. Intravenous administration is preferred. The compositions of the invention can be a variety of dosage forms, with the preferred form depending upon the mode of administration and the therapeutic application. Optimal dosage and modes of administration for an individual patient can readily be determined by conventional protocols.

Laminin-derived protein fragments, and laminin-derived polypeptides, or antibodies of the present invention may be administered by any means that achieve their intended purpose, for example, to treat laminin involved pathologies, such as Alzheimer's disease and other amyloid diseases, or other related pathologies, using a laminin-derived polypeptide described herein, in the form of a pharmaceutical composition.

For example, administration of such a composition may be by various parenteral routes such as subcutaneous, intravenous, intradermal, intramuscular, intraperitoneal, intranasal, transdermal or buccal routes. Alternatively, or concurrently, administration may be by the oral route. Parenteral administration can be by bolus injection or by gradual perfusion over time.

A preferred mode of using a laminin-derived polypeptide, or antibody pharmaceutical composition of the present invention is by oral administration or intravenous application.

A typical regimen for preventing, suppressing or treating laminin-involved pathologies, such as Alzheimer's disease amyloidosis, comprises administration of an effective amount of laminin-derived polypeptides, administered over a period of one or several days, up to and including between one week and about 24 months.

It is understood that the dosage of the laminin-derived polypeptides of the present invention administered in vivo or in vitro will be dependent upon the age, sex, health, and weight of the recipient, kind of concurrent treatment, if any, frequency of treatment, and the nature of the effect desired. The most preferred dosage will be tailored to the individual subject, as is understood and determinable by one of skill in the art, without undue experimentation.

The total dose required for each treatment may be administered by multiple doses or in a single dose. A laminin-derived polypeptide may be administered alone or in conjunction with other therapeutics directed to laminin-involved pathologies, such as Alzheimer's disease or other A$\beta$ amyloid diseases, as described herein.

Effective amounts of a laminin-derived polypeptide or composition, which may also include a laminin-fragment derived antibody, are about 0.01 $\mu\mu$g to about 100 mg/kg body weight, and preferably from about 10 $\mu$g to about 50 mg/kg body weight, such as 0.05, 0.07, 0.09, 0.1, 0.5, 0.7, 0.9, 1, 2, 5, 10, 20, 25, 30, 40, 45, 50, 55, 60, 65, 70, 75, 80, 85, 90, 95 or 100 mg/kg.

Preparations for parenteral administration include sterile aqueous or non-aqueous solutions, suspensions, and emulsions, which may contain axillary agents or excipients which are known in the art. Pharmaceutical compositions comprising at least one laminin-derived polypeptide, such as 1-10 or 1, 2, 3, 4, 5, 6, 7, 8, 9, or 10 laminin-derived polypeptides, of the present invention may include all compositions wherein the laminin-derived polypeptide is contained in an amount effective to achieve its intended purpose. In addition to at least one laminin-derived polypeptide, a pharmaceutical composition may contain suitable pharmaceutically acceptable carriers, such as excipients, carriers and/or axillaries which facilitate processing of the active compounds into preparations which can be used pharmaceutically.

Pharmaceutical compositions comprising at least one laminin-derived polypeptide or antibody may also include suitable solutions for administration intravenously, subcutaneously, dermally, orally, mucosally, rectally or may by injection or orally, and contain from about 0.01 to 99 percent, preferably about 20 to 75 percent of active component (i.e. polypeptide or antibody) together with the excipient. Pharmaceutical compositions for oral administration include pills, tablets, caplets, soft and hard gelatin capsules, lozenges, sachets, cachets, vegicaps, liquid drops, elixers, suspensions, emulsions, solutions, and syrups.

The laminin-derived protein fragments, and laminin-derived polypeptides for Alzheimer's disease and other central nervous system A$\beta$ amyloidoses may be optimized to cross the blood-brain barrier. Methods of introductions include but are not limited to systemic administration, parenteral administration i.e., via an intraperitoneal, intravenous, perioral, subcutaneous, intramuscular, intraarterial, intradermal, intramuscular, intranasal, epidural and oral routes. In a preferred embodiment, laminin-derived protein fragments, and laminin-derived polypeptides may be directly administered to the cerebrospinal fluid by intraventricular injection. In a specific embodiment, it may be desirable to administer laminin-derived protein fragments, and laminin-derived polypeptides locally to the area or tissue in need of treatment; this may be achieved by, for example, and not by way of limitation, local infusion during surgery, topical application, by injection, by infusion using a cannulae with osmotic pump, by means of a catheter, by means of a suppository, or by means of an implant.

In yet another embodiment laminin-derived protein fragments, and laminin-derived polypeptides may be delivered in a controlled release system, such as an osmotic pump. In yet another embodiment, a controlled release system can be placed in proximity to the therapeutic target, i.e. the brain, thus requiring only a fraction of the systemic dose.

In yet another aspect of the present invention, peptidomimetic compounds modeled from laminin fragments and/or laminin-derived polypeptides identified as binding Aβ or other amyloid proteins, may serve as potent inhibitors of amyloid formation, deposition, accumulation and/or persistence in Alzheimer's disease and other Aβ amyloidoses. Peptidomimetic modeling is implemented by standard procedures known to those skilled in the art.

In yet another aspect of the present invention, compounds that mimic the 3-dimensional Aβ binding site on laminin using computer modeling, may serve as potent inhibitors of Aβ amyloid formation, deposition, accumulation and/or persistence in Alzheimer's disease and other Aβ amyloidoses. Design and production of such compounds using computer modeling technologies is implemented by standard procedures known to those skilled in the art.

Recombinant DNA technology, including human gene therapy, has direct applicability to the laminin polypeptides, of this invention. One skilled in the art can take the peptide sequences disclosed herein and create corresponding nucleotide sequences that code for the corresponding peptide sequences. These sequences can be cloned into vectors such as retroviral vectors, and the like. These vectors can, in turn, be transfected into human cells such as hepatocytes or fibroblasts, and the like. Such transfected cells can be introduced into humans to treat amyloid diseases. Alternatively, the genes can be introduced into the patients directly. The basic techniques of recombinant DNA technology are known to those of ordinary skill in the art and are disclosed in *Recombinant DNA* Second Edition, Watson, et al., W.H. Freeman and Company, New York, 1992, which is hereby incorporated by reference.

Diagnostic Applications

Another aspect of the invention is to provide polyclonal and/or monoclonal antibodies against laminin fragments and/or laminin-derived polypeptides which bind Aβ or other amyloid proteins, which is utilized to specifically detect laminin fragments and/or laminin-derived peptides in human tissues and/or biological fluids. In one preferred embodiment, polyclonal or monoclonal antibodies made against a peptide portion or fragment of laminin, can be used to detect and quantify laminin fragments and/or laminin-derived polypeptides in human tissues and/or biological fluids. Polyclonal and/or monoclonal peptide antibodies can also be utilized to specifically detect laminin fragments and/or laminin-derived polypeptides in human tissues and/or biological fluids. In a preferred embodiment, a polyclonal or monoclonal antibody made specifically against a peptide portion or fragment of laminin fragments or polypeptides which bind Aβ (as described herein), can be used to detect and quantify these laminin fragments or polypeptides in human tissues and/or biological fluids. Other preferred embodiments include, but are not limited to, making polyclonal or monoclonal antibodies made specifically against a peptide portion or fragment of any of the peptides of Sequence Group A, as well as polypeptides which have at least 70% identity and more preferably a 90% identity to the polypeptides described above. For detection of laminin fragments and/or laminin-derived polypeptides described above in human tissues, cells, and/or in cell culture, the polyclonal and/or monoclonal antibodies can be utilized using standard immunohistochemical and immunocytochemical techniques, known to one skilled in the art.

For detection and quantitation of laminin fragments and/or laminin-derived polypeptides in biological fluids, including cerebrospinal fluid, blood, plasma, serum, urine, sputum, and/or stool, various types of ELISA assays can be utilized, known to one skilled in the art. An antibody molecule of the present invention may be adapted for utilization in an immunometric assay, also known as a "two-site" or "sandwich" assay. In a typical immunometric assay, a quantity of unlabeled antibody (or fragment of antibody) is bound to a solid support or carrier, and a quantity of detectable labeled soluble antibody is added to permit detection and/or quantitation of the ternary complex formed between solid-phase antibody, antigen, and labeled antibody.

In a preferred embodiment, a "sandwich" type of ELISA can be used. Using this preferred method a pilot study is first implemented to determine the quantity of binding of each laminin-fragment or polypeptide monoclonal antibody to microtiter wells. Once this is determined, aliquots (usually in 40 μL of TBS; pH 7.4) of the specific laminin-fragment or laminin polypeptide antibody are allowed to bind overnight to microtiter wells (Maxisorb C plate from Nunc) at 4° C. A series of blank wells not containing any laminin-fragment or laminin polypeptide specific monoclonal antibody are also utilized as controls. The next day, non-bound monoclonal antibody is shaken off the microtiter wells. All of the microtiter wells (including the blank wells) are then blocked by incubating for 2 hours with 300 μl of Tris-buffered saline containing 0.05% Tween-20 (TTBS) plus 2% bovine serum albumin, followed by 5 rinses with TTBS. 200 μl of cerebrospinal fluid, blood, plasma, serum, urine, sputum, and/or stool and/or any other type of biological sample is then diluted (to be determined empirically) in TTBS containing 2% bovine serum albumin and placed in wells (in triplicate) containing bound laminin-fragment or laminin-polypeptide antibody (or blank) and incubated for 2 hours at room temperature. The wells are then washed 5 times with TTBS. A second biotinylated-monoclonal antibody against the same laminin-derived fragment or laminin polypeptide (but which is against a different epitope) is then added to each well (usually in 40 μl of TBS; pH 7.4) and allowed to bind for 2 hours at room temperature to any laminin-fragment or laminin polypeptide captured by the first antibody. Following incubation, the wells are washed 5 times with TTBS. Bound materials are then detected by incubating with 100 μl of peroxidase-avidin complex (1:250 dilution in TTBS with 0.1% BSA) for 1 hour on a rotary shaker. After 5 washes with TTBS, a substrate solution (100 μl, OPD-Sigma Fast from Sigma Chemical Co., St. Louis, Mo., USA) is added and allowed to develop significant color (usually 8-10 minutes). The reaction is stopped with 50 μl of 4N sulfuric acid and read on a standard spectrophotometer at 490 nm. This ELISA can be utilized to determine differences in specific laminin fragments or polypeptides (and/or Aβ-binding laminin fragments or polypeptides) in biological fluids which can serve as a diagnostic marker to follow the progression in a live patient during the progression of disease (i.e. monitoring of Aβ amyloid disease as an example). In addition, quantitative changes in laminin fragments or laminin polypeptides can also serve as a prognostic indicator monitoring how a live patient will respond to treatment which targets an Aβ amyloid disease such as Alzheimer's disease. Such assays can be provided in a kit form.

A competition assay may also be employed wherein antibodies specific to laminin fragments and/or laminin-derived polypeptides are attached to a solid support and labeled laminin fragments and/or laminin-derived polypeptides and a sample derived from a host are passed over the solid support and the amount of label detected attached to the solid support can be correlated to the quantity of laminin fragments and/or laminin-derived polypeptides in the sample. This standard technique is known to one skilled in the art.

Another object of the present invention is to use laminin fragments and/or laminin-derived polypeptides, in conjunction with laminin fragment and/or laminin-derived peptide antibodies, in an ELISA assay to detect potential laminin fragment and/or laminin-derived peptide autoantibodies in human biological fluids. Such a diagnostic assay may be produced in a kit form. In a preferred embodiment, peptides containing the sequences of laminin-derived fragments and laminin-derived polypeptides as in Sequence Group A, as well as polypeptides which have at least 70% identity and more preferably a 90% identity to the polypeptides described above, will be used to initially bind to microtiter wells in an ELISA plate.

A pilot study is first implemented to determine the quantity of binding of each laminin fragment or polypeptide to microtiter wells. Once this is determined, aliquots (usually 1-2 µg in 40 µl of TBS; pH 7.4) of specific laminin fragment polypeptides (as described herein) are allowed to bind overnight to microtiter wells (Maxisorb C plate from Nunc) at 4° C. All the microtiter wells (including blank wells without the laminin fragment polypeptides) are blocked by incubating for 2 hours with 300 µl of Tris-buffered saline (pH 7.4) with 0.05% Tween-20 (TTBS), containing 2% albumin. This is followed by 5 rinses with TTBS. The patients" biological fluids (i.e., cerebrospinal fluid, blood, plasma, serum, sputum, urine, and/or stool) are then utilized and 200 µl are diluted (to be determined empirically) with TTBS containing 2% bovine serum albumin, and placed in microtiter wells (in triplicate) containing a specific laminin fragment polypeptide or blank wells (which do not contain peptide), and are incubated at 1.5 hours at room temperature.

Any autoantibodies present in the biological fluids against the laminin fragment or polypeptide will bind to the substrate bound laminin fragment polypeptide (or fragments thereof). The wells are then rinsed by washing 5 times with TTBS. 100 µl of biotinylated polyclonal goat anti-human IgG's (Sigma Chemical company, St. Louis, Mo., USA), diluted 1:500 in TTBS with 0.1% bovine serum albumin, is then aliquoted into each well. Bound materials are detected by incubating with 100 µl of peroxidase-avidin complex (1:250 dilution in TTBS with 0.1% bovine serum albumin) for 1 hour on a rotary shaker. Following 5 washes with TTBS, substrate solution (100 µl, OPD-Sigma Fast from Sigma Chemical Company, St. Louis, Mo., USA) is added and allowed to develop significant color (usually 8-10 minutes). The reaction is stopped with 50 µl of 4N sulfuric acid added to each well and read on a standard spectrophotometer at 490 nm.

This assay system can be utilized to not only detect the presence of autoantibodies against laminin fragments or polypeptides in biological fluids, but also to monitor the progression of disease by following elevation or diminution of laminin fragment or polypeptide autoantibody levels. It is believed that patients demonstrating excessive laminin fragment or polypeptide formation, deposition, accumulation and/or persistence as may be observed in the Aβ amyloid diseases, will also carry autoantibodies against the laminin fragments or laminin polypeptides in their biological fluids. Various ELISA assay systems, knowledgeable to those skilled in the art, can be used to accurately monitor the degree of laminin fragments or polypeptides in biological fluids as a potential diagnostic indicator and prognostic marker for patients during the progression of disease (i.e. monitoring of an Aβ amyloid disease for example). Such assays can be provided in a kit form. In addition, quantitative changes in laminin fragment or polypeptide autoantibody levels can also serve as a prognostic indicator monitoring how a live patient will respond to treatment which targets an Aβ amyloid disease.

Other diagnostic methods utilizing the invention include diagnostic assays for measuring altered levels of laminin fragments and/or laminin-derived polypeptides in various tissues compared to normal control tissue samples. Assays used to detect levels of laminin fragments and/or laminin-derived polypeptides in a sample derived from a host are well-known to those skilled in the art and included radio-immunoassays, competitive-binding assays, Western blot analysis and preferably ELISA assays (as described above).

Yet another aspect of the present invention is to use the antibodies recognizing laminin fragments and/or laminin-derived polypeptides for labelings, for example, with a radionucleotide, for radioimaging or radioguided surgery, for in vivo diagnosis, and/or for in vitro diagnosis. In one preferred embodiment, radiolabeled peptides or antibodies made (by one skilled in the art) against laminin fragments and/or laminin-derived polypeptides may be used as minimally invasive techniques to locate laminin fragments and/or laminin-derived polypeptides, and concurrent Aβ amyloid deposits in a living patient. These same imaging techniques can then be used at regular intervals (i.e. every 6 months) to monitor the progression of the Aβ amyloid disease by following the specific levels of laminin fragments and/or laminin-derived polypeptides.

Yet another aspect of the present invention is to provide a method which can evaluate a compound's ability to alter (diminish or eliminate) the affinity of Aβ (as described herein) or amyloid precursor protein, to laminin-derived fragments or laminin-derived polypeptides. By providing a method of identifying compounds which affect the binding of Aβ amyloid protein, or amyloid precursor protein to such laminin-derived fragments or polypeptides, the present invention is also useful in identifying compounds which can prevent or impair such binding interactions. Thus, compounds can be identified which specifically affect an event linked with Aβ amyloid formation, amyloid deposition, and/or amyloid persistence condition associated with Alzheimer's disease and other Aβ amyloid diseases as described herein.

According to one aspect of the invention, to identify for compounds which allow the interaction of Aβ† amyloid proteins or precursor proteins to laminin-derived fragments or laminin polypeptides, either Aβ† amyloid or laminin fragments or polypeptides are immobilized, and the other of the two is maintained as a free entity. The free entity is contacted with the immobilized entity in the presence of a test compound for a period of time sufficient to allow binding of the free entity to the immobilized entity, after which the unbound free entity is removed. Using antibodies that recognize the free entity, or other means to detect the presence of bound components, the amount of free entity bound to immobilized entity can be measured. By performing this assay in the presence of a series of known concentrations of test compound and, as a control, the complete absence of test compound, the effectiveness of the test compound to allow binding of free entity to immobilized entity can be determined and a quantitative determination of the effect of the test compound on the affinity of free entity to immobilized entity can be made. By comparing the binding affinity of the Aβ amyloid-laminin fragment or polypeptide complex in the presence of a test compound to the binding affinity of the amyloid-laminin fragment or polypeptide complex in the absence of a test compound, the ability of the test compound to modulate the binding can be determined. In the case in which the Aβ amyloid is immobilized, it is contacted with free laminin-derived fragments or polypeptides, in the presence of a series of concentrations of test compound. As a control, immobilized Aβ amyloid is contacted with free laminin-derived polypeptides, or fragments thereof in the absence of the test compound. Using a series of concentrations of laminin-derived polypeptides, the dissociation constant ($K_d$) or other indicators of binding affinity of amyloid-laminin fragment or polypeptide binding can be determined. In the assay, after the laminin-derived polypeptides or fragments thereof are placed in contact with the immobilized Aβ amyloid for a sufficient time to allow binding, the unbound laminin polypeptides are removed. Subsequently, the level of laminin fragment or polypeptide-Aβ amyloid binding can be observed. One method uses laminin-derived fragment or polypeptide antibodies, as described in the invention, to detect the amount of specific laminin fragments or polypeptides bound to the Aβ amyloid or the amount of free laminin fragments remaining in solution. This information is used to determine first qualitatively whether or not the test compound can allow continued binding between laminin-derived fragments or polypeptides and Aβ amyloid. Secondly, the data collected from assays performed using a series of test compounds at various concentrations, can be used to measure quantitatively the binding affinity of the laminin fragment or polypeptide-Aβ amyloid complex and thereby determine the effect of the test compound on the affinity between laminin fragments or polypeptides and Aβ amyloid. Using this information, compounds can be identified which do not modulate the binding of specific laminin fragments or polypeptides to amyloid and thereby allow the laminin-fragments or polypeptides to reduce the Aβ amyloid formation, deposition, accumulation and/or persistence, and the subsequent development and persistence of Aβ amyloidosis.

Therefore a kit for practicing a method for identifying compounds useful which do not alter laminin-derived fragments or laminin-derived polypeptides to an immobilized Aβ amyloid protein, said kit comprising a) a first container having Aβ amyloid protein immobilized upon the inner surface, b) a second container which contains laminin-derived fragments or laminin-derived polypeptides dissolved in solution, c) a third container which contains antibodies specific for said laminin-derived fragments or laminin-derived polypeptides, said antibodies dissolved in solution, and d) a fourth container which contains labeled antibodies specific for laminin-derived fragments or laminin-derived polypeptides, said antibodies dissolved in solution.

With regard to systems and components above referred to, but not otherwise specified or described in detail herein, the workings and specifications of such systems and components and the manner in which they may be made or assembled or used, both cooperatively with each other and with the other elements of the invention described herein to effect the purposes herein disclosed, are all believed to be well within the knowledge of those skilled in the art. No concerted attempt to repeat here what is generally known to the artisan has therefore been made.

In compliance with the statute, the invention has been described in language more or less specific as to structural features. It is to be understood, however, that the invention is not limited to the specific features shown, since the means and construction shown comprise preferred forms of putting the invention into effect. The invention is, therefore, claimed in any of its forms or modifications within the legitimate and valid scope of the appended claims, appropriately interpreted in accordance with the doctrine of equivalents.

TABLE 1

Summary of the effects of Peptides on Ab42 fibril Analyzed at Ab42:Peptide wt/wt ratio of 1:2

| SEQ ID NO: | | | | % Loss of 218 CD ellipticity |
|---|---|---|---|---|
| 1 | RKRLQVQLSIRT # | AG73 or A1 | 12aa | −21.6 (gain) |
| 3 | RQVFQVAYIIKA ### | A13 | 13aa | 37.5 |
| 8 | YLSKGRLVFALG | HA3G76 | 12aa | 58.5 * |
| 11 | TLFLAHGRLVFM ## | A4G82 | 12aa | 85.6 **** |
| 15 | AGQWHRVSVRWG | A5G81 | 12aa | 91.6 ****** |
| 18 | DGRWHRVAVIMG | A5G101 | 12aa | 89.0 ***** |
| 4 | HQTWTRNLQVTL | HA3G47 | 12aa | −20.2 (gain) |
| 5 | ISNVFVQRLSLS | HA3G58 | 12aa | 3.85 |
| 7 | RGLVFHTGTKNSF | HA3G74 | 13aa | 34.4 |
| 10 | GNSTISIRAPVY | HA3G83 | 12aa | 30.5 |
| 16 | VRWGMQQIQLVV | A5G82 | 12aa | 27.6 |
| 19 | APVNVTASVQIQ | A5G109 | 12aa | 14.9 |
| 34 | TRISLQVQLRKR # | rAG73 or A1 | 12aa | 43.3 |
| 35 | AKIIIYAVQFVQR ### | rA13 | 13aa | 7.0 |
| 36 | GLAFVLRGKSLY | rHA3G76 | 12aa | 76.0 *** |
| 37 | MFVLRGHALFLT ## | rA4G82 | 12aa | 48.1 |
| 38 | GWRVSVRHWQGA | rA5G81 | 12aa | 58.6 ** |
| 39 | GMIVAVRHWRGD | rA5G101 | 12aa | 48.8 |

We claim:

1. A pharmaceutical composition comprising a peptide HA3G76 consisting of Gly-Leu-Ala-Phe-Val-Leu-Arg-Gly-Lys-Ser-Leu-Tyr (SEQ ID NO:36).

2. The pharmaceutical composition of claim 1, wherein any individual amino acid within the peptide may be either a L- or D-amino acid.

3. The pharmaceutical composition of claim 1, further comprising a pharmaceutically acceptable carrier, diluent or excipient.

4. The pharmaceutical composition of claim 1, wherein each of the amino acids of the composition are D-amino acids.

* * * * *